United States Patent
Reardon et al.

(10) Patent No.: US 10,851,117 B2
(45) Date of Patent: Dec. 1, 2020

(54) METHODS OF PREPARING CYTOTOXIC BENZODIAZEPINE DERIVATIVES

(71) Applicant: IMMUNOGEN, INC., Waltham, MA (US)

(72) Inventors: Michael Reardon, North Attleboro, MA (US); Richard A. Silva, Needham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 16/679,563

(22) Filed: Nov. 11, 2019

(65) Prior Publication Data
US 2020/0172555 A1    Jun. 4, 2020

Related U.S. Application Data

(60) Provisional application No. 62/758,814, filed on Nov. 12, 2018.

(51) Int. Cl.
| | |
|---|---|
| *C07D 487/04* | (2006.01) |
| *C07C 231/12* | (2006.01) |
| *C07C 319/22* | (2006.01) |
| *C07D 519/00* | (2006.01) |
| *C07C 233/07* | (2006.01) |
| *C07C 319/20* | (2006.01) |
| *C07C 321/20* | (2006.01) |

(52) U.S. Cl.
CPC .......... *C07D 519/00* (2013.01); *C07C 231/12* (2013.01); *C07C 233/07* (2013.01); *C07C 319/20* (2013.01); *C07C 321/20* (2013.01); *C07D 487/04* (2013.01)

(58) Field of Classification Search
CPC .... C07D 487/04; C07C 231/12; C07C 319/22
See application file for complete search history.

(56) References Cited

FOREIGN PATENT DOCUMENTS

| | | |
|---|---|---|
| WO | 2017/015495 A1 | 1/2017 |
| WO | 2017/015496 A1 | 1/2017 |
| WO | 2018/140435 A1 | 8/2018 |

OTHER PUBLICATIONS

International Search Report and Written Opinion for Application No. PCT/US2019/060677, dated Feb. 4, 2020, 15 pages.

*Primary Examiner* — Bruck Kifle
(74) *Attorney, Agent, or Firm* — McCarter & English, LLP; Steven G. Davis; Xin Zhang

(57) ABSTRACT

The invention provides novel methods for preparing indolinobenzodiazepine dimer compounds and their synthetic precursors.

20 Claims, 20 Drawing Sheets

METHODS OF PREPARING CYTOTOXIC BENZODIAZEPINE DERIVATIVES

RELATED APPLICATION

This application claims the benefit of the filing date, under 35 U.S.C. § 119(e), of U.S. Provisional Application No. 62/758,814 filed on Nov. 12, 2018. The entire content of the above-referenced application is incorporated herein by reference.

FIELD OF THE INVENTION

The present invention relates to novel methods for preparing cytotoxic indolinobenzodiazepine derivatives.

BACKGROUND OF THE INVENTION

It has been shown that cell-binding agent conjugates of indolinobenzodiazepine compounds that have one imine functionality and one amine functionality display a much higher therapeutic index (ratio of maximum tolerated dose to minimum effective dose) in vivo compared to previously disclosed benzodiazepine derivatives having two imine functionalities. See, for example, WO 2012/128868. The previously disclosed method for making the indolinobenzodiazepine compounds with one imine functionality and one amine functionality involves partial reduction of indolinobenzodiazepine compounds having two imine functionalities. The partial reduction step generally leads to the formation of fully reduced by-product and unreacted starting material, which requires cumbersome purification steps.

Thus, there exists a need for improved methods which are more efficient and suitable for large scale manufacturing of indolinobenzodiazepine compounds.

SUMMARY OF THE INVENTION

In one embodiment, the present invention provides a method of preparing a compound of formula (IIA):

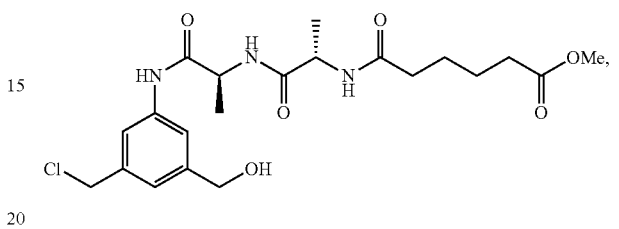

(IIA)

comprising reacting a compound of formula (IA):

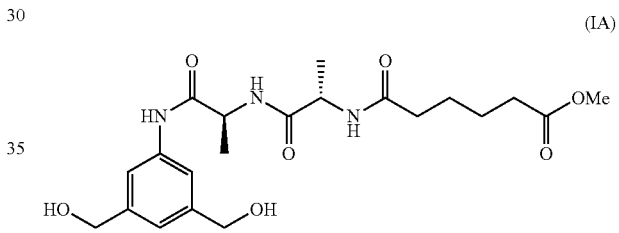

(IA)

with cyanuric chloride to form the compound of formula (IIA).

In another embodiment, the present invention provides a method of preparing a compound of formula (IVA):

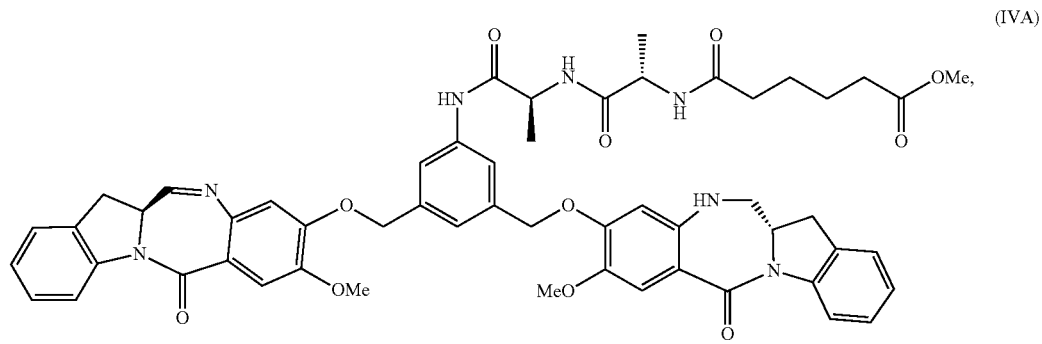 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

(IVA)

comprising the steps of:
1) reacting a compound of formula (IA):

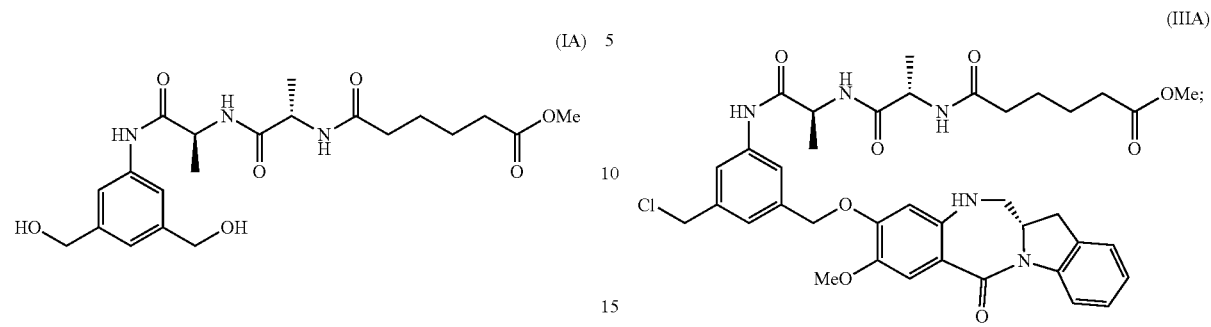

(IA)

with cyanuric chloride to form a compound of formula (IIA):

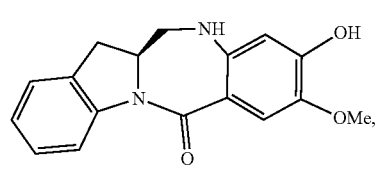

(IIA)

2) reacting the compound of formula (IIA) with a compound of formula (a):

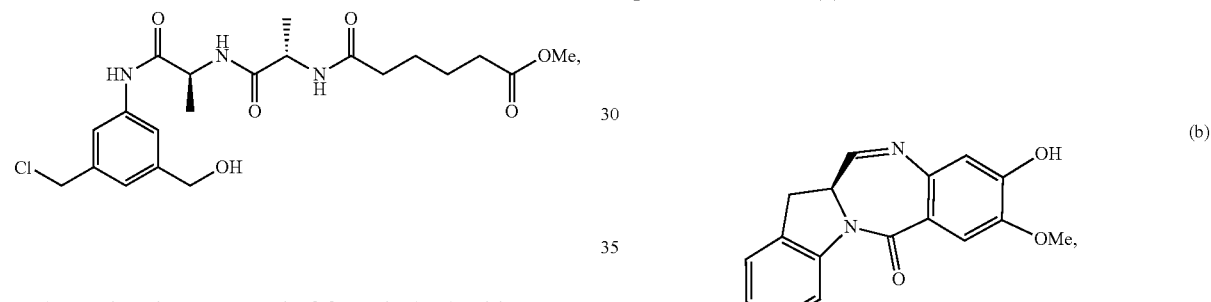

(a)

to form a compound of formula (IIIA):

(IIIA)

and 3) reacting the compound of formula (IIIA) with a compound of formula (b):

(b)

to form the compound of formula (IVA).

In another embodiment, the present invention provides a method of preparing a compound of formula:

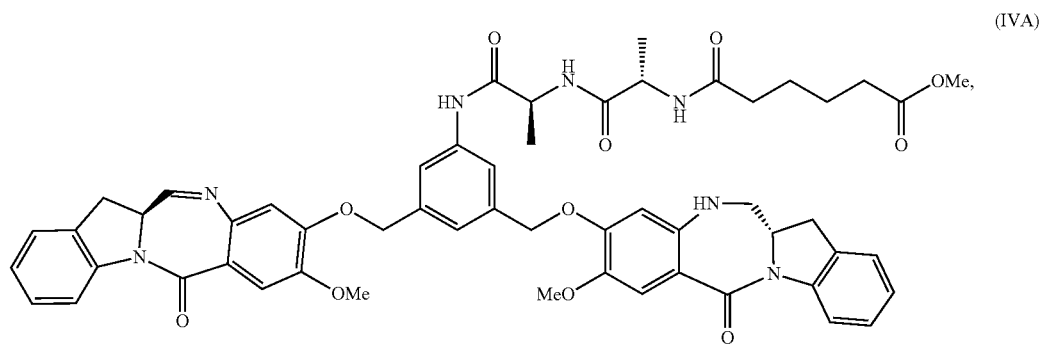 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

(IVA)

comprising the steps of:
1) reacting a compound of formula (IA):

(IA)
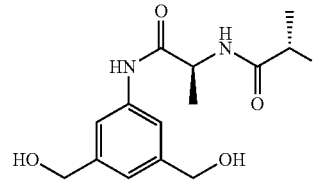

with cyanuric chloride to form a compound of formula (IIA):

(IIA)
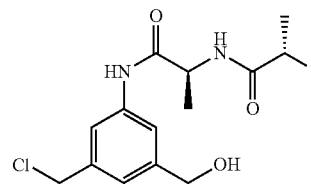

2) reacting the compound of formula (IIA) with a sulfonating agent to form a compound of formula (VIA):

(VIA)
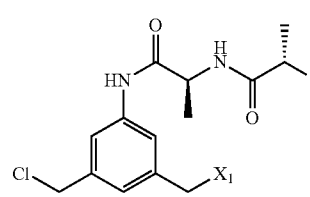

3) reacting the compound of formula (VIA) with a compound of formula (a):

(a)
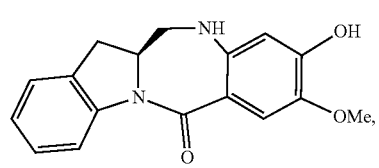

to form a compound of formula (IIIA):

(IIIA)
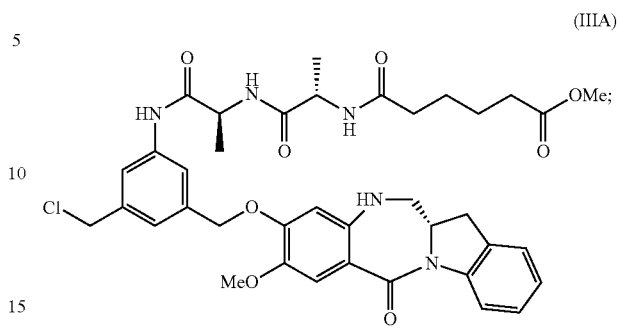

and
4) reacting the compound of formula (IIIA) with a compound of formula (b):

(b)
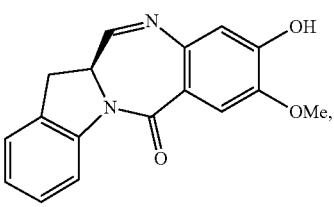

to form the compound of formula (IVA).

In another embodiment, the present invention provides a method of preparing a compound of formula (IIB):

(IIB)

MeO$\sim$O$\sim$O$\sim$N$\sim$S$_\sim$S$\sim$,

HO$\sim$Cl comprising reacting a compound of formula (IB):

(IB)

MeO$\sim$O$\sim$O$\sim$N$\sim$S$_\sim$S$\sim$,

HO$\sim$OH with cyanuric chloride to form the compound of formula (IIB).

In yet another embodiment, the present invention provides a method of preparing a compound of formula (IVB):
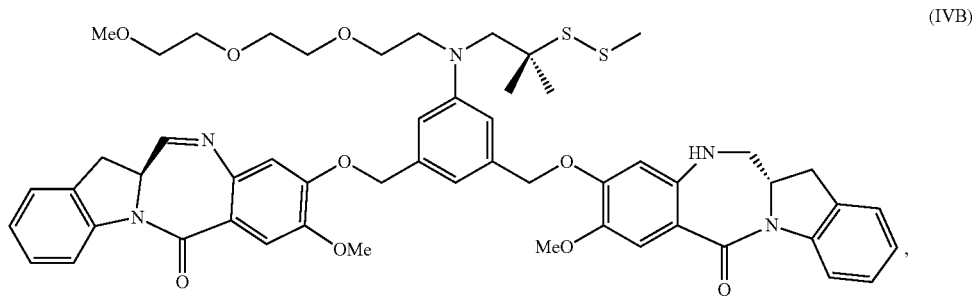
(IVB)
comprising the steps of:
1) reacting a compound of formula (IB):
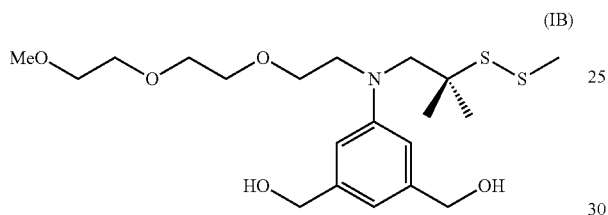
(IB)
with cyanuric chloride to form a compound of formula (IIB):
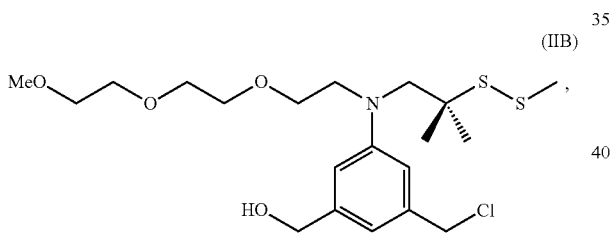
(IIB)
2) reacting the compound of formula (IIB) with a compound of formula (a):
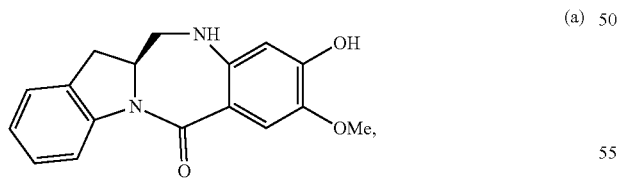
(a)

to form a compound of formula (IIIB):
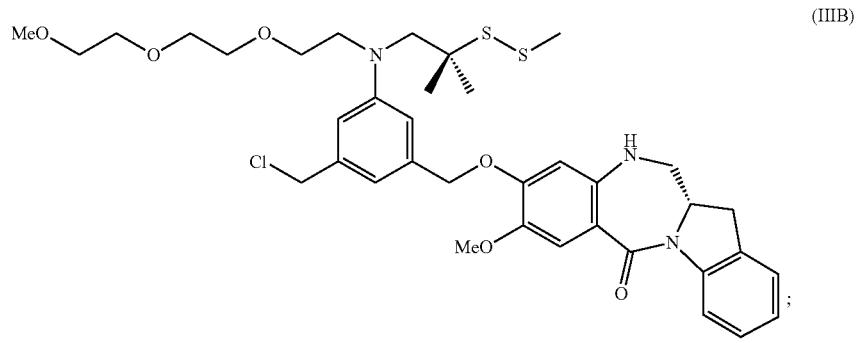
and
3) reacting the compound of formula (IIIB) with a compound of formula (b):
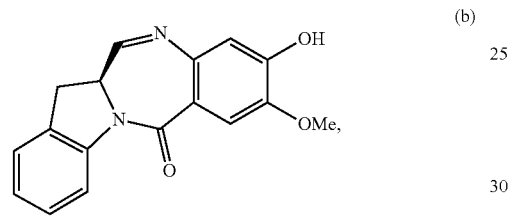
to form the compound of formula (IVB).
In yet another embodiment, the present invention provides a method of method of preparing a compound of formula (IVB):
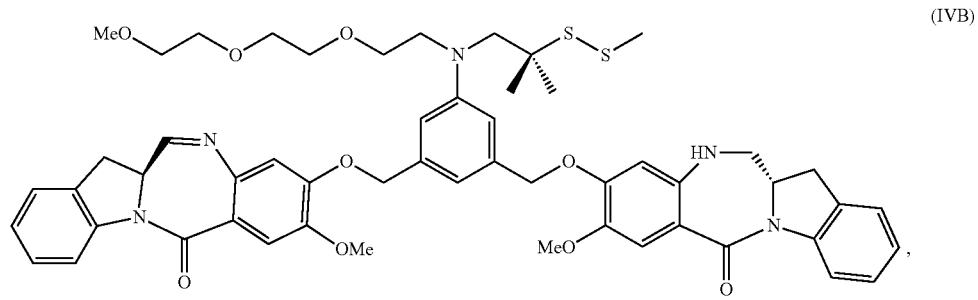
comprising the steps of:
1) reacting a compound of formula (IB):
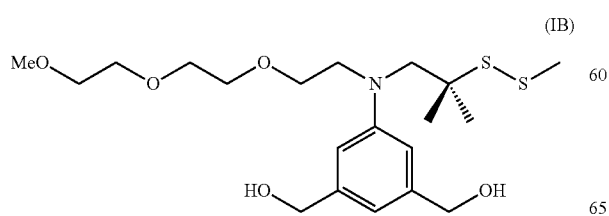

with cyanuric chloride to form a compound of formula (IIB):

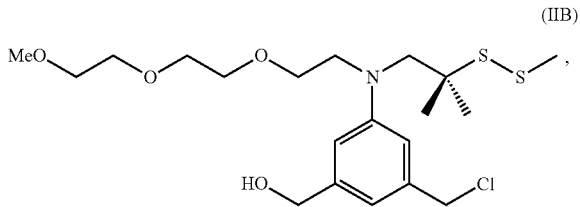
(IIB)

2) reacting the compound of formula (IIB) with sulfonating agent to form a compound of formula (VIB):

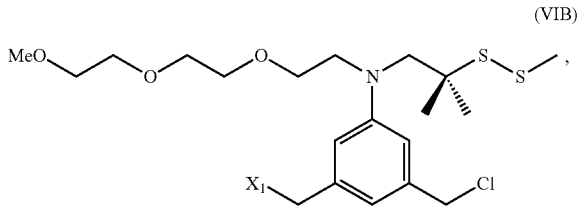
(VIB)

3) reacting the compound of formula (VIB) with a compound of formula (a):

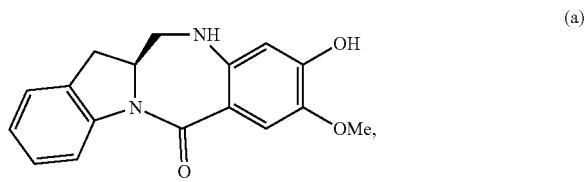 [SMILES: COc1cc2c(cc1O)NC[C@@H]1Cc3ccccc3N1C2=O]
(a)

to form a compound of formula (IIIB):

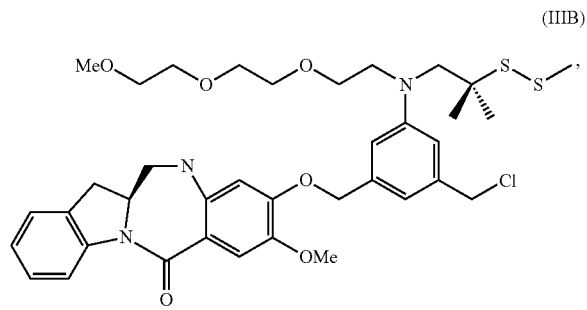
(IIIB)

and 4) reacting the compound of formula (IIIB) with a compound of formula (b):

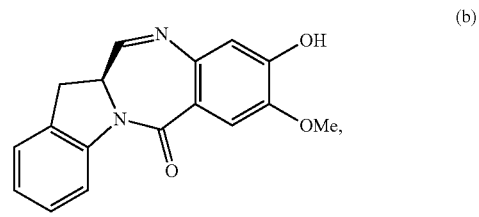 [SMILES: COc1cc2c(cc1O)N=C[C@@H]1Cc3ccccc3N1C2=O]
(b)

to form the compound of formula (IVB).

DETAILED DESCRIPTION OF THE INVENTION

Figure 1A:
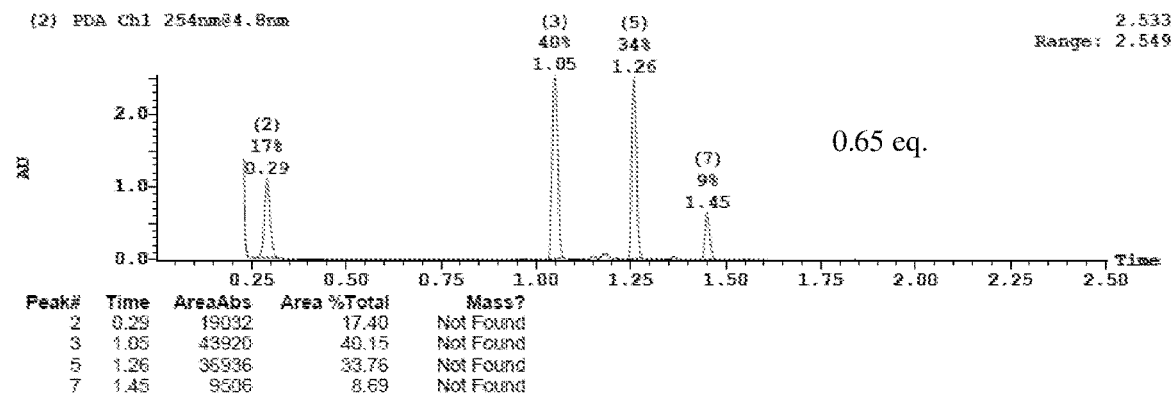
FIGS. 1A-1D show HPLC chromatograms of reactions between compound (IA) and cyanuric chloride.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

Definitions

As used herein, the term "compound" is intended to include compounds for which a structure or formula or any derivative thereof has been disclosed in the present invention or a structure or formula or any derivative thereof that has been incorporated by reference. The term also includes, stereoisomers, geometric isomers, or tautomers. The specific recitation of "stereoisomers," "geometric isomers," "tautomers," in certain aspects of the invention described in this application shall not be interpreted as an intended omission of these forms in other aspects of the invention where the term "compound" is used without recitation of these other forms.

As used herein, the term "stereoisomer" refers to compounds which have identical chemical constitution and connectivity, but different orientations of their atoms in space that cannot be interconverted by rotation about single bonds.

As used herein, the term "diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

As used herein, the term "enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "alcohol activating agent" refers a reagent that increases the reactivity of a hydroxyl group thereby making the hydroxyl group a better leaving group.

As used herein, the term "sulfonating reagent" refers to a reagent that converts an alcohol group to a sulfonate ester group. Preferably, the sulfonating reagent is a sulfonic anhydride, such as methanesulfonic anhydride ($Ms_2O$), or a sulfonic chloride, such as methanesulfonyl chloride (MsCl).

As used herein, the term "imine reducing reagent" refers to a reagent that is capable of reducing an imine functional group to an amine functional group. In certain embodiments, the imine reducing reagent is a hydride reducing reagent. Examples of such imine reducing reagents include, but are not limited to, borohydrides (e.g., sodium borohydride, sodium triacetoxy borohydride, sodium cyanoborohydride, lithium borohydride ($LiBH_4$), potassium borohydride ($KBH_4$)), hydrogen gas, and lithium aluminum hydride, ammonium formate, borane, 9-borabicyclo[3.3.1]nonane (9-BBN), diisobutylaluminium hydride (DIBAL), and sodium bis(2-methoxyethoxy)aluminumhydride (Red-Al). In certain embodiments, the imine reducing reagent is sodium triacetoxy borohydride.

As used herein, the term "cyanuric chloride," or "2,4,6-trichloro-1,3,5-triazine" refers to the compound of the following formula (CAS Number 108-77-0):

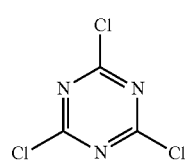

As used herein, the volume amount means the ratio of the solvent volume (in mL) versus the weight amount (in g) of the compound. For example, 40 volume amount means that 40 mL of solvent is used per 1 g of the compound.

METHODS OF THE PRESENT INVENTION

The present invention provides a method for selective monochlorination for making synthetic precursors of benzodiazepine dimer compounds. It is surprisingly discovered that using certain molar equivalent of cyanuric chloride relative to the starting diol compound affords the monochlorinated product in higher yield.

In a first embodiment, the present invention provides a method of preparing a compound of formula (IIA'):

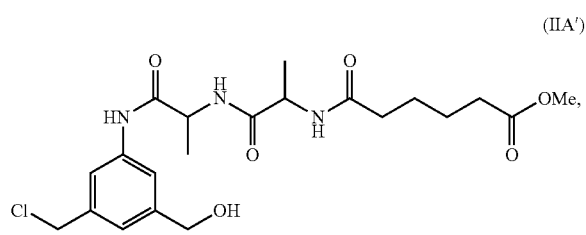 [SMILES: COC(=O)CCCCC(=O)NC(C)C(=O)NC(C)C(=O)Nc1cc(CO)cc(CCl)c1]

(IIA')

comprising reacting a compound of formula (IA'):

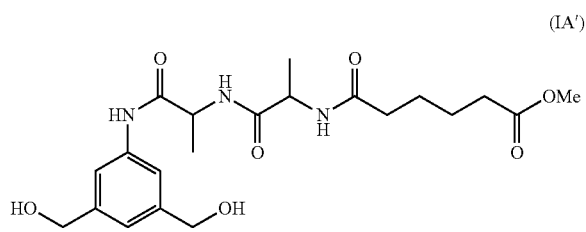 [SMILES: COC(=O)CCCCC(=O)NC(C)C(=O)NC(C)C(=O)Nc1cc(CO)cc(CO)c1]

(IA')

with cyanuric chloride to form the compound of formula (IIA').

In a $1^{st}$ specific embodiment, the present invention provides a method of preparing a compound of formula (IIA):

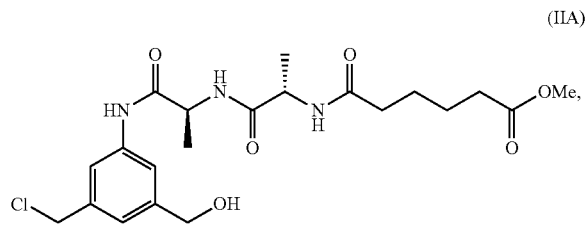 [SMILES: COC(=O)CCCCC(=O)N[C@@H](C)C(=O)N[C@@H](C)C(=O)Nc1cc(CO)cc(CCl)c1]

(IIA)

comprising reacting a compound of formula (IA):

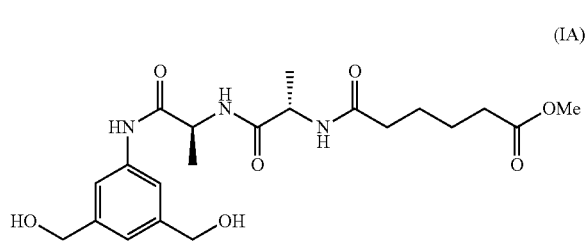 [SMILES: COC(=O)CCCCC(=O)N[C@@H](C)C(=O)N[C@@H](C)C(=O)Nc1cc(CO)cc(CO)c1]

(IA)

with cyanuric chloride to form the compound of formula (IIA).

In a second embodiment, the method of the first embodiment further comprises reacting the compound of formula (IIA') with a compound of formula (a):

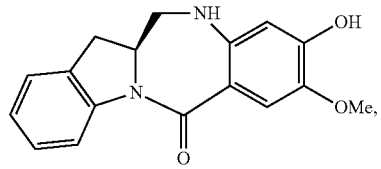
(a)

to form a compound of formula (IIIA'):

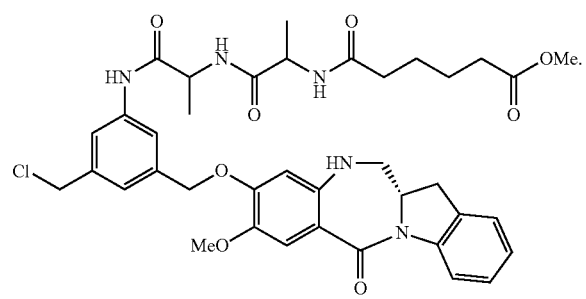
(IIIA')

to form a compound of formula (IIIA):

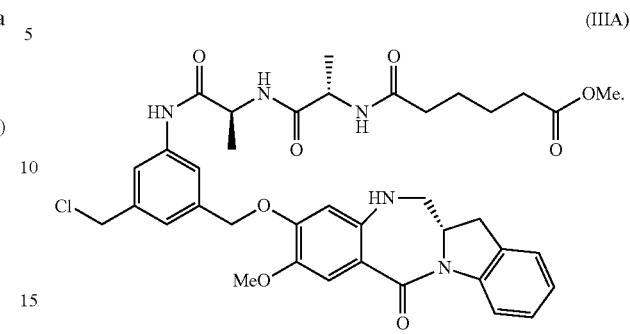
(IIIA)

In a third embodiment, the method of the second embodiment further comprises reacting the compound of formula (IIIA') with a compound of formula (b):

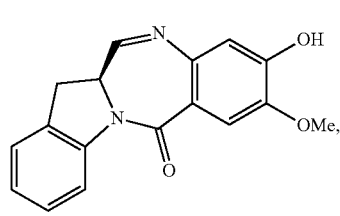
(b)

to form a compound of formula (IVA'):

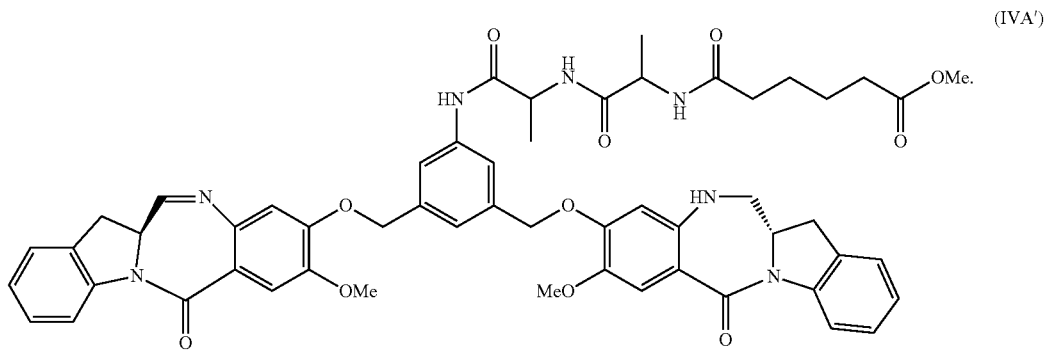 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA')

In a 2$^{nd}$ specific embodiment, the method of the 1$^{st}$ specific embodiment further comprises reacting the compound of formula (IIA) with a compound of formula (a):

In a 3$^{rd}$ specific embodiment, the method of the 2$^{nd}$ specific embodiment further comprises reacting the compound of formula (IIIA) with a compound of formula (b):

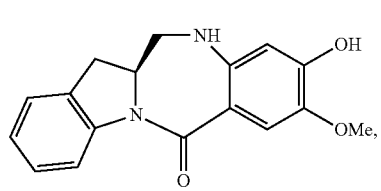
(a)

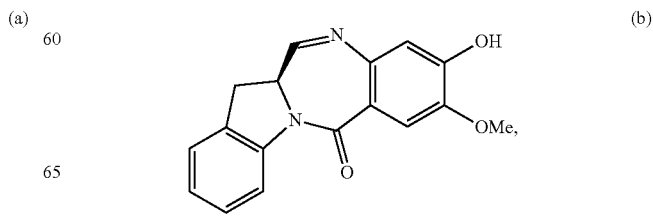
(b)

to form a compound of formula (IVA):
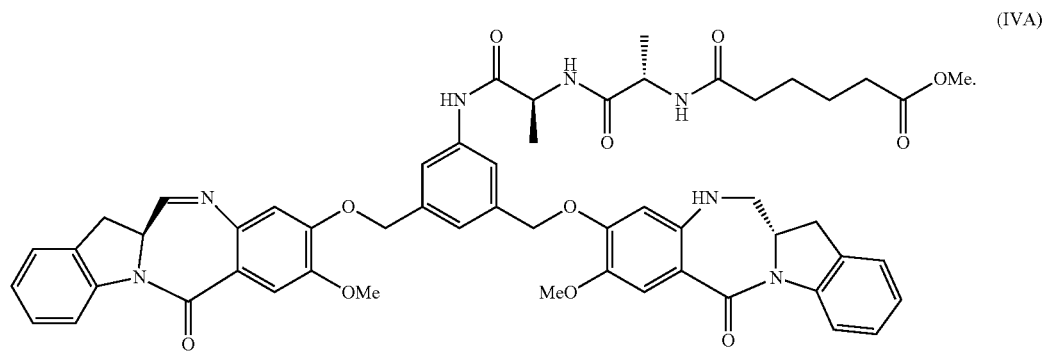 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
In a fourth embodiment, the present invention provides a method of preparing a compound of formula (IVA'):
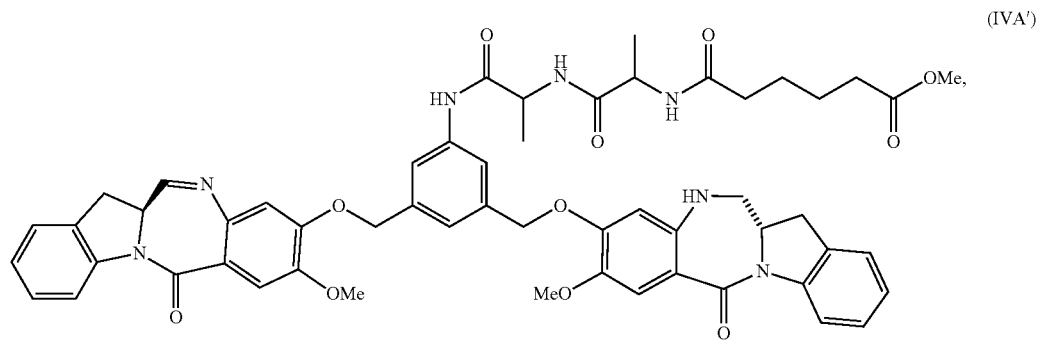 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA')
comprising the steps of:
1) reacting a compound of formula (IA'):
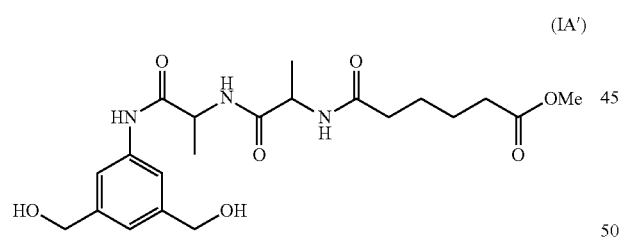
(IA')
with cyanuric chloride to form a compound of formula (IIA'):
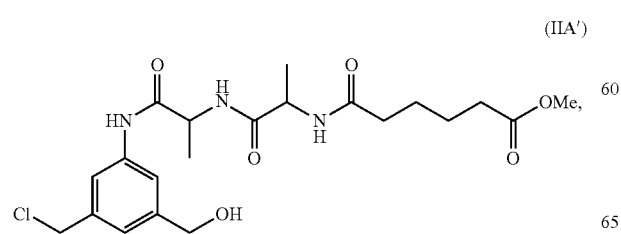
(IIA')

2) reacting the compound of formula (IIA') with a compound of formula (a):
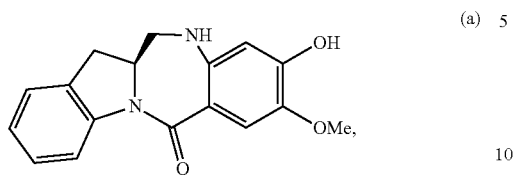
to form a compound of formula (IIIA'):
(IIIA')
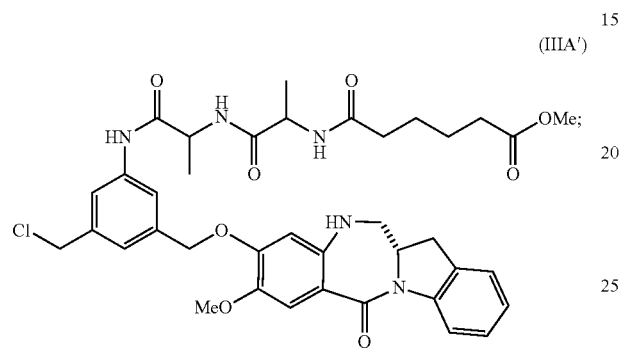
and
3) reacting the compound of formula (IIIA') with a compound of formula (b):
(b)
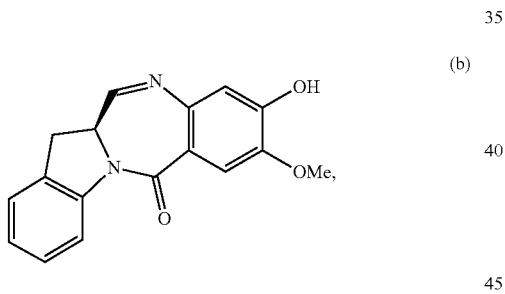
to form the compound of formula (IVA').
In a 4$^{th}$ specific embodiment, the present invention provides a method of preparing a compound of formula (IVA):
(IVA)
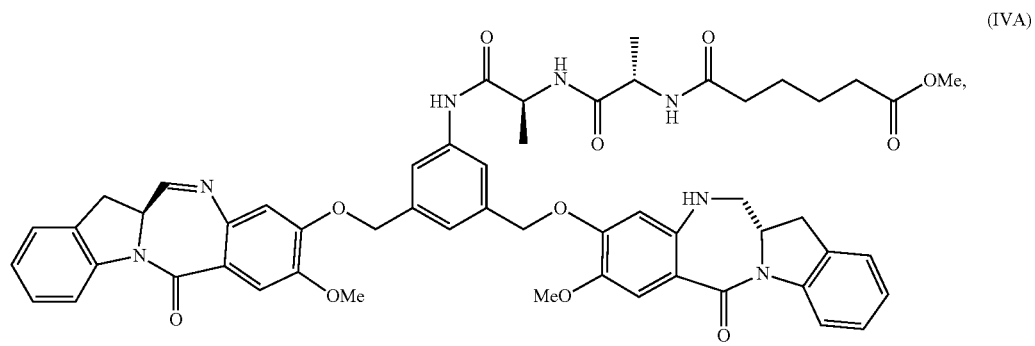 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

comprising the steps of:
1) reacting a compound of formula (IA):

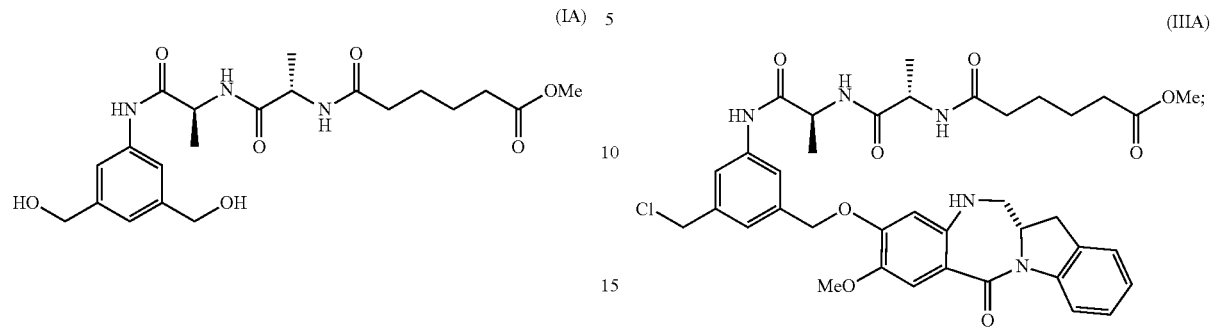

with cyanuric chloride to form a compound of formula (IIA):

2) reacting the compound of formula (IIA) with a compound of formula (a):

to form a compound of formula (IIIA):

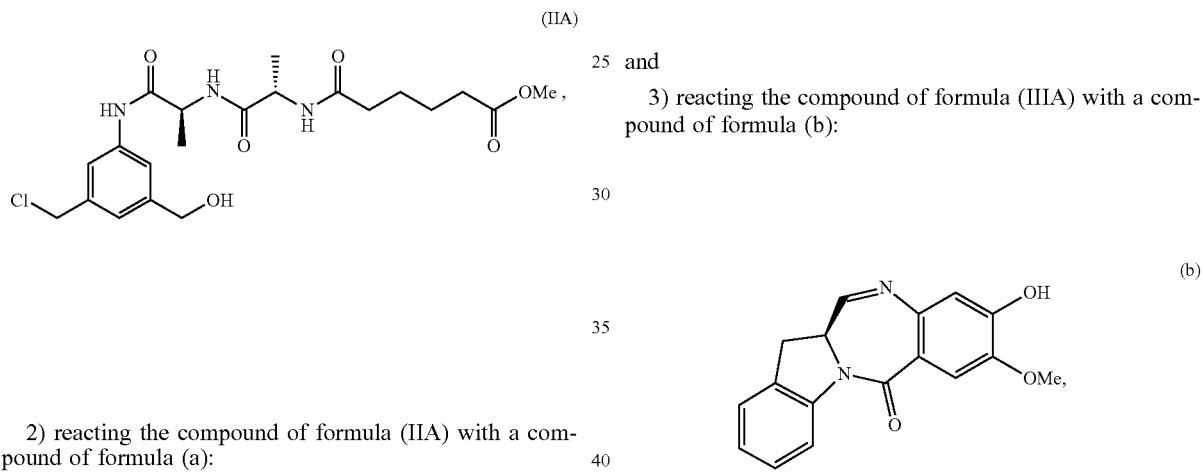

and 3) reacting the compound of formula (IIIA) with a compound of formula (b):

to form the compound of formula (IVA).

In a fifth embodiment, the present invention provides a method of preparing a compound (IVA'):

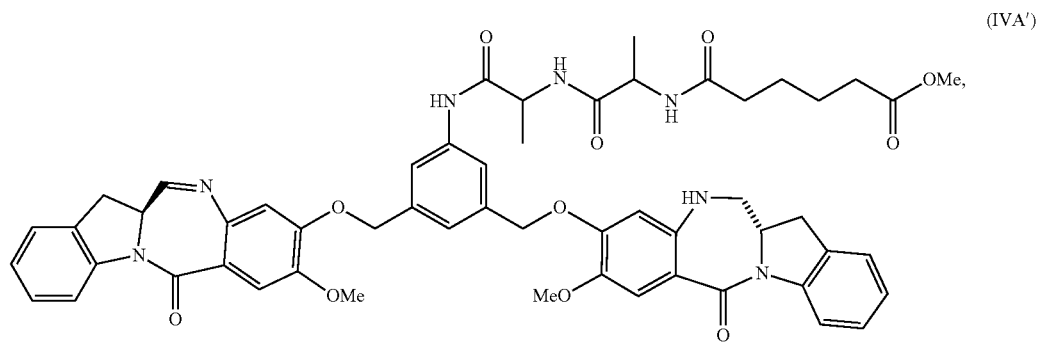 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

comprising the steps of:
1) reacting a compound of formula (IA'):
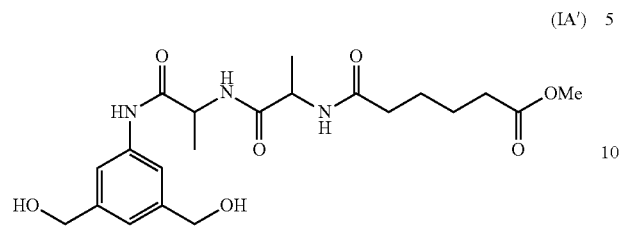
(IA')
with cyanuric chloride to form a compound of formula (IIA'):
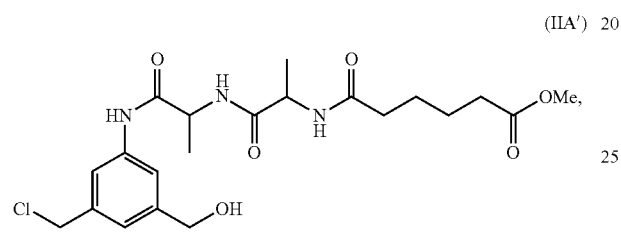
(IIA')
2) reacting the compound of formula (IIA') with a compound of formula (b):
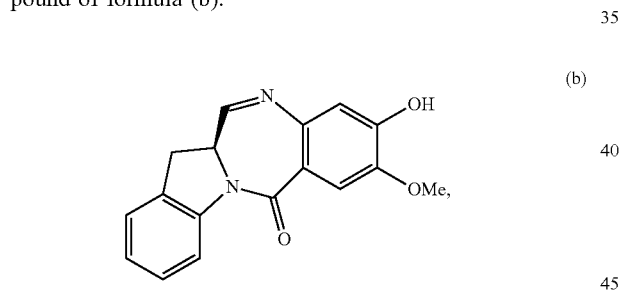
(b)
to form a compound of formula (VA'):
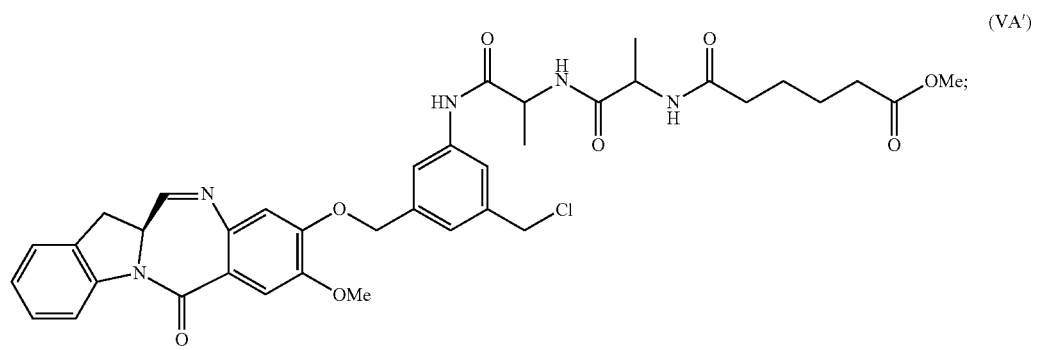 [SMILES: COC(=O)CCCCC(=O)NC(C)C(=O)NC(C)C(=O)Nc1cc(CCl)cc(COc2cc3c(cc2OC)C(=O)N2c4ccccc4C[C@H]2C=N3)c1]
(VA')

and 3) reacting the compound of formula (VA') with a compound of formula (a):

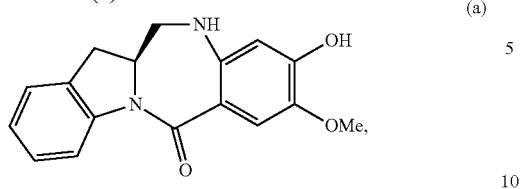
(a)

to form the compound of formula (IVA').

In a 5th specific embodiment, the present invention provides a method of preparing a compound of formula (IVA):

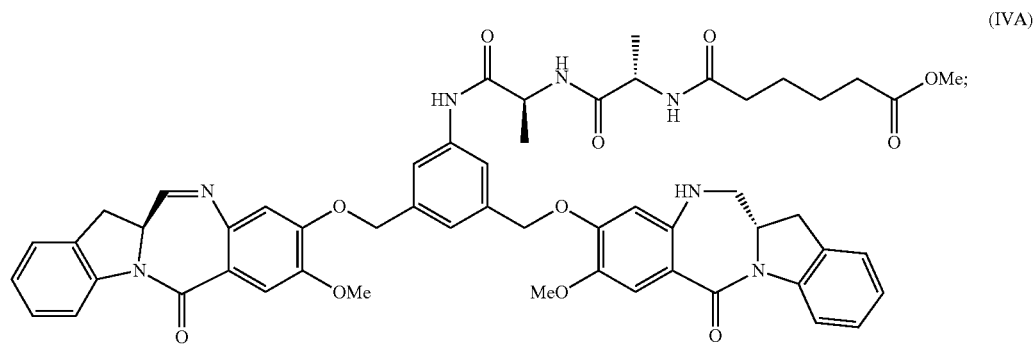 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)

comprising the steps of:

1) reacting a compound of formula (IA):

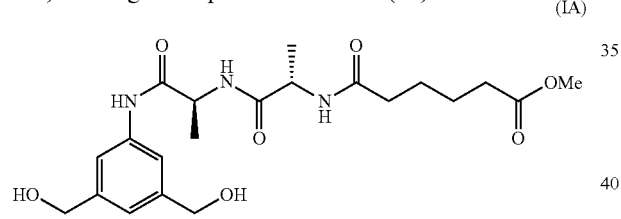
(IA)

with cyanuric chloride to form a compound of formula (IIA):

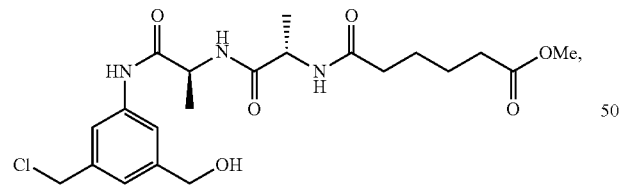
(IIA)

2) reacting the compound of formula (IIA) with a compound of formula (b):

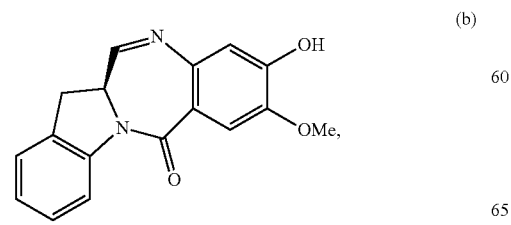
(b)

to form a compound of formula (VA):
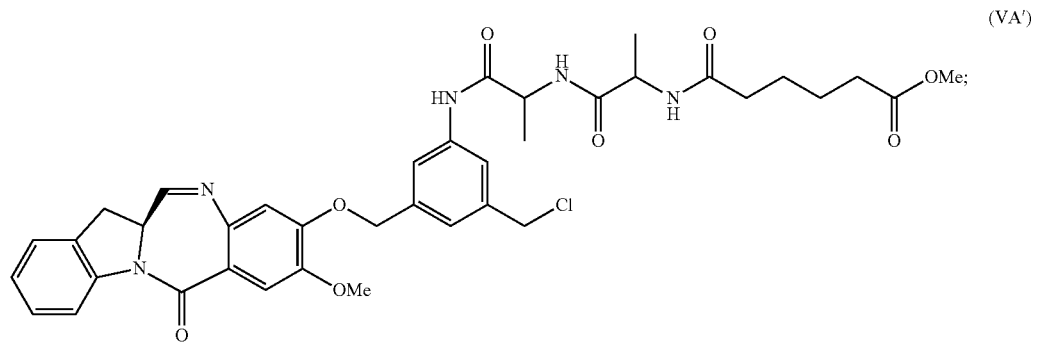 [SMILES: COC(=O)CCCCC(=O)NC(C)C(=O)NC(C)C(=O)Nc1cc(CCl)cc(COc2cc3c(cc2OC)C(=O)N2c4ccccc4C[C@H]2C=N3)c1]
and
3) reacting the compound of formula (VA) with a compound of formula (a):
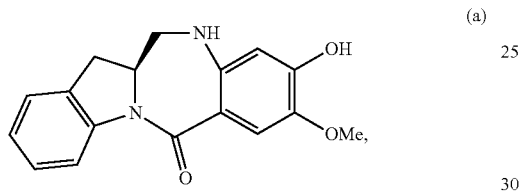
to form the compound of formula (IVA).
In a sixth embodiment, the present invention provides a method of preparing a compound of formula compound (IVA'):
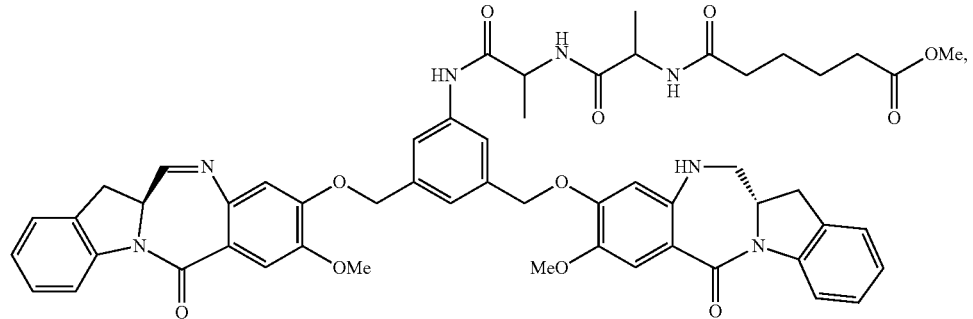 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
comprising the steps of:
1) reacting a compound of formula (IA'):
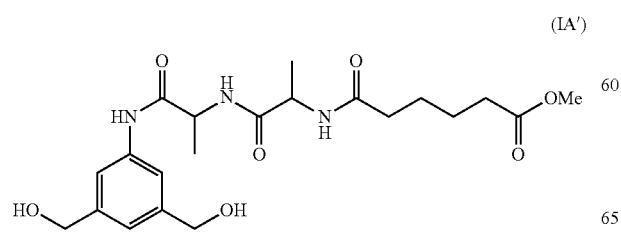

with cyanuric chloride to form a compound of formula (IIA'):
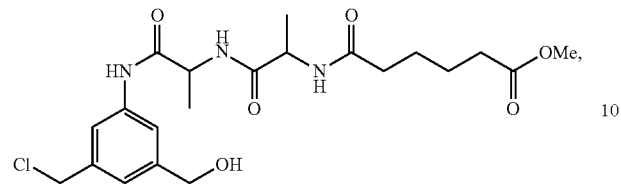
(IIA')
2) reacting the compound of formula (IIA') with a compound of formula (b):
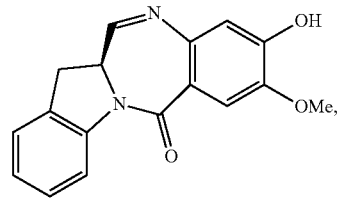
(b)
to form a compound of formula (VA'):
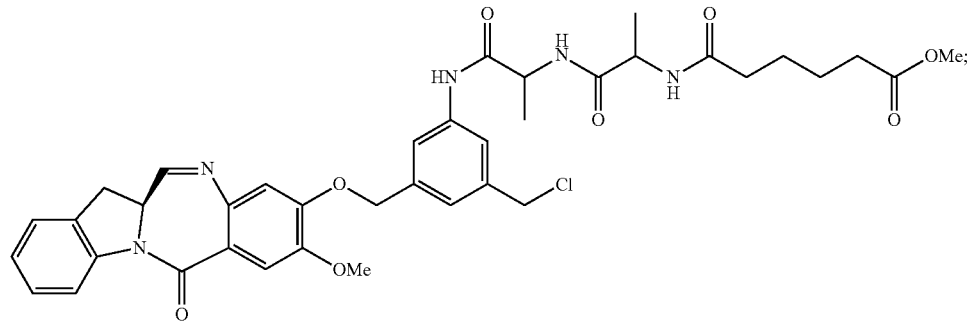
(VA')
3) reacting the compound of formula (VA') with an imine reducing agent to form a compound of formula to form a compound of formula (IIIA'):
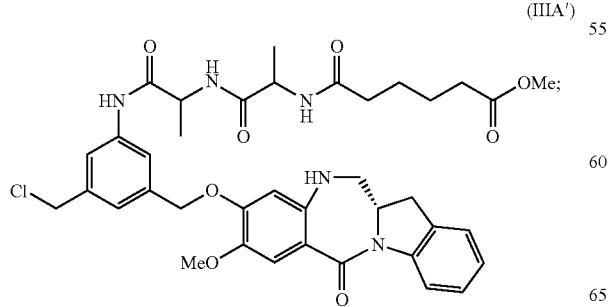
(IIIA')

and
4) reacting the compound of formula (IIIA') with a compound of formula (b):
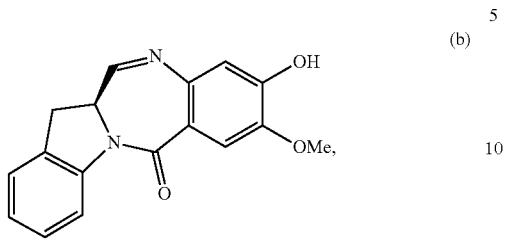
(b)
to form the compound of formula (IVA').
In a 6<sup>th</sup> specific embodiment, the present invention provides a method of preparing a compound of formula compound (IVA):
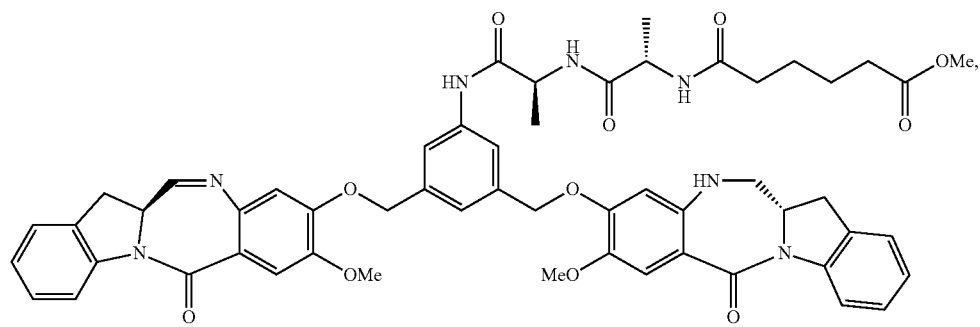 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
comprising the steps of:
1) reacting a compound of formula (IA):
(IA)
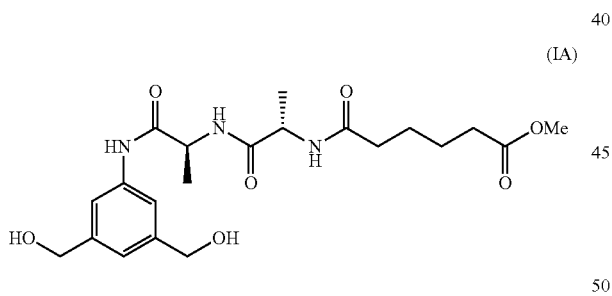
with cyanuric chloride to form a compound of formula (IIA):
(IIA)
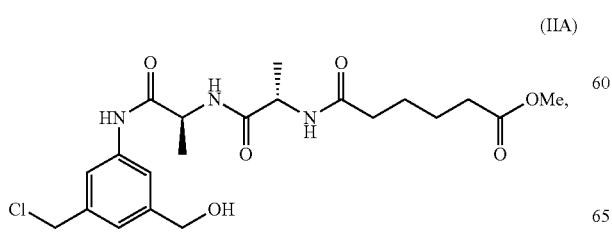

2) reacting the compound of formula (IIA) with a compound of formula (b):
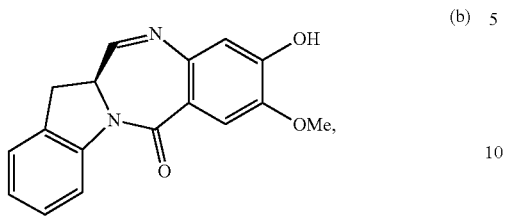 (b)
to form a compound of formula (VA):
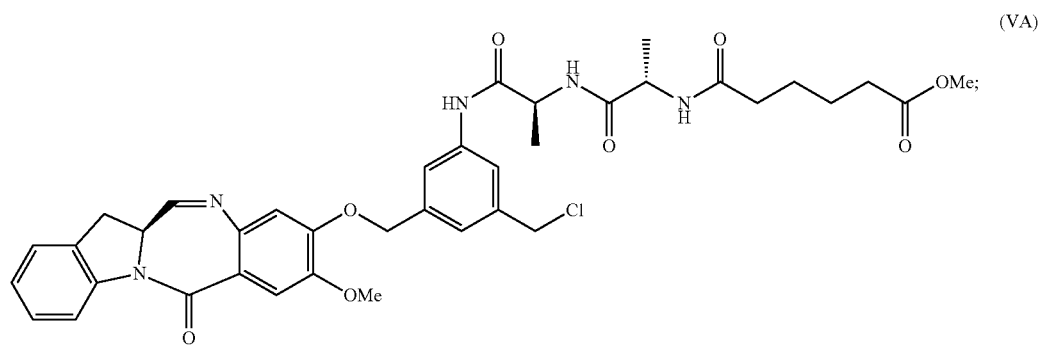 [SMILES: COC(=O)CCCCC(=O)N[C@@H](C)C(=O)N[C@@H](C)C(=O)Nc1cc(CCl)cc(COc2cc3c(cc2OC)C(=O)N2c4ccccc4C[C@H]2C=N3)c1] (VA)
3) reacting the compound of formula (VA) with an imine reducing agent to form a compound of formula to form a compound of formula (IIIA):
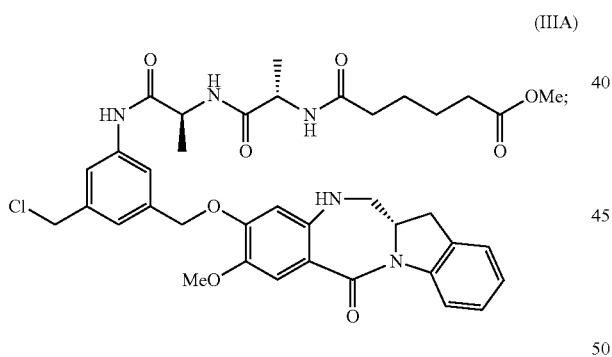 (IIIA)
and
4) reacting the compound of formula (IIIA) with a compound of formula (b):
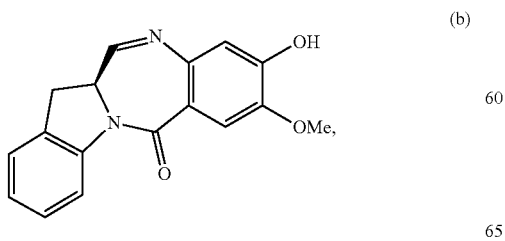 (b)
to form the compound of formula (IVA).

In a seventh embodiment, the present invention provides a method of preparing a compound of formula (IVA'):

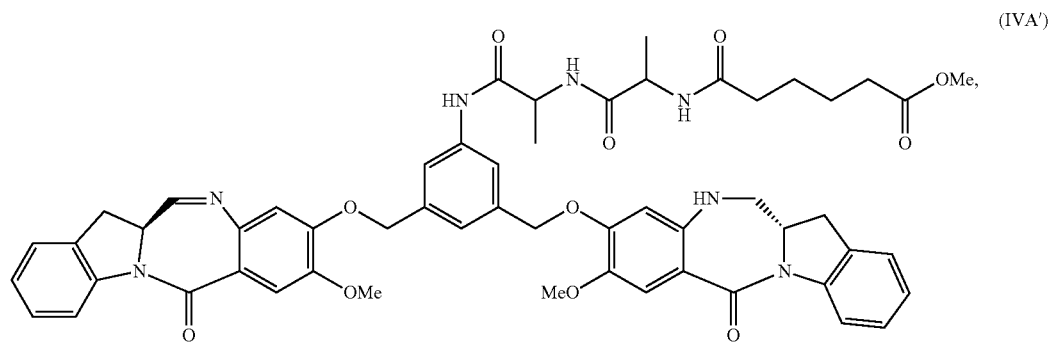 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA')

comprising the steps of:
1) reacting a compound of formula (IA'):

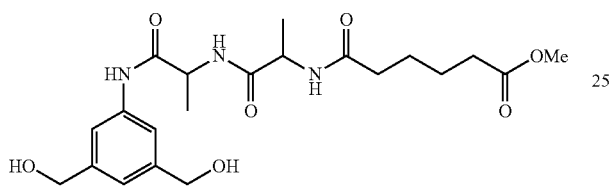
(IA')

with cyanuric chloride to form a compound of formula (IIA'):

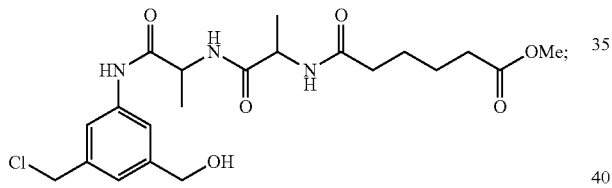
(IIA')

2) reacting the compound of formula (IIA') with a sulfonating agent to form a compound of formula (VIA'):

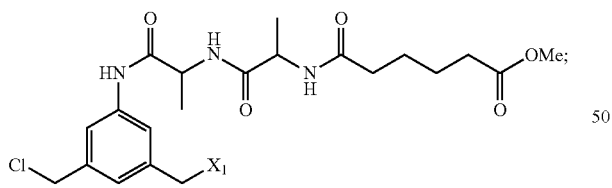
(VIA')

3) reacting the compound of formula (VIA') with a compound formula (b):

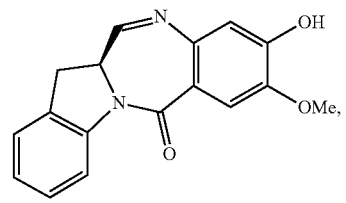
(b)

to form the compound of formula (VA'):
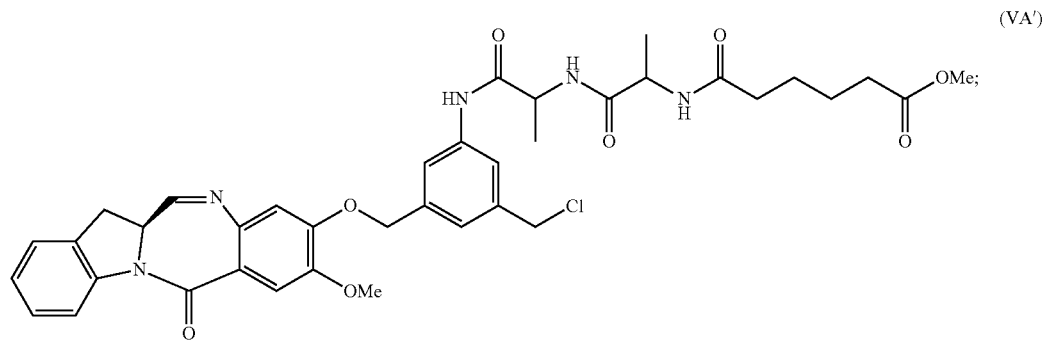 [SMILES: COC(=O)CCCCC(=O)NC(C)C(=O)NC(C)C(=O)Nc1cc(CCl)cc(COc2cc3c(cc2OC)C(=O)N2c4ccccc4C[C@H]2C=N3)c1]
(VA')
4) reacting the compound of formula (VA') with a compound of formula (a):
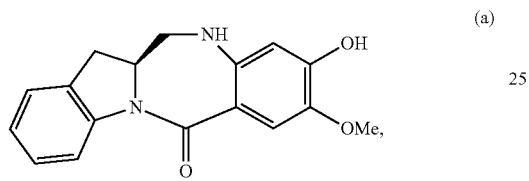
(a)
to form the compound of formula (IVA'), wherein $X_1$ is a sulfonate ester.
In a 7th specific embodiment, the present invention provides a method of preparing a compound of formula (IVA):
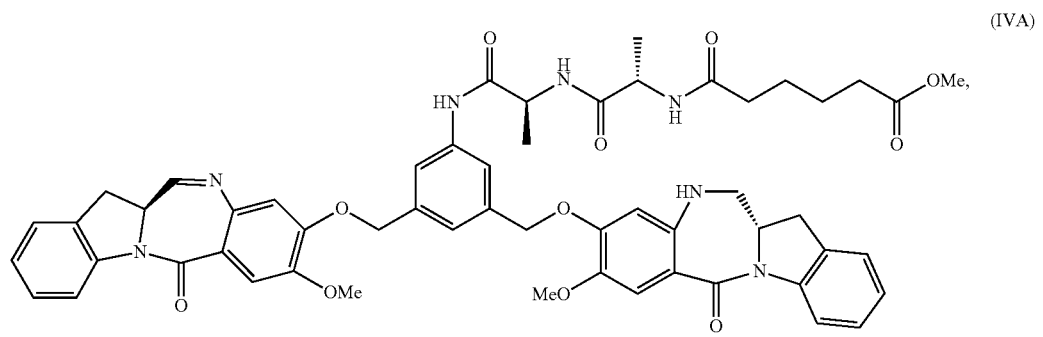 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
comprising the steps of:
1) reacting a compound of formula (IA):
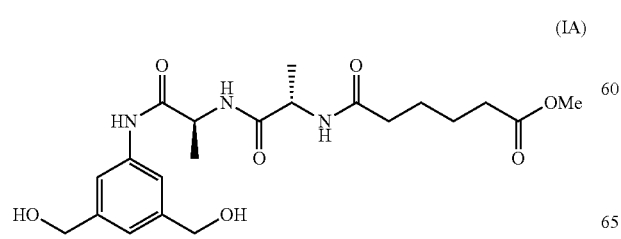
(IA)

with cyanuric chloride to form a compound of formula (IIA):

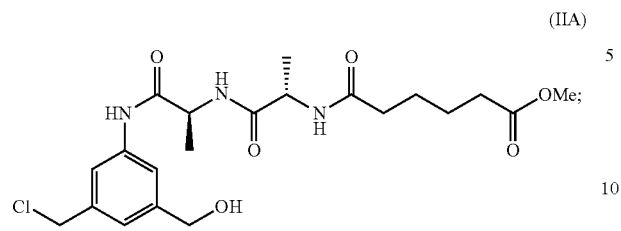

2) reacting the compound of formula (IIA) with a sulfonating agent to form a compound of formula (VIA):

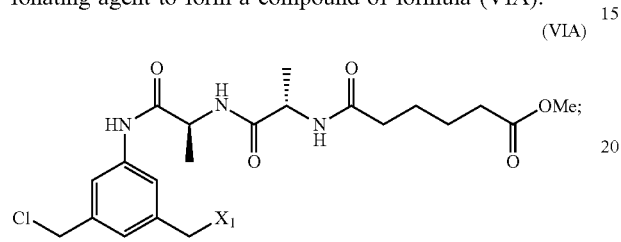

3) reacting the compound of formula (VIA) with a compound formula (b):

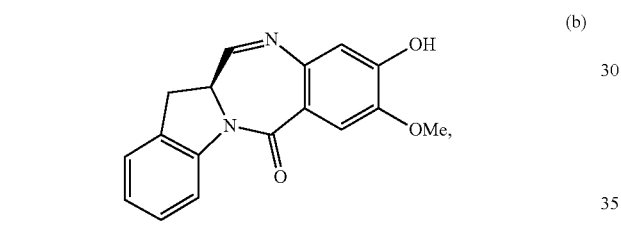

to form the compound of formula (VA):

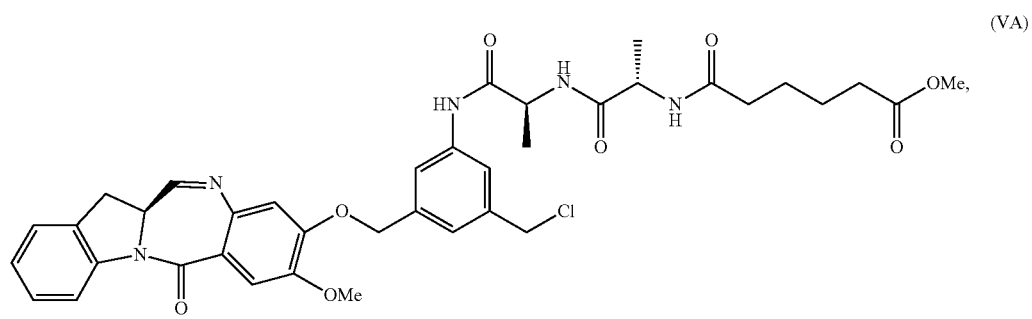 [SMILES: COC(=O)CCCCC(=O)N[C@@H](C)C(=O)N[C@@H](C)C(=O)Nc1cc(CCl)cc(COc2cc3c(cc2OC)C(=O)N2c4ccccc4C[C@H]2C=N3)c1]

4) reacting the compound of formula (VA) with a compound of formula (a):

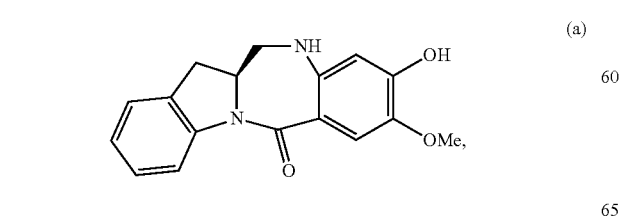

to form the compound of formula (IVA), wherein $X_1$ is a sulfonate ester.

In an eighth embodiment, the present invention provides a method of preparing a compound of formula (IVA'):

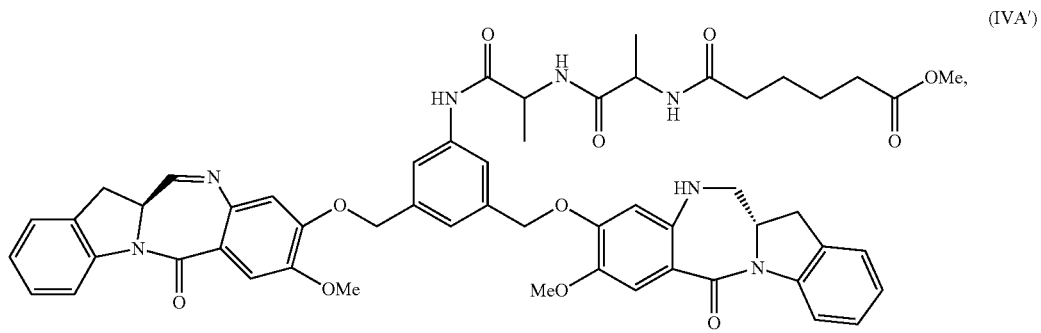 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

comprising the steps of:
1) reacting a compound of formula (IA'):

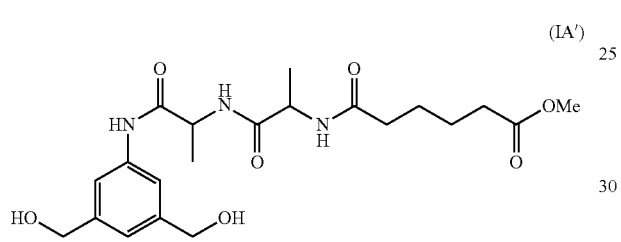

with cyanuric chloride to form a compound of formula (IIA'):

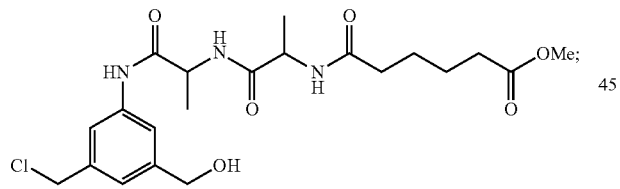

2) reacting the compound of formula (IIA') with a sulfonating agent to form a compound of formula (VIA'):

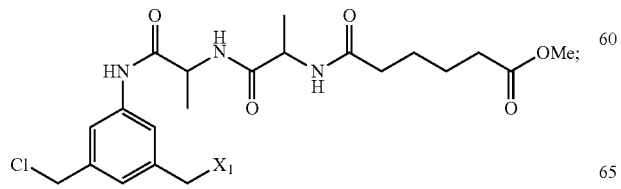

3) reacting the compound of formula (VIA') with a compound of formula (a):

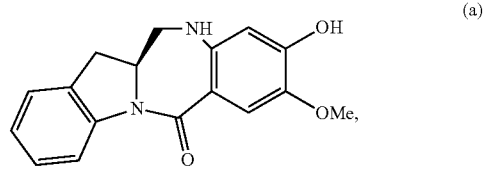 [SMILES: COc1cc2c(cc1O)NC[C@@H]1Cc3ccccc3N1C2=O]

to form a compound of formula (IIIA'):

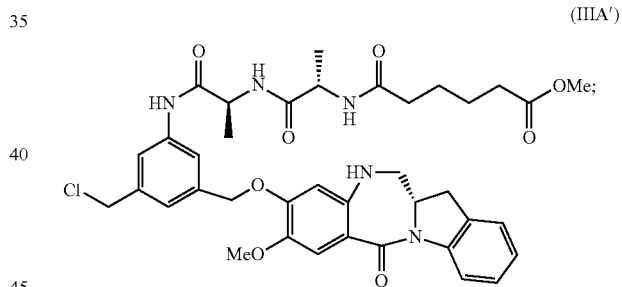

and
4) reacting the compound of formula (IIIA') with a compound of formula (b):

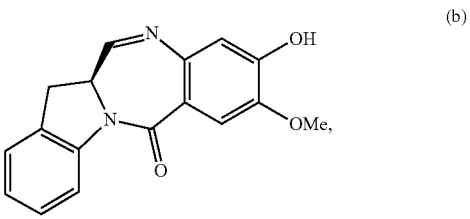 [SMILES: COc1cc2c(cc1O)N=C[C@@H]1Cc3ccccc3N1C2=O]

to form the compound of formula (IVA'), wherein $X_1$ is a sulfonate ester.

In an 8th specific embodiment, the present invention provides a method of preparing a compound of formula (IVA):

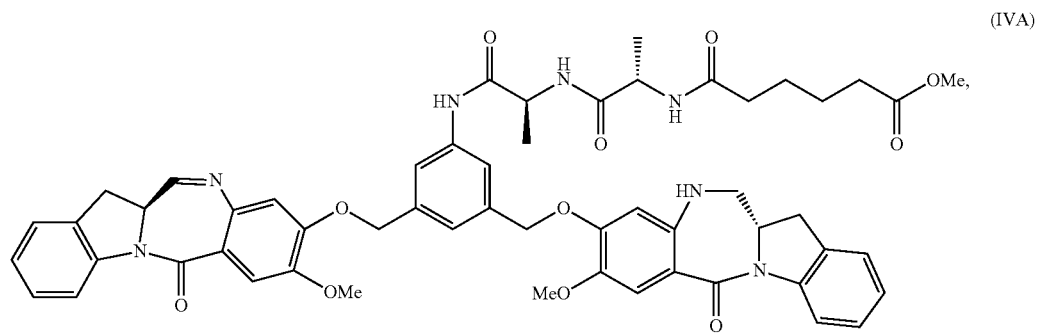 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

comprising the steps of:

1) reacting a compound of formula (IA):

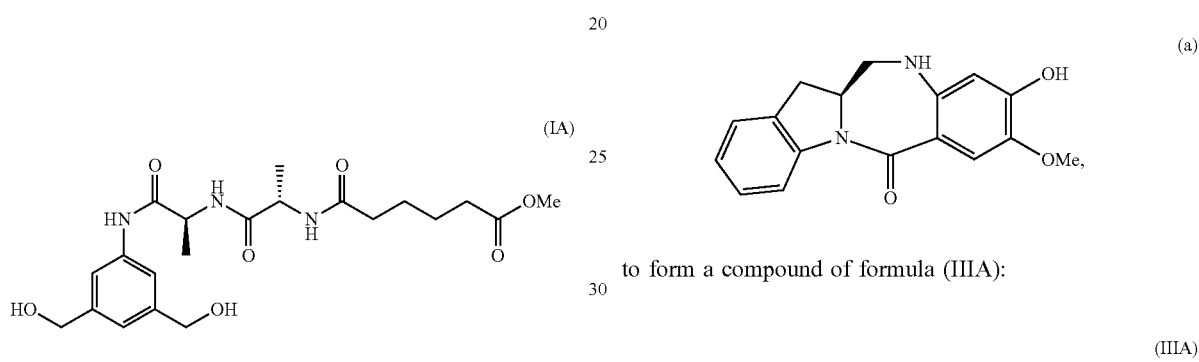

with cyanuric chloride to form a compound of formula (IIA):

2) reacting the compound of formula (IIA) with a sulfonating agent to form a compound of formula (VIA):

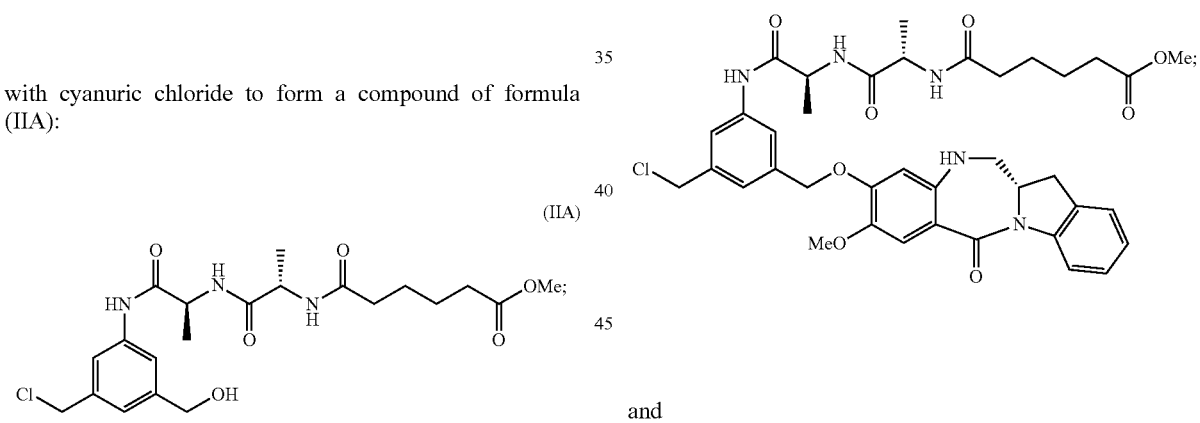

3) reacting the compound of formula (VIA) with a compound of formula (a):

to form a compound of formula (IIIA):

and 4) reacting the compound of formula (IIIA) with a compound of formula (b):

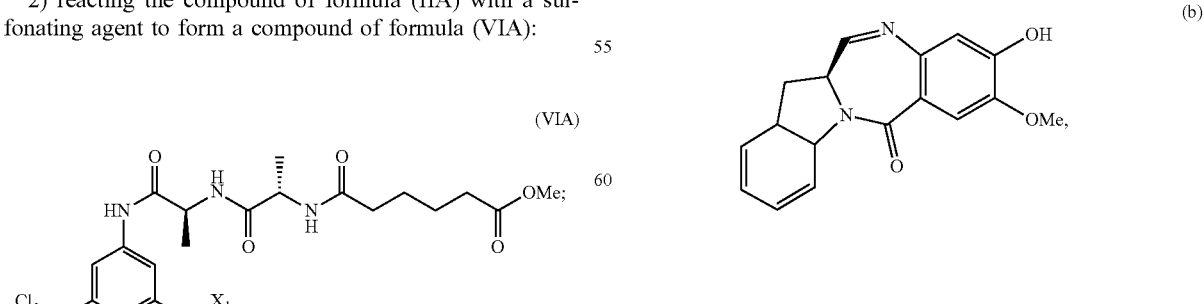

to form the compound of formula (IVA), wherein $X_1$ is a sulfonate ester.

In a ninth embodiment, the present invention provides a method of preparing a compound of formula (IVA'):
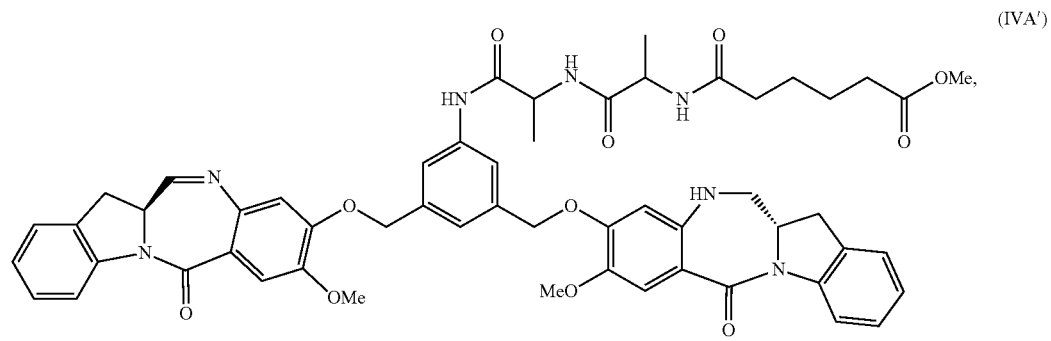 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA')
comprising the steps of:
1) reacting a compound of formula (IA'):
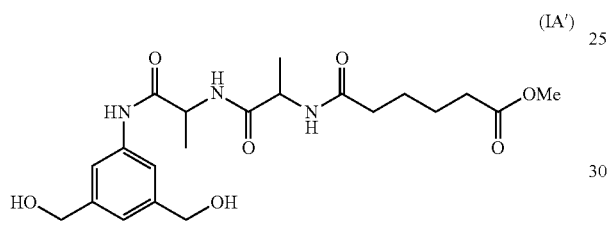
(IA')
with cyanuric chloride to form a compound of formula (IIA'):
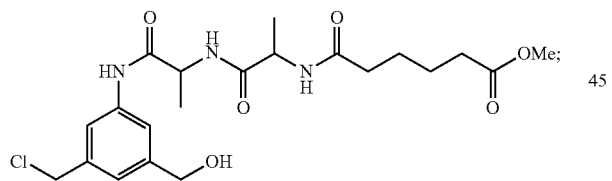
(IIA')
2) reacting the compound of formula (IIA') with a sulfonating agent to form a compound of formula (VIA'):
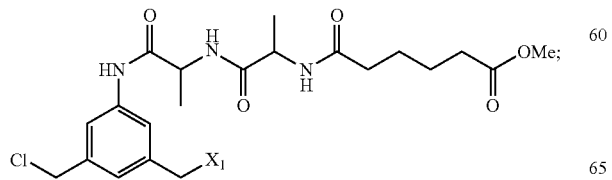
(VIA')

3) reacting the compound of formula (VIA') with a compound of formula (b):
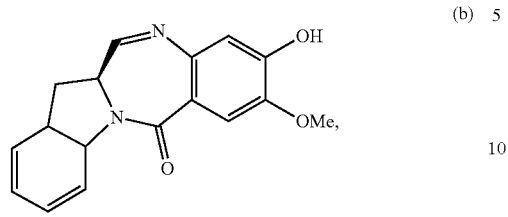
(b)
to form the compound of formula (VA'):
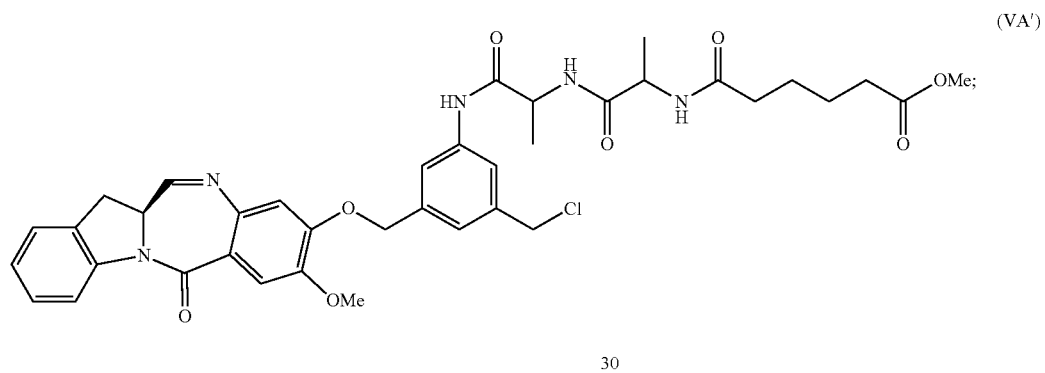
(VA')
4) reacting the compound of formula (VA') with an imine reducing agent to form a compound of formula (IIIA'):
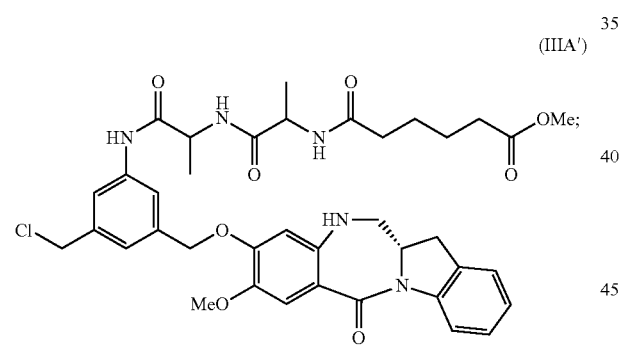
(IIIA')
and
5) reacting the compound of formula (IIIA') with a compound of formula (b):
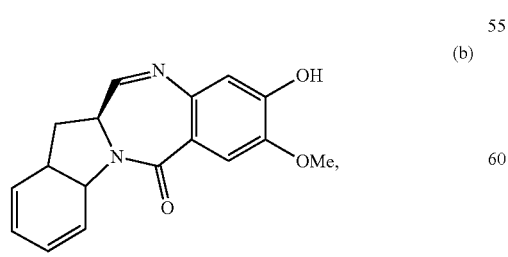
(b)
to form the compound of formula (IVA'), wherein $X_1$ is a sulfonate ester.

In a 9th specific embodiment, the present invention provides a method of preparing a compound of formula (IVA):
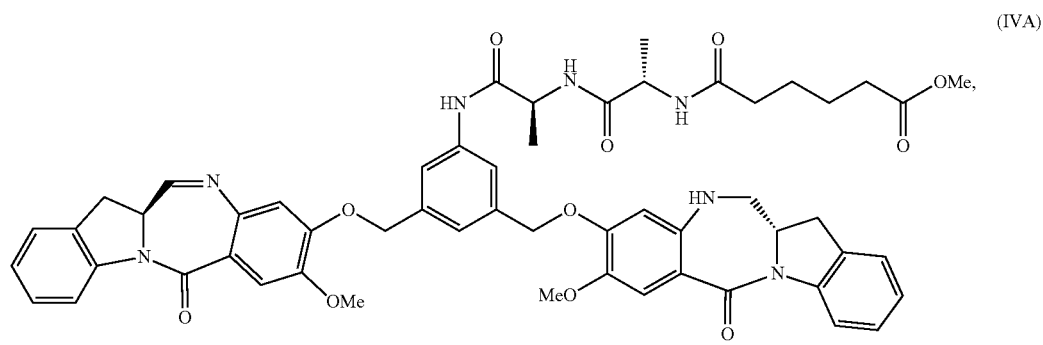 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
comprising the steps of:
1) reacting a compound of formula (IA):
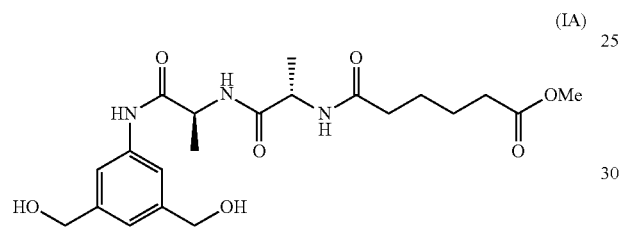
(IA)
with cyanuric chloride to form a compound of formula (IIA):
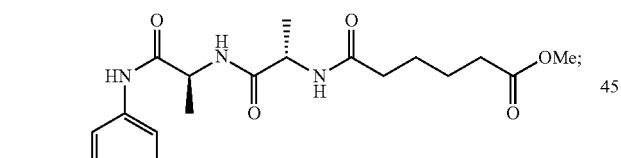
(IIA)
2) reacting the compound of formula (IIA) with a sulfonating agent to form a compound of formula (VIA):
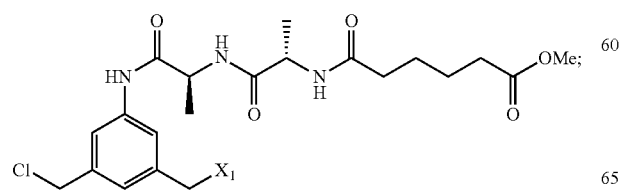
(VIA)

3) reacting the compound of formula (VIA) with a compound of formula (b):
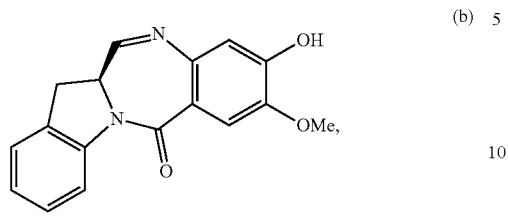
(b)
to form the compound of formula (VA):
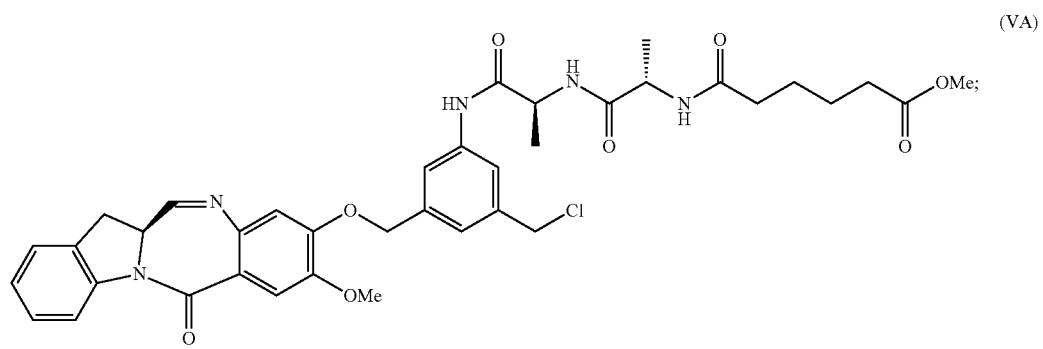 [SMILES: COC(=O)CCCCC(=O)N[C@@H](C)C(=O)N[C@@H](C)C(=O)Nc1cc(CCl)cc(COc2cc3c(cc2OC)C(=O)N2c4ccccc4C[C@H]2C=N3)c1]
(VA)
4) reacting the compound of formula (VA) with an imine reducing agent to form a compound of formula (IIIA):
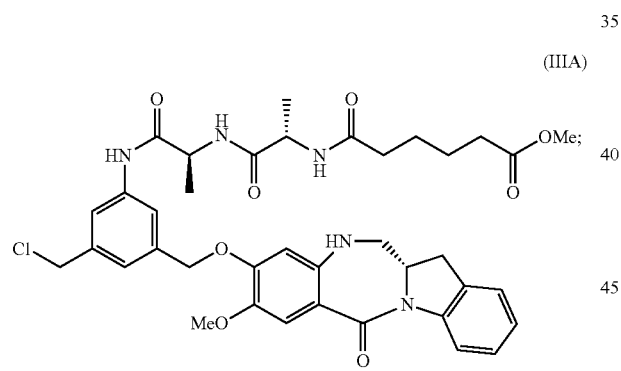
(IIIA)
and
5) reacting the compound of formula (IIIA) with a compound of formula (b):
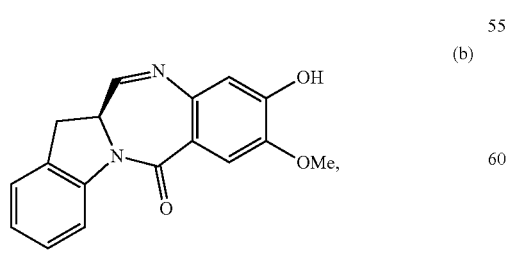
(b)
to form the compound of formula (IVA), wherein $X_1$ is a sulfonate ester.

In a tenth embodiment, the present invention provides a method of preparing a compound of formula (IVA'):
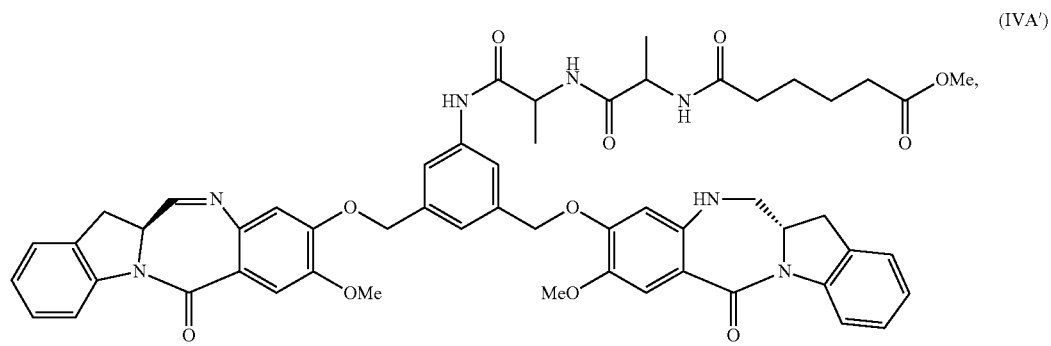 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
comprising the steps of:
1) reacting a compound of formula (IA'):
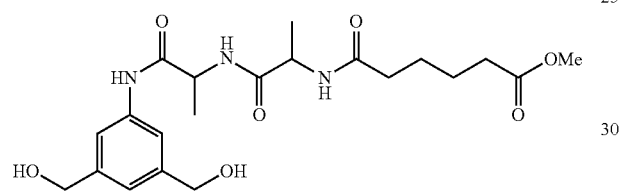
with cyanuric chloride to form a compound of formula (IIA'):
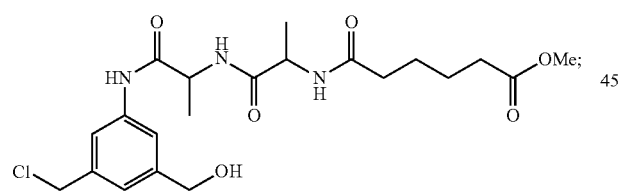
2) reacting the compound of formula (IIA') with a compound of formula (b):
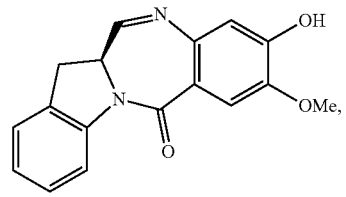

to form the compound of formula (VIIA'):

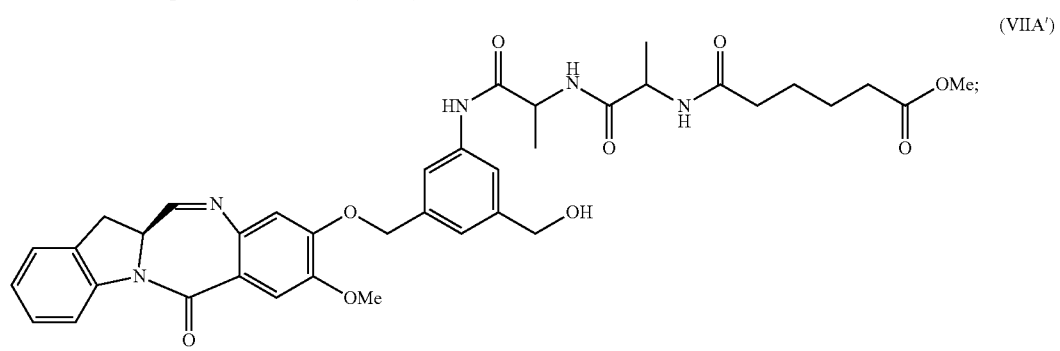 [SMILES: COC(=O)CCCCC(=O)NC(C)C(=O)NC(C)C(=O)Nc1cc(CO)cc(COc2cc3c(cc2OC)C(=O)N2c4ccccc4C[C@H]2C=N3)c1]

(VIIA')

3) reacting the compound of formula (VIIA') with a sulfonating agent to form a compound of formula (VIIIA'):

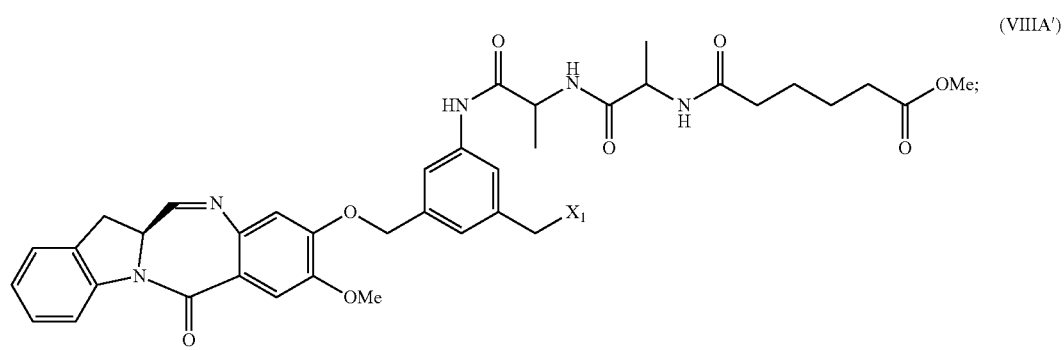

(VIIIA')

4) reacting the compound of formula (VIIIA') with a compound of formula (a):

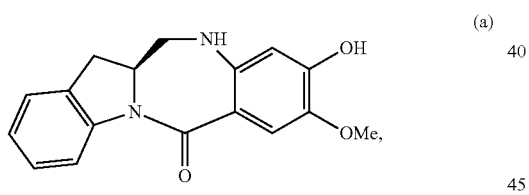

(a)

to form the compound of formula (IVA'), wherein $X_1$ is a sulfonate ester.

In a 10<sup>th</sup> specific embodiment, the present invention provides a method of preparing a compound of formula (IVA):

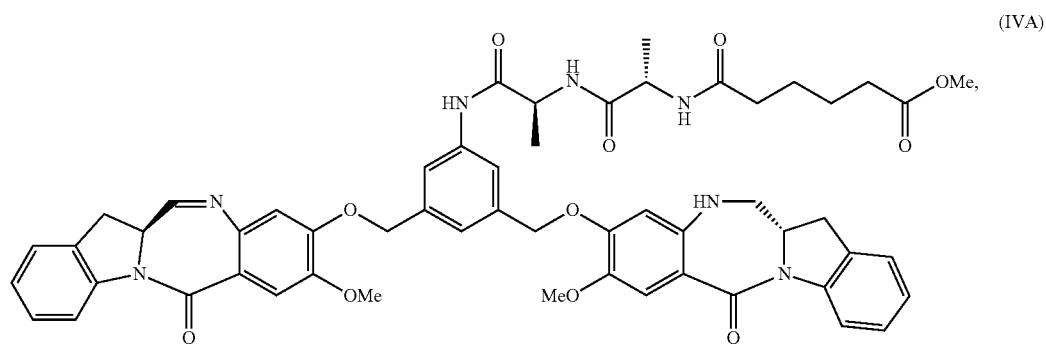 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

(IVA)

comprising the steps of:
1) reacting a compound of formula (IA):
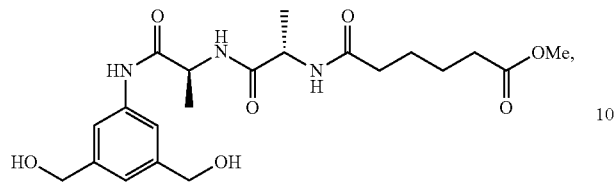
(IA)
with cyanuric chloride to form a compound of formula (IIA):
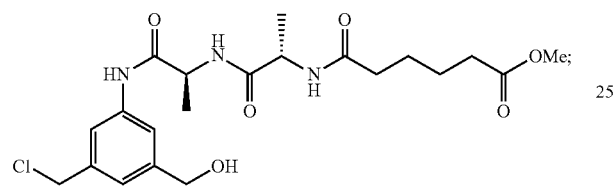
(IIA)
2) reacting the compound of formula (IIA) with a compound of formula (b):
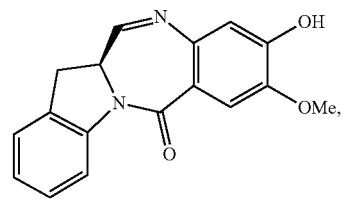
(b)
to form the compound of formula (VIIA):
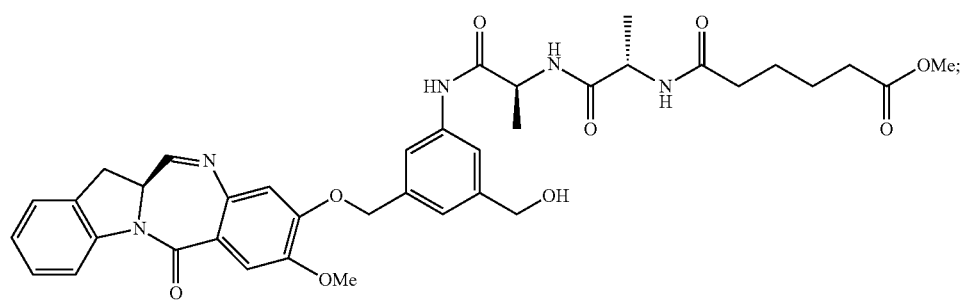
(VIIA)

3) reacting the compound of formula (VIIA) with a sulfonating agent to form a compound of formula (VIIIA):

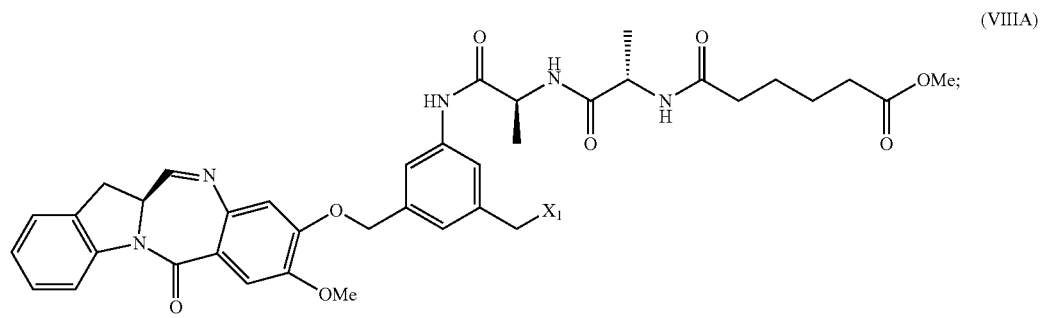
(VIIIA)

4) reacting the compound of formula (VIIIA) with a compound of formula (a):

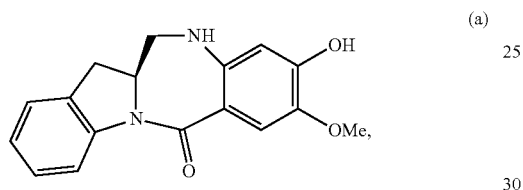
(a)

to form the compound of formula (IVA), wherein $X_1$ is a sulfonate ester.

In a eleventh embodiment, the present invention provides a method of preparing a compound of formula (IVA'):

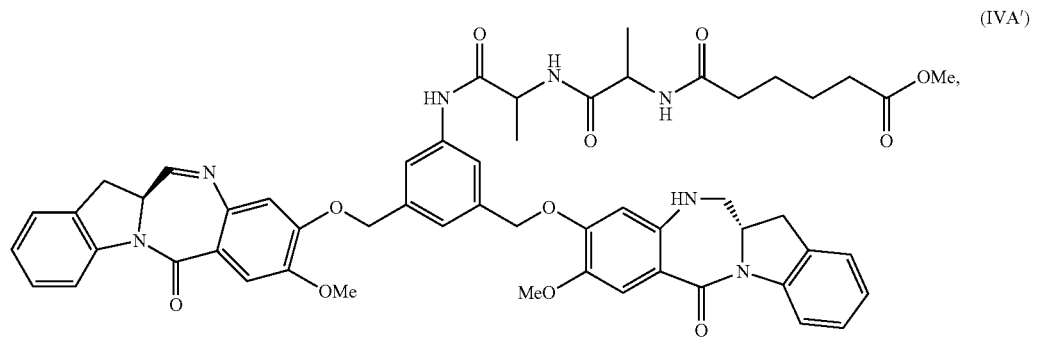 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA')

comprising the steps of:
1) reacting a compound of formula (IA'):

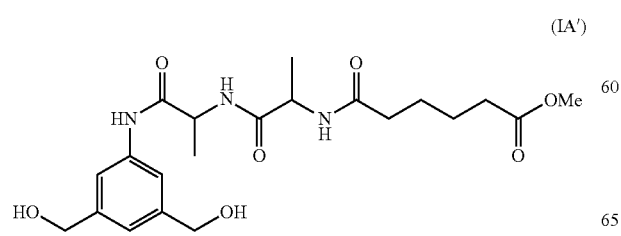
(IA')

with cyanuric chloride to form a compound of formula (IIA'):

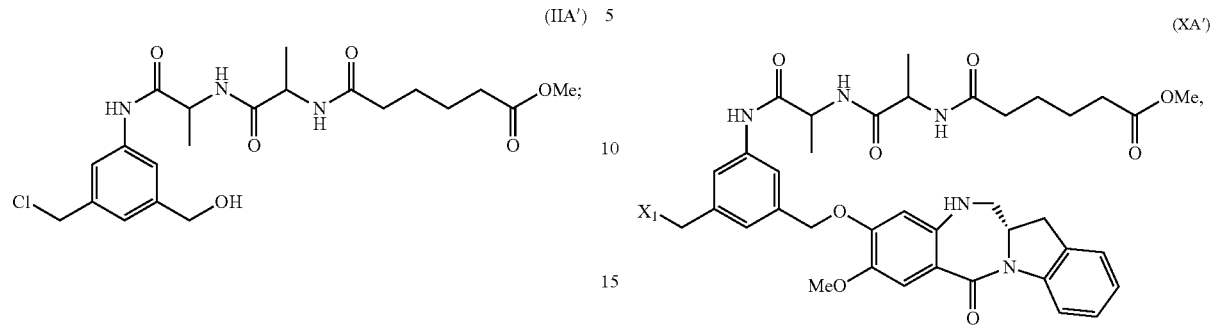

2) reacting the compound of formula (IIA') with a compound of formula (a):

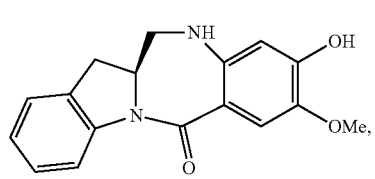

to form a compound of formula (IXA'):

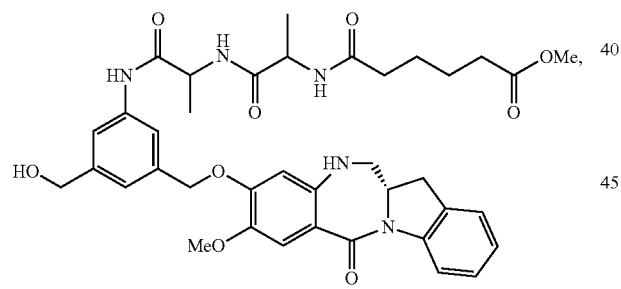

3) reacting the compound of formula (IXA') with a sulfonating agent to form a compound of formula (XA'):

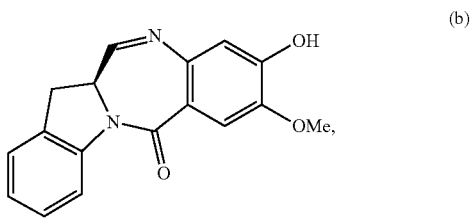 [SMILES: COc1cc2c(cc1O)N=C[C@@H]1Cc3ccccc3N1C2=O]

4) reacting the compound of formula (XA') with a compound of formula (b):

(b)

to form the compound of formula (IVA'), wherein $X_1$ is a sulfonate ester.

In a 11$^{th}$ specific embodiment, the present invention provides a method of preparing a compound of formula (IVA):

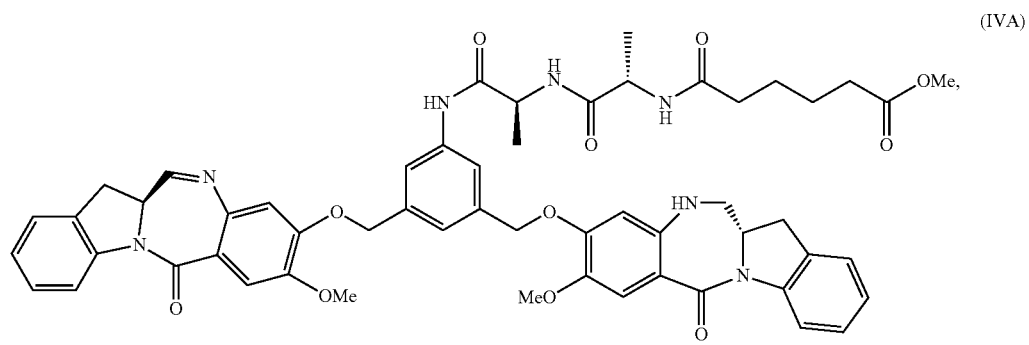 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

comprising the steps of:

1) reacting a compound of formula (IA):

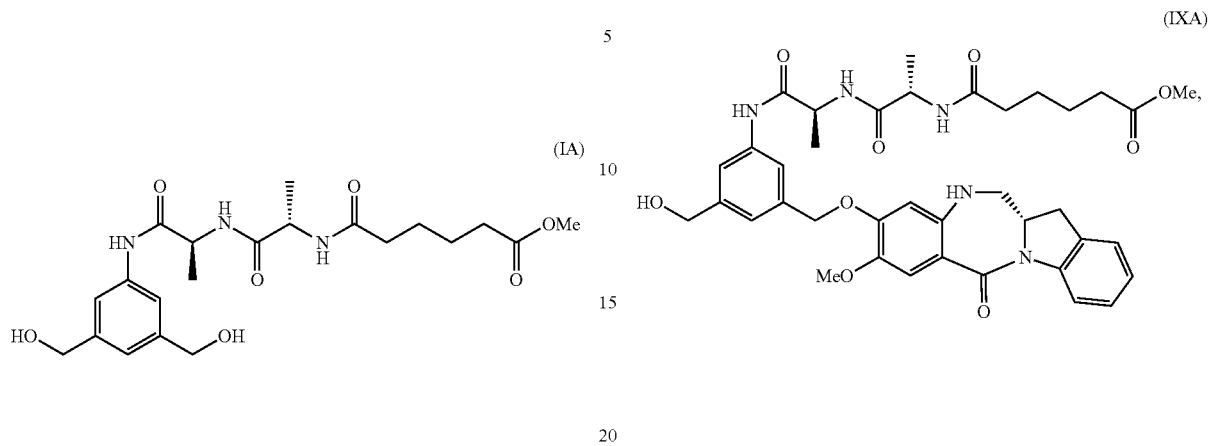

(IA)

with cyanuric chloride to form a compound of formula (IIA):

(IIA)

2) reacting the compound of formula (IIA) with a compound of formula (a):

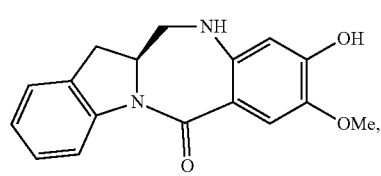

(a)

to form a compound of formula (IXA):

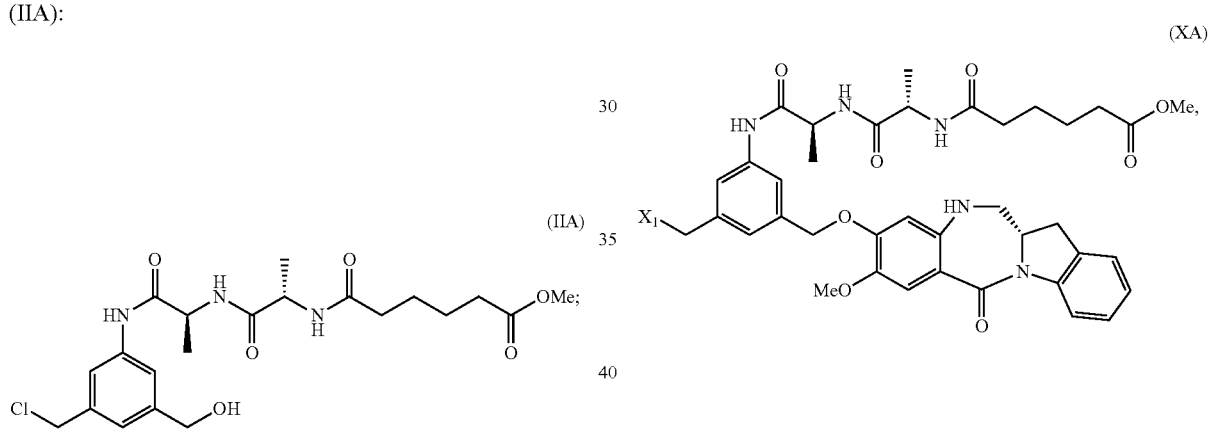

(IXA)

3) reacting the compound of formula (IXA) with a sulfonating agent to form a compound of formula (XA):

(XA)

4) reacting the compound of formula (XA) with a compound of formula (b):

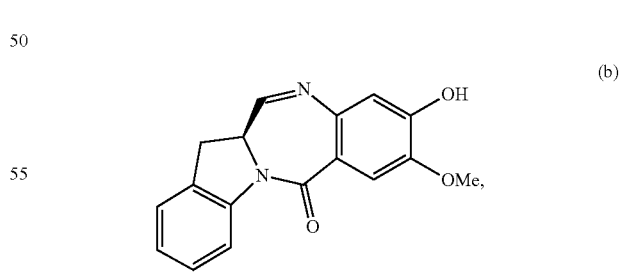

(b)

to form the compound of formula (IVA), wherein $X_1$ is a sulfonate ester.

In a twelfth embodiment, the present invention provides a method of preparing a compound of formula (IVA'):

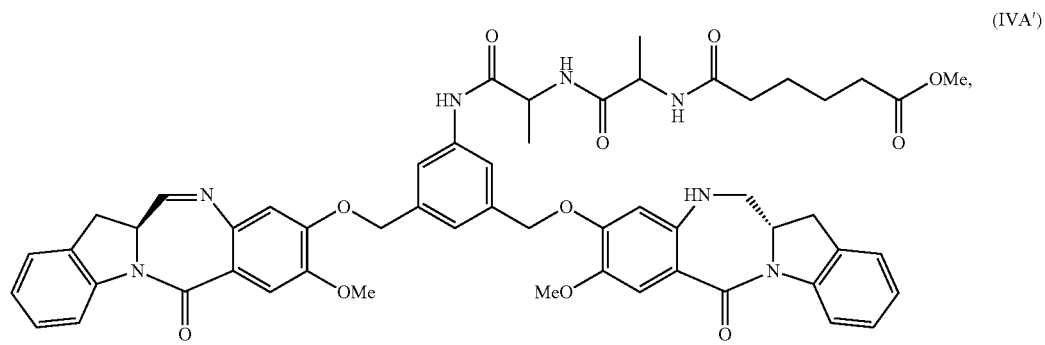 [SMILES: COC(=O)CCCCC(=O)NC(C)C(=O)NC(C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
comprising the steps of:
1) reacting a compound of formula (IA'):
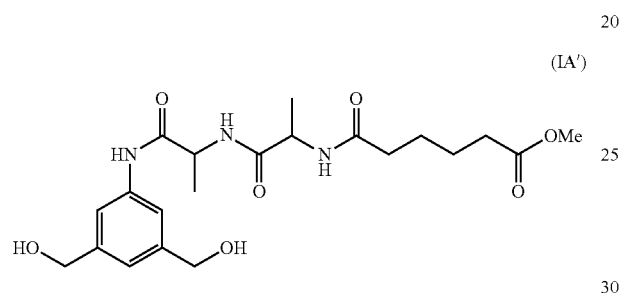
with cyanuric chloride to form a compound of formula (IIA'):
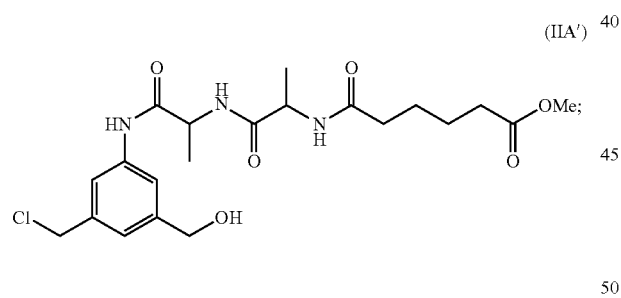
2) reacting the compound of formula (IIA') with a compound of formula (b):
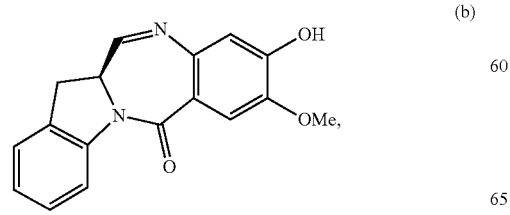

to form the compound of formula (VIIA'):

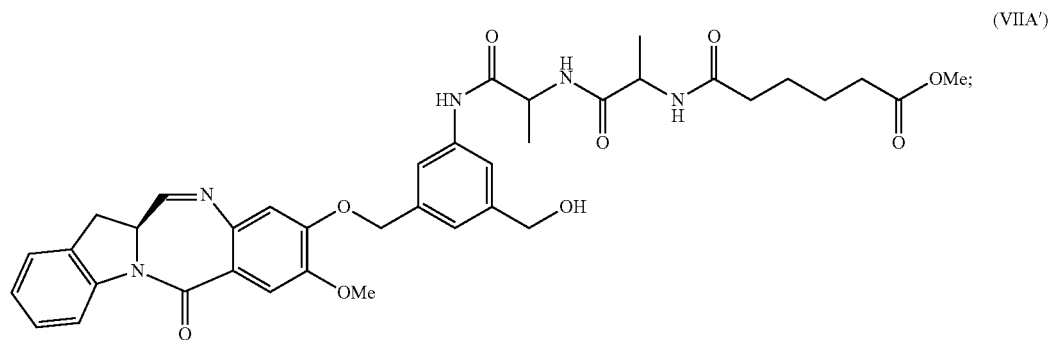 [SMILES: COC(=O)CCCCC(=O)NC(C)C(=O)NC(C)C(=O)Nc1cc(CO)cc(COc2cc3c(cc2OC)C(=O)N2c4ccccc4C[C@H]2C=N3)c1]

3) reacting the compound of formula (VIIA') with an imine reducing agent to form a compound of formula (IXA'):

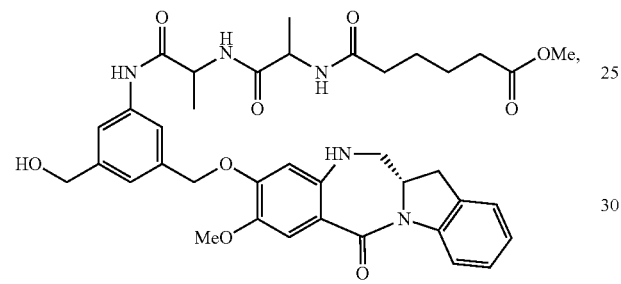

4) reacting the compound of formula (IXA') with a sulfonating agent to form a compound of formula (XA'):

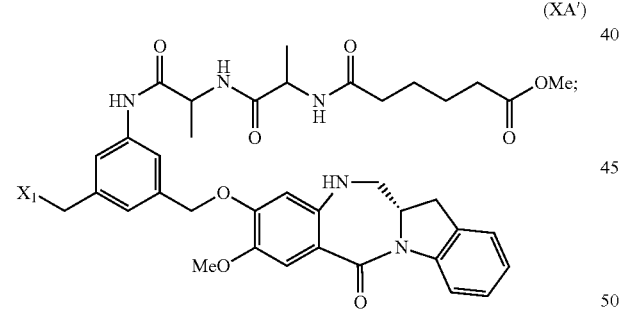

5) reacting the compound of formula (XA') with a compound of formula (b):

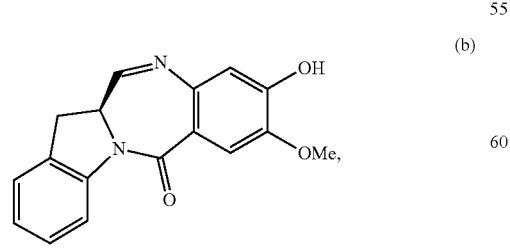

to form the compound of formula (IVA'), wherein $X_1$ is a sulfonate ester.

In a 12th specific embodiment, the present invention provides a method of preparing a compound of formula (IVA'):
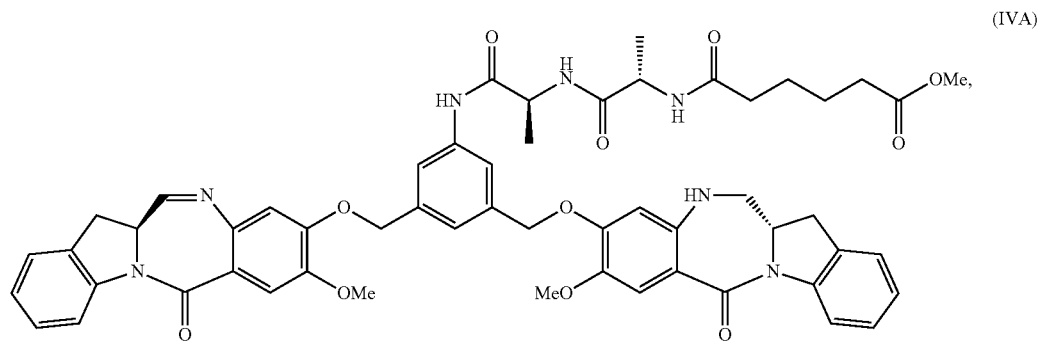 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
comprising the steps of:
1) reacting a compound of formula (IA):
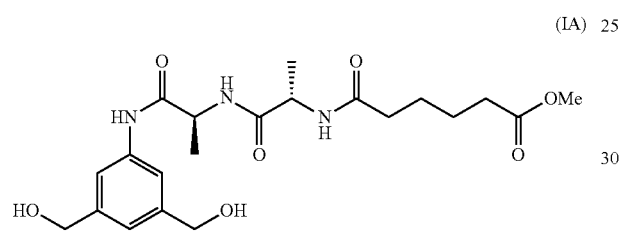
(IA)
with cyanuric chloride to form a compound of formula (IIA):
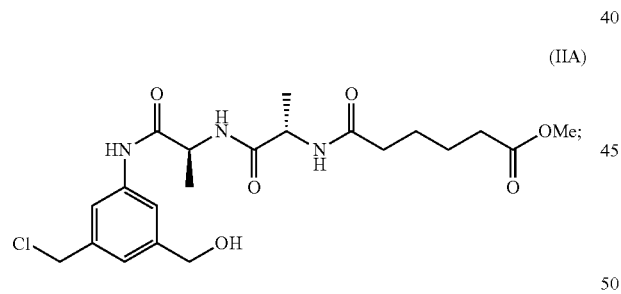
(IIA)
2) reacting the compound of formula (IIA) with a compound of formula (b):
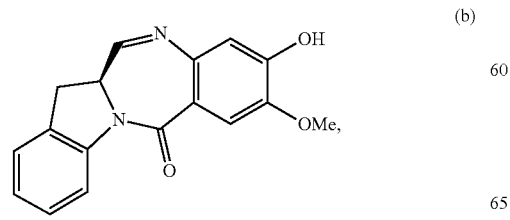
(b)

to form the compound of formula (VIIA):

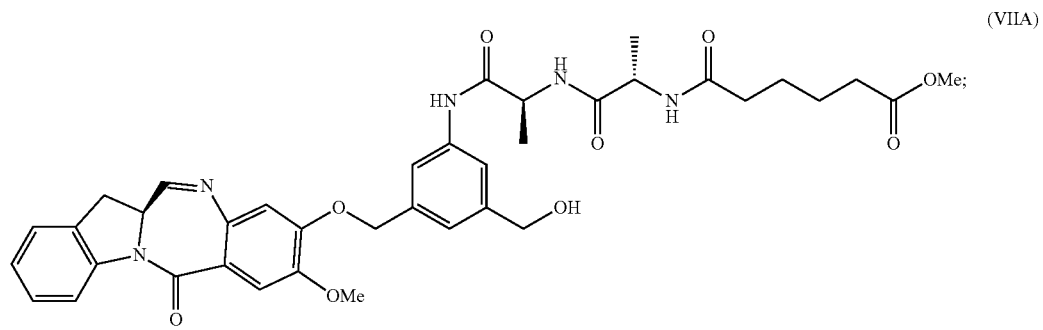 [SMILES: COC(=O)CCCCC(=O)N[C@@H](C)C(=O)N[C@@H](C)C(=O)Nc1cc(CO)cc(COc2cc3c(cc2OC)C(=O)N2c4ccccc4C[C@H]2C=N3)c1]

3) reacting the compound of formula (VIIA) with an imine reducing agent to form a compound of formula (IXA):

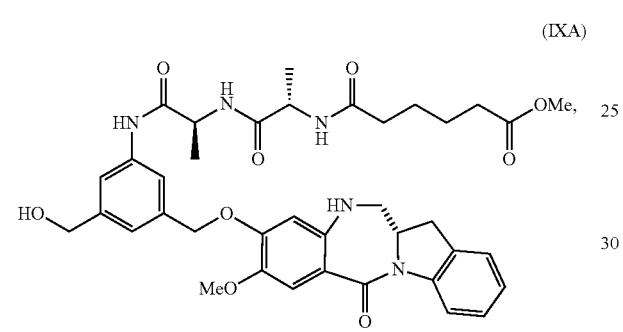

4) reacting the compound of formula (IXA) with a sulfonating agent to form a compound of formula (XA):

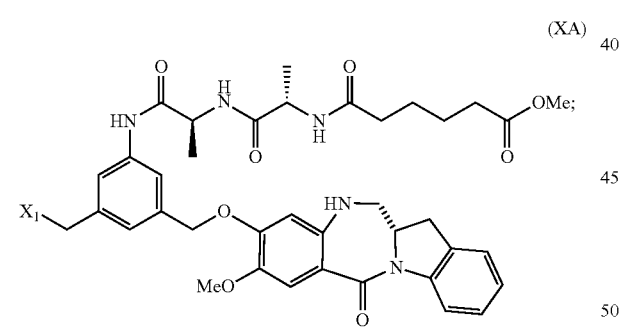

5) reacting the compound of formula (XA) with a compound of formula (b):

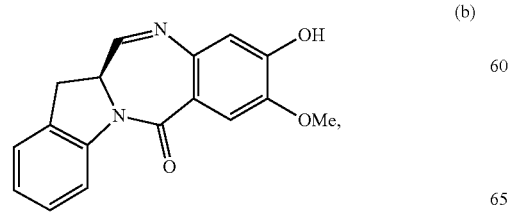

to form the compound of formula (IVA'), wherein $X_1$ is a sulfonate ester.

In a thirteenth embodiment, the present invention provides a method of preparing a compound of formula (IIB):

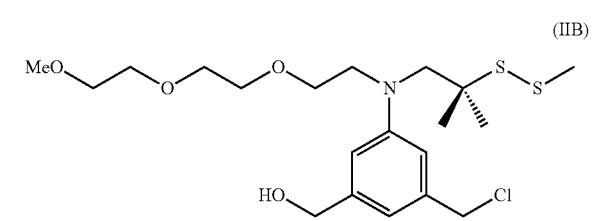

comprising reacting a compound of formula (IB):

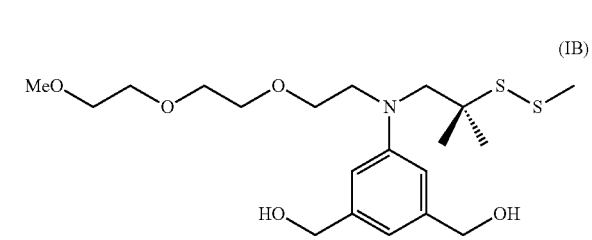

with cyanuric chloride to form the compound of formula (IIB).

In a fourteenth embodiment, the method of the thirteenth embodiment further comprises reacting the compound of formula (IIB) with a compound of formula (a):

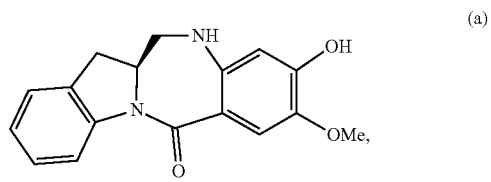 [SMILES: COc1cc2c(cc1O)NC[C@@H]1Cc3ccccc3N1C2=O]

to form a compound of formula (IIIB):
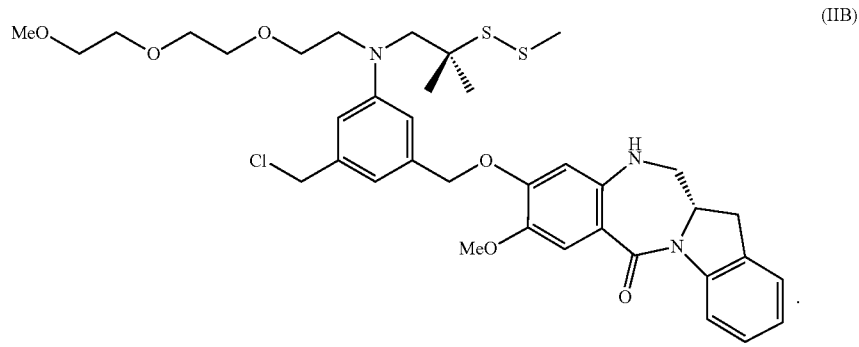
In a fifteenth embodiment, the method of the fourteenth embodiment further comprises reacting the compound of formula (IIIB) with a compound of formula (b):
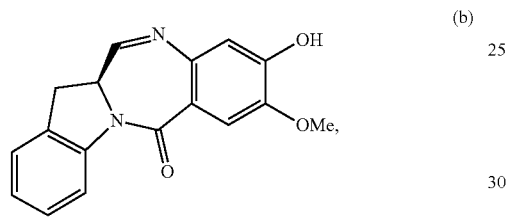
to form a compound of formula (IVB):
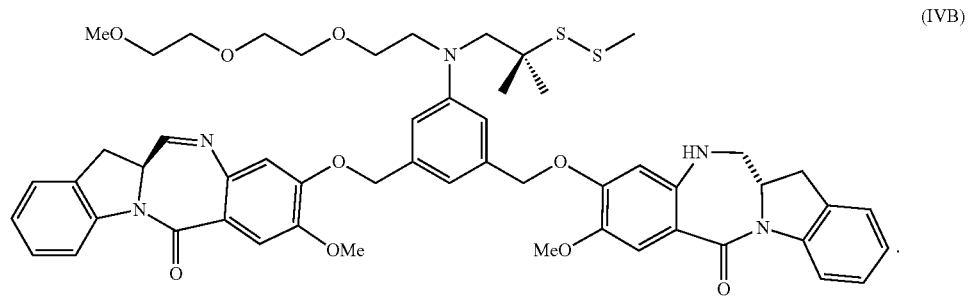
In a sixteenth embodiment, the present invention provides a method of preparing a compound formula (IVB):
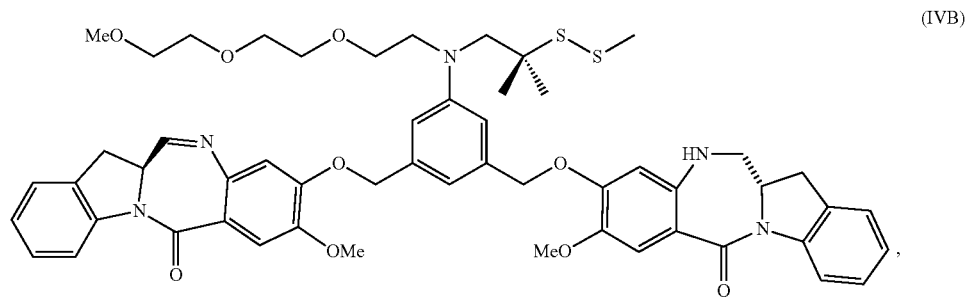

comprising the steps of:
1) reacting a compound of formula (IB):
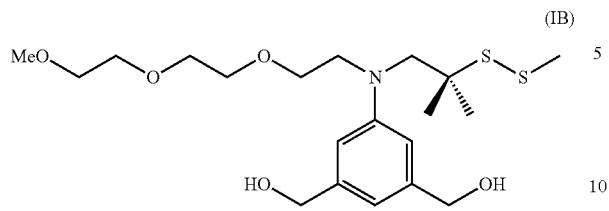
with cyanuric chloride to form a compound of formula (IIB):
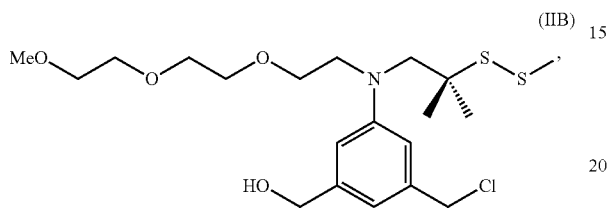
2) reacting the compound of formula (IIB) with a compound of formula (a):
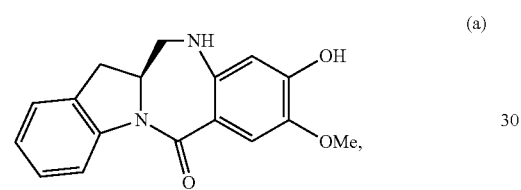
to form a compound of formula (IIIB):
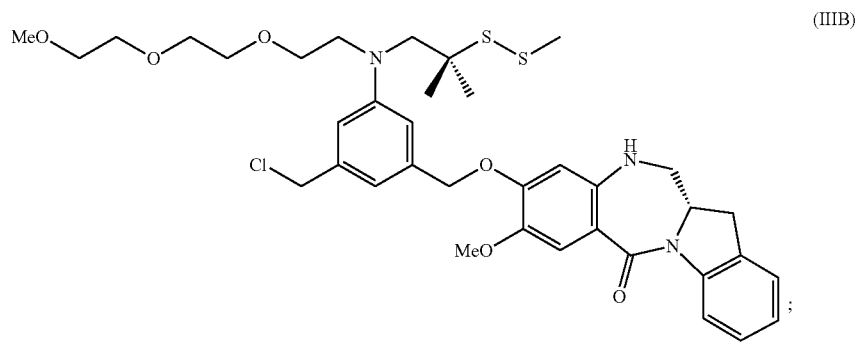
and
3) reacting the compound of formula (IIIB) with a compound of formula (b):
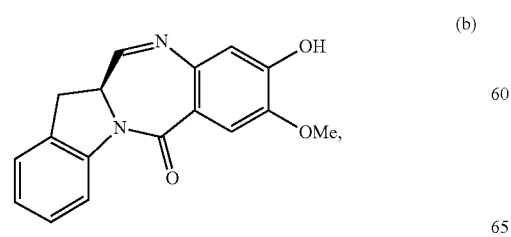
to form the compound of formula (IVB).

In a seventeenth embodiment, the present invention provides a method of preparing a compound of formula (IVB):

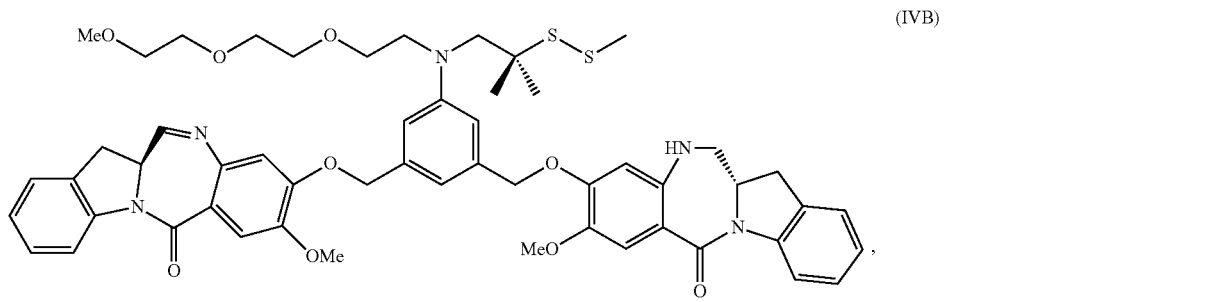

(IVB)

comprising the steps of:
1) reacting a compound of formula (IB):

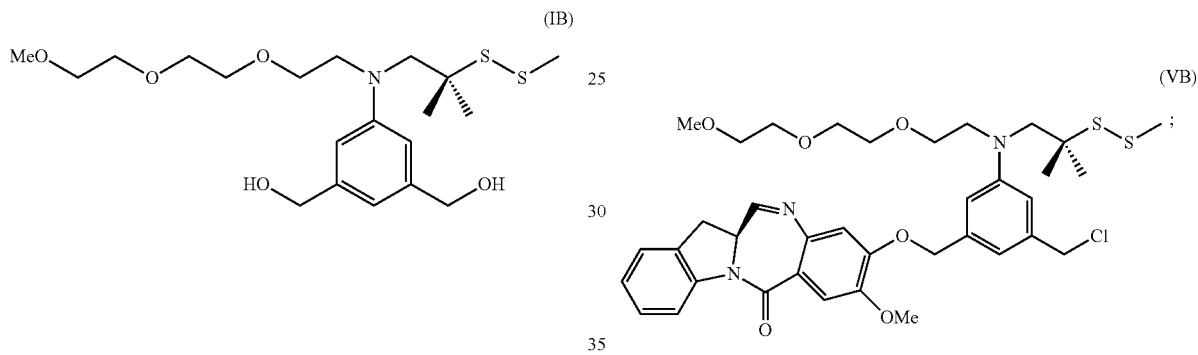

(IB)

with cyanuric chloride to form a compound of formula (IIB):

(IIB)

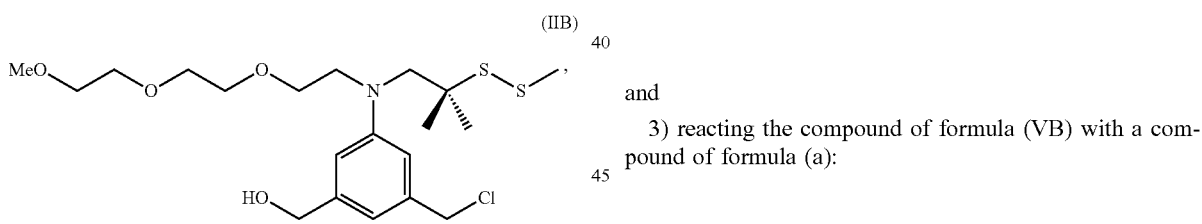

2) reacting the compound of formula (IIB) with a compound of formula (b):

(b)

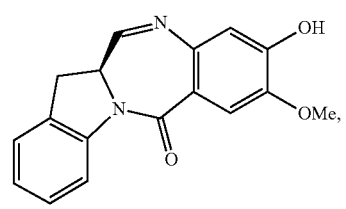

to form a compound of formula (VB):

(VB)

and 3) reacting the compound of formula (VB) with a compound of formula (a):

(a)

to form the compound of formula (IVB).

In an eighteenth embodiment, the present invention provides a method of preparing a compound of formula (IVB):

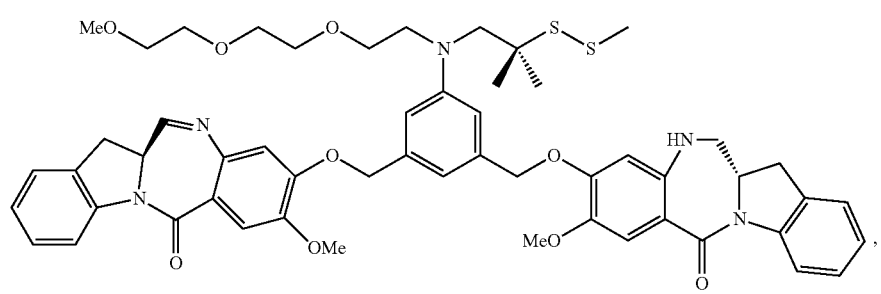
(IVB)
comprising the steps of:
1) reacting a compound of formula (IB):
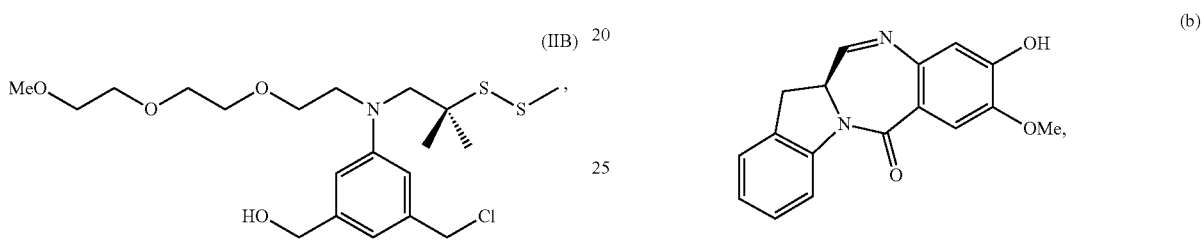
with cyanuric chloride to form a compound of formula (IIB):
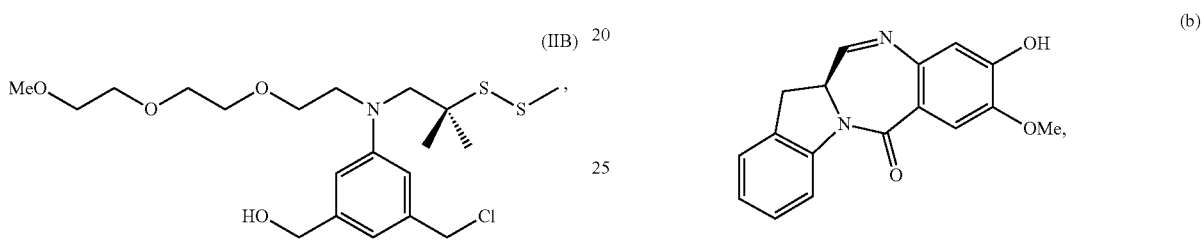
2) reacting the compound of formula (IIB) with a compound of formula (b):
(b)
to form a compound of formula (VB):
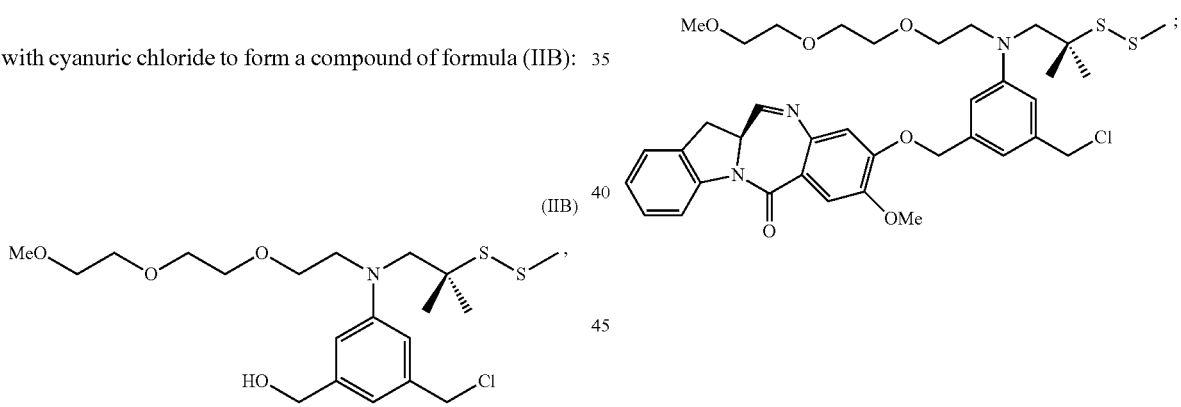
(VB)
3) reacting the compound of formula (VB) with an imine reducing agent to form a compound of formula (IIIB):
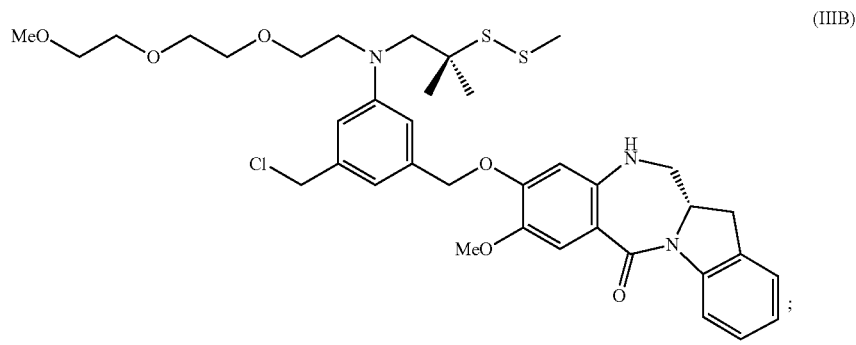
(IIIB)

and 4) reacting the compound of formula (IIIB) with a compound of formula (b):

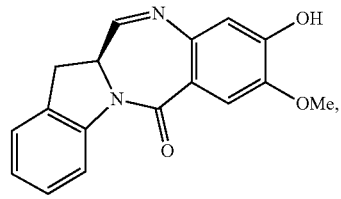

to form the compound of formula (IVB).

In a nineteenth embodiment, the present invention provides a method of preparing a compound of formula (IVB) comprising the steps of:

1) reacting a compound of formula (IB):

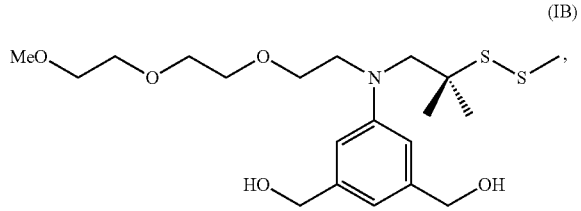

with cyanuric chloride to form a compound of formula (IIB):

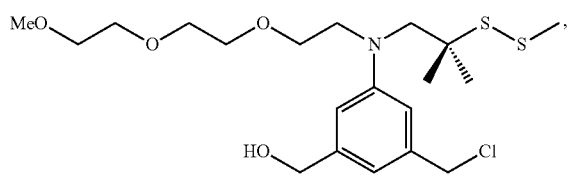

2) reacting the compound of formula (IIB) with sulfonating agent to form a compound of formula (VIB):

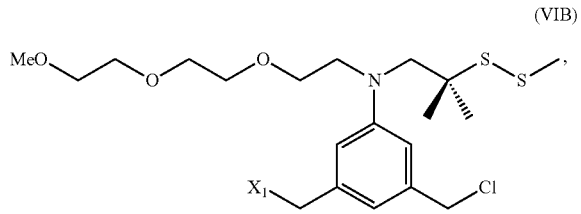

3) reacting the compound of formula (VIB) with a compound of formula (b):

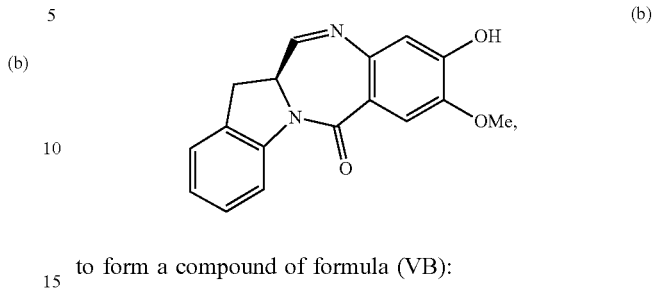

to form a compound of formula (VB):

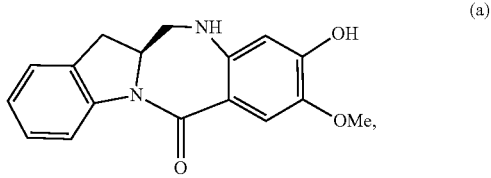 [SMILES: COc1cc2c(cc1O)NC[C@@H]1Cc3ccccc3N1C2=O]

4) reacting the compound of formula (VB) with a compound of formula (a):

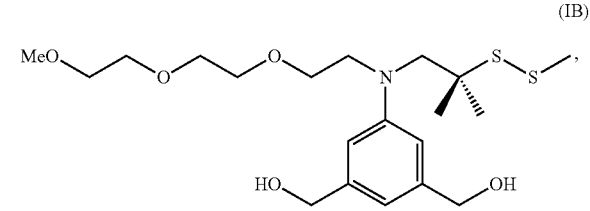

to form the compound of formula (IVB), wherein $X_1$ is a sulfonate ester.

In a twentieth embodiment, the present invention provides a method of preparing a compound of formula (IVB) comprising the steps of:

1) reacting a compound of formula (IB):

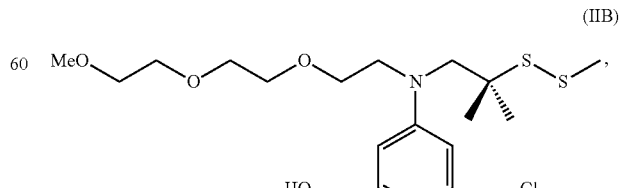

with cyanuric chloride to form a compound of formula (IIB):

2) reacting the compound of formula (IIB) with sulfonating agent to form a compound of formula (VIB):

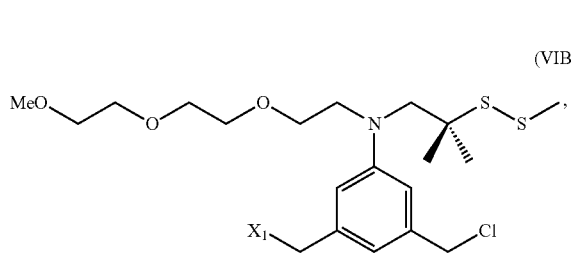
(VIB)

3) reacting the compound of formula (VIB) with a compound of formula (a):

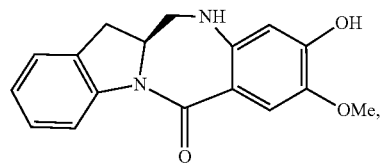
(a)

to form a compound of formula (IIIB):

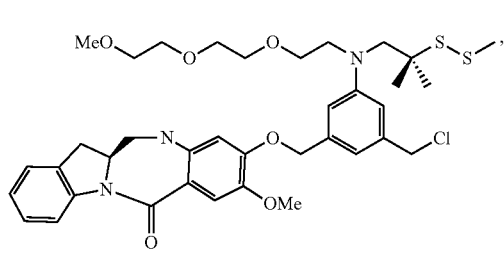
(IIIB)

4) reacting the compound of formula (IIIB) with a compound of formula (b):

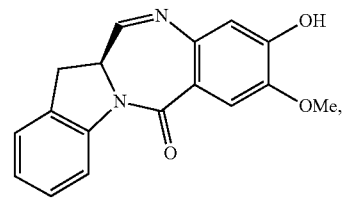
(b)

to form the compound of formula (IVB), wherein $X_1$ is a sulfonate ester.

In a twenty-first embodiment, the present invention provides a method of preparing a compound of formula (IVB) comprising the steps of:

1) reacting a compound of formula (IB):

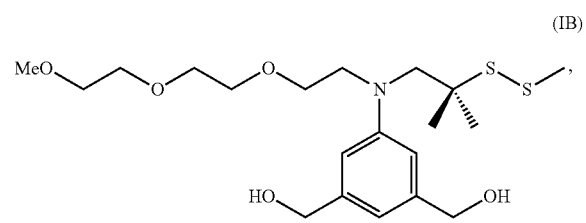
(IB)

with cyanuric chloride to form a compound of formula (IIB):

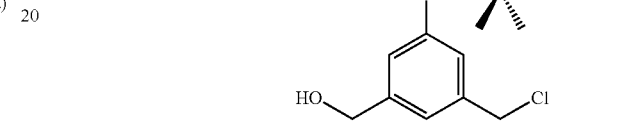
(IIB)

2) reacting the compound of formula (IIB) with sulfonating agent to form a compound of formula (VIB):

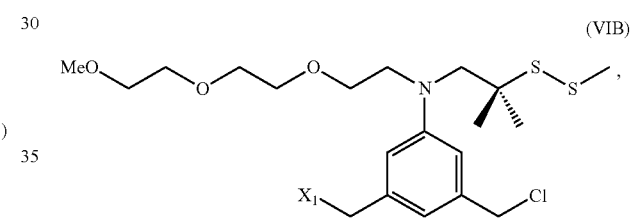
(VIB)

3) reacting the compound of formula (VIB) with a compound of formula (b):

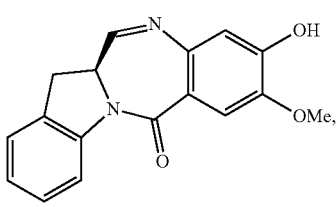
(b)

to form a compound of formula (VB):

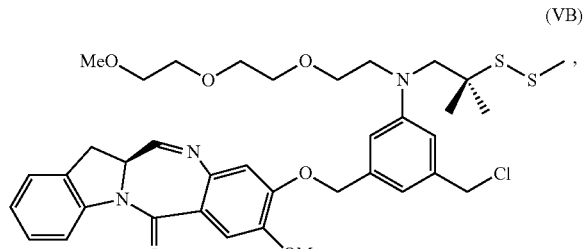
(VB)

4) reacting the compound of formula (VB) with an imine reducing agent to form a compound of formula (IIIB):

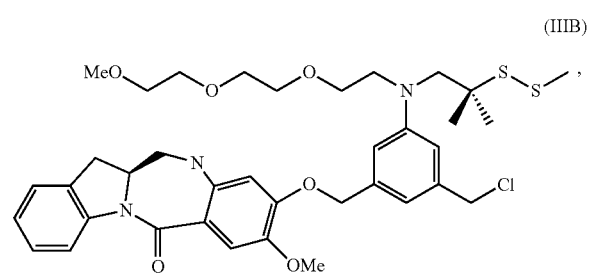

5) reacting the compound of formula (IIIB) with a compound of formula (b):

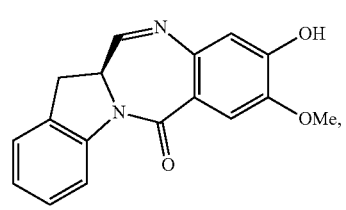

to form the compound of formula (IVB), wherein $X_1$ is a sulfonate ester.

In a twenty-second embodiment, the present invention provides a method of preparing a compound of formula (IVB) comprising the steps of:

1) reacting a compound of formula (IB):

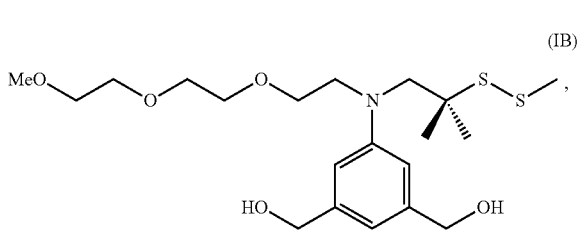

with cyanuric chloride to form a compound of formula (IIB):

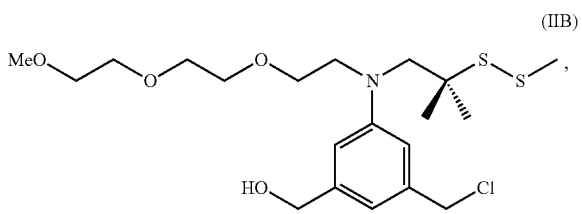

2) reacting the compound of formula (IIB) with a compound of formula (b) to form a compound of formula (VIIB):

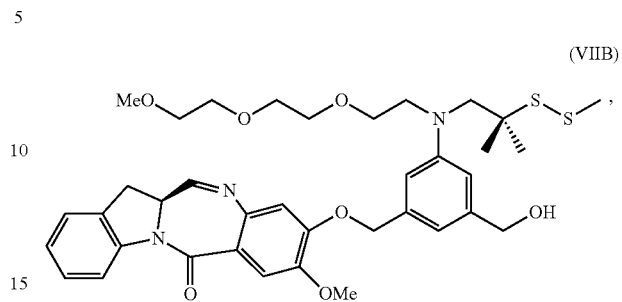

3) reacting the compound of formula (VIIB) with a sulfonating agent to form a compound of formula (VIIIB):

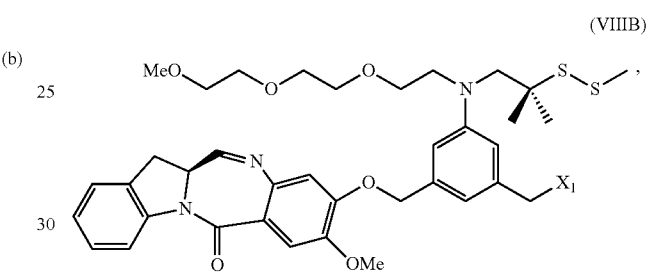

4) reacting the compound of formula (VIIIB) with a compound of formula (a) to form the compound of formula (IVB), wherein $X_1$ is a sulfonate ester.

In a twenty-third embodiment, the present invention provides a method of preparing a compound of formula (IVB) comprising the steps of:

1) reacting a compound of formula (IB):

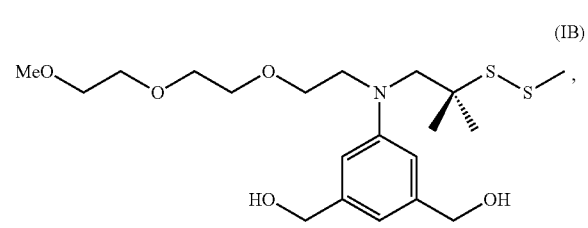

with cyanuric chloride to form a compound of formula (IIB):

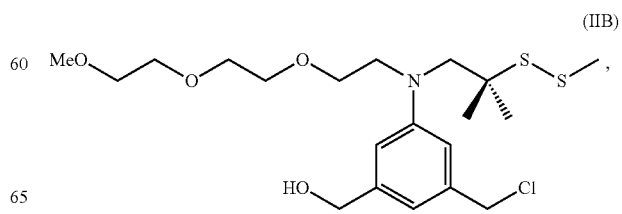

2) reacting the compound of formula (IIB) with a compound of formula (a) to form a compound of formula (IXB):

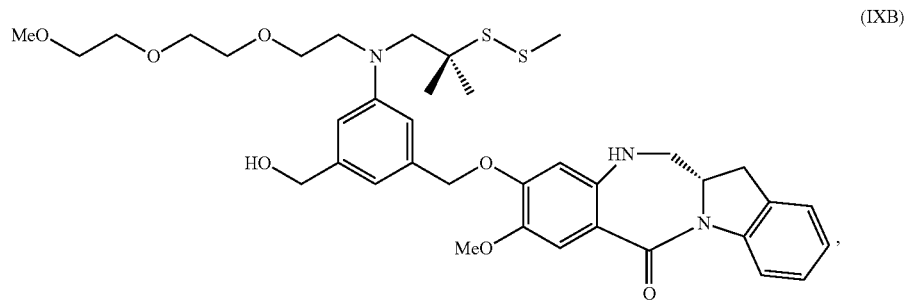

(IXB)

3) reacting the compound of formula (IXB) with a sulfonating agent to form a compound of formula (XB):

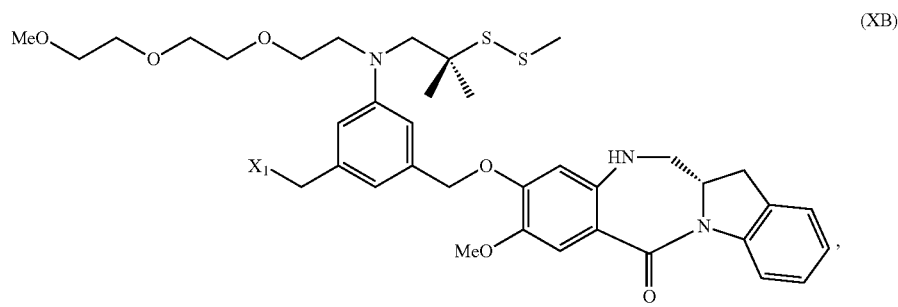

(XB)

4) reacting the compound of formula (XB) with a compound of formula (b):

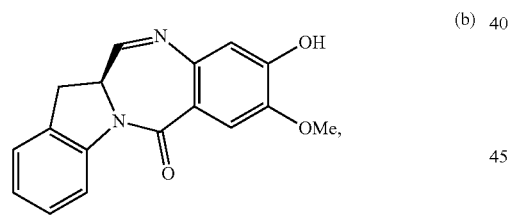

(b)

to form the compound of formula (IVB), wherein $X_1$ is a sulfonate ester.

In a twenty-fourth embodiment, the present invention provides a method of preparing a compound of formula (IVB) comprising the steps of:

1) reacting a compound of formula (IB):

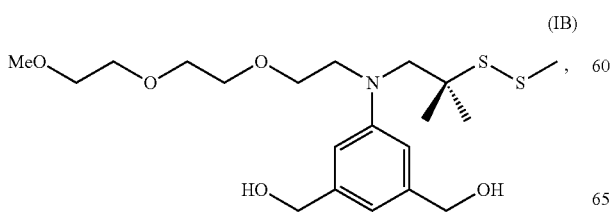

(IB)

with cyanuric chloride to form a compound of formula (IIB):

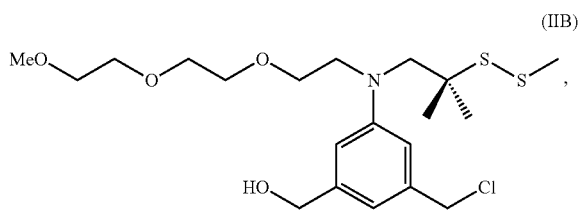

(IIB)

2) reacting the compound of formula (IIB) with a compound of formula (b) to form a compound of formula (VIIB):

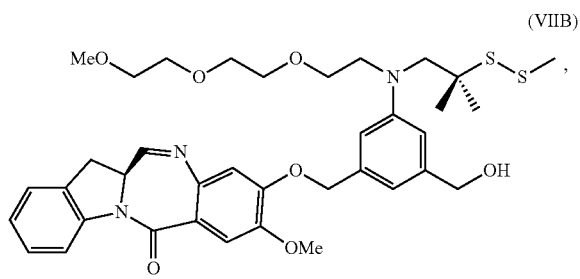

(VIIB)

3) reacting the compound of formula (VIIB) with an imine reducing agent to form a compound of formula (IXB):

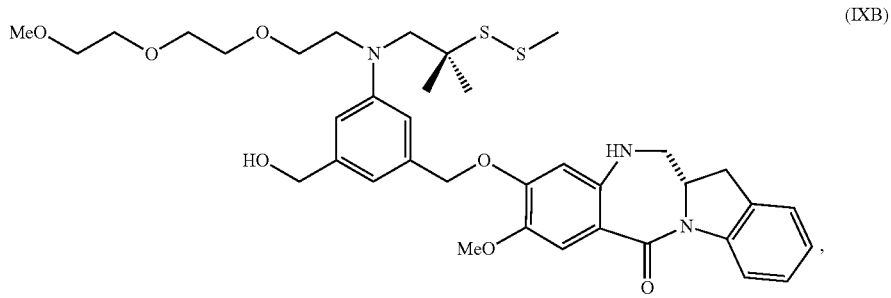

(IXB)

4) reacting the compound of formula (IXB) with a sulfonating agent to form a compound of formula (XB):

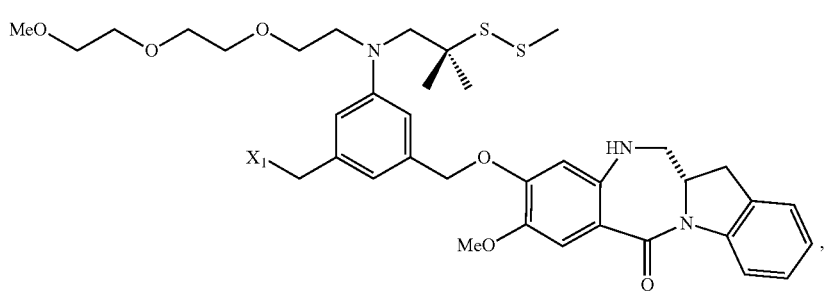

(XB)

and 5) reacting the compound formula (XB) with a compound of formula (b) to form the compound of formula (IVB), wherein $X_1$ is a sulfonate ester.

In a twenty-fifth embodiment, for the reaction between compound of formula (IA) or (IA') with cyanuric chloride in methods described herein (e.g., in the first, second, third, fourth, fifth, sixth, seventh, eighth, ninth, tenth, eleventh or twelfth embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$ or $12^{th}$ specific embodiment), between 0.5 and 0.9 molar equivalent of cyanuric chloride relative to the amount of compound of formula (IA) or (IA') is used. In specific embodiments, between 0.6 and 1.0 molar equivalent of cyanuric chloride relative to the amount of compound of formula (IA) or (IA') is used. In specific embodiments, between 0.6 and 0.8 molar equivalent of cyanuric chloride relative to the amount of compound of formula (IA) or (IA') is used. In specific embodiments, between 0.7 and 0.8 molar equivalent of cyanuric chloride relative to the amount of compound of formula (IA) or (IA') is used. In even more specific embodiments, 0.75 molar equivalent of cyanuric chloride relative to amount of compound of formula (IA) or (IA') is used. In even more specific embodiments, 0.85 molar equivalent of cyanuric chloride relative to the amount of compound of formula (IA) or (IA') is used.

In some embodiments, the reaction between the compound of formula (IA) or (IA') and cyanuric chloride is carried out in a polar solvent. In specific embodiments, the polar solvent is dimethylformamide (DMF).

In some embodiments, the compound of formula (IA) or (IA') is used as a solution or a suspension in dichloromethane (DCM). In some other embodiments, the compound of formula (IA) or (IA') is used as a solution or a suspension in dimethylformamide (DMF).

In some embodiments, the reaction between the compound of formula (IA) or (IA') and cyanuric chloride is carried out in dimethylformamide (DMF). In some other embodiments, the compound of formula (IA) or (IA') is used as a solution or a suspension in dichloromethane (DCM), and the reaction between the compound of formula (IA) or (IA') and cyanuric chloride is carried out in dimethylformamide (DMF).

In some other embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF).

In some embodiments, the amount of solvent is between 5 volumes and 40 volumes relative to the amount of compound of formula (IA) or (IA'). In other embodiments, the amount of solvent is between 10 volumes and 30 volumes relative to the amount of compound of formula (IA) or (IA'). In other embodiments, the amount of solvent is about 5 volumes relative to the amount of compound of formula (IA) or (IA'). In other embodiments, the amount of solvent is about 10 volumes relative to the amount of compound of formula (IA) or (IA'). In other embodiments, the amount of solvent is about 15 volumes relative to the amount of compound of formula (IA) or (IA'). In other embodiments, the amount of solvent is about 20 volumes relative to the amount of compound of formula (IA) or (IA'). In other embodiments, the amount of solvent is about 25 volumes relative to the amount of compound of formula (IA) or (IA'). In other embodiments, the amount of solvent is about 30 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is between 5 volumes and 40 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 5 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 10 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 15 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 20 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 25 volumes relative to the amount of compound of formula (IA) or (IA').

In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 30 volumes relative to the amount of compound of formula (IA) or (IA'). In some embodiments, the compound of formula (IA) or (IA') is used as a solution or a suspension in dimethylformamide (DMF), and the reaction between the compound of formula (IA) or (IA') and cyanuric chloride is carried out in dimethylformamide (DMF), and the amount of DMF is 35 volumes relative to the amount of compound of formula (IA) or (IA').

The reaction between the compound of formula (IA) or (IA') and cyanuric chloride in a polar solvent can be carried out at a suitable temperature. In some embodiments, the reaction is carried out at a temperature between −5° C. and 50° C. In some embodiments, the reaction is carried out at a temperature between 0° C. and 50° C. In some embodiments, the reaction is carried out at a temperature between 5° C. and 50° C. In some embodiments, the reaction is carried out at a temperature between 10° C. and 40° C. In some embodiments, the reaction is carried out at a temperature between −5° C. and 5° C. In more specific embodiments, cyanuric chloride and the polar solvent are mixed at a temperature between −5° C. and 10° C. In more specific embodiments, cyanuric chloride and the polar solvent are mixed at a temperature between 0° C. and 10° C. In more specific embodiments, cyanuric chloride and the polar solvent are mixed at a temperature between 2° C. and 5° C. In other more specific embodiments, the reaction between the compound of formula (IA) or (IA') and cyanuric chloride in a polar solvent is carried out at a temperature between 20° C. and 30° C. In another more specific embodiments, the reaction between the compound of formula (IA) or (IA') and cyanuric chloride in a polar solvent is carried out at 25±3° C. In yet other embodiments, cyanuric chloride and the polar solvent are mixed a temperature between −5° C. and 10° C., and the reaction between the compound of formula (IA) or (IA') and cyanuric chloride in a polar solvent is carried out at a temperature between 20° C. and 30° C. In yet other embodiments, cyanuric chloride and the polar solvent are mixed a temperature between 2° C. and 5° C., and the reaction between the compound of formula (IA) or (IA') and cyanuric chloride in a polar solvent is carried out at 25±3° C.

The reaction between the compound of formula (IA) or (IA') and cyanuric chloride in a polar solvent can be carried out for a period of time until a substantial amount of the compound of formula (IIA) or (IIA') has been formed, respectively. As used herein, a "substantial amount" refers to an amount of the compound of formula (IIA) or (IIA') greater than 40%, greater than 45%, greater than 50%, greater than 55%, or greater than 60% of the product has been formed. In some embodiments, the reaction time between the compound of formula (IA) or (IA') and cyanuric chloride in a polar solvent is between 10 minutes and 48 hours. In some embodiments, the reaction time between the compound of formula (IA) or (IA') and cyanuric chloride in a polar solvent is between 20 minutes and 5 hours. In some embodiments, the reaction time between the compound of formula (IA) or (IA') and cyanuric chloride in a polar solvent is between 30 minutes and 5 hours. In some embodiments, the reaction time between the compound of formula (IA) or (IA') and cyanuric chloride in a polar solvent is between 1 hour and 5 hours. In some embodiments, the reaction time between the compound of formula (IA) or (IA') and cyanuric chloride in a polar solvent is between 1 hour and 4 hours. In some embodiments, the reaction time between the compound of formula (IA) or (IA') and cyanuric chloride in a polar solvent is between 2 hours and 4 hours. In some embodiments, the reaction time between the compound of formula (IA) or (IA') and cyanuric chloride in a polar solvent is between 16 hours and 24 hours.

In a twenty-sixth embodiment, for the reaction between the compound of formula (IB) and cyanuric chloride in the methods described herein (e.g., in the thirteenth, fourteenth, fifteenth, sixteenth, seventeenth, eighteenth, nineteenth, twentieth, twenty-first, twenty-second, twenty-third or twenty-fourth embodiment), between 0.6 and 1.0 molar equivalent of cyanuric chloride relative to the compound of formula (IB) is used. In a specific embodiment, between 0.7 and 0.8 molar equivalent of cyanuric chloride relative to the compound of formula (IB) is used. In more specific embodiments, 0.65 molar equivalent of cyanuric chloride relative to the amount of the compound of formula (IB) is used. In even more specific embodiments, 0.75 molar equivalent of cyanuric chloride relative to the amount of the compound of formula (IB) is used. In even more specific embodiments, 0.85 molar equivalent of cyanuric chloride relative to the amount of the compound of formula (IB) is used.

In some embodiments, the reaction between compound (IB) and cyanuric chloride is carried out in a polar solvent. In specific embodiments, the polar solvent is dimethylformamide (DMF).

In some embodiments, the compound of formula (IB) is used as a solution or a suspension in dichloromethane (DCM). In some other embodiments, the compound of formula (IB) is used as a solution or a suspension in dimethylformamide (DMF).

In some embodiments, the reaction between the compound of formula (IB) and cyanuric chloride is carried out in dimethylformamide (DMF). In some other embodiments, the compound of formula (IB) is used as a solution or a suspension in dichloromethane (DCM), and the reaction between the compound of formula (IB) and cyanuric chloride is carried out in dimethylformamide (DMF).

In some other embodiments, the compound of formula (IB) is used as a solution or a suspension in dimethylformamide (DMF), and the reaction between the compound of formula (IB) and cyanuric chloride is carried out in dimethylformamide (DMF).

In some embodiments, the amount of solvent is between 5 volumes and 40 volumes relative to the amount of compound of formula (IB). In other embodiments, the amount of solvent is between 10 volumes and 30 volumes relative to the amount of compound of formula (IB). In other embodiments, the amount of solvent is about 5 volumes relative to the amount of compound of formula (IB). In other embodiments, the amount of solvent is about 10 volumes relative to the amount of compound of formula (IB). In other embodiments, the amount of solvent is about 15 volumes relative to the amount of compound of formula (IB). In other embodiments, the amount of solvent is about 20 volumes relative to the amount of compound of formula (IB). In other embodiments, the amount of solvent is about 25 volumes relative to the amount of compound of formula (IB). In other embodiments, the amount of solvent is about 30 volumes relative to the amount of compound of formula (IB). In some embodiments, the compound of formula (IB) is used as a solution or a suspension in dimethylformamide (DMF), and the reaction between the compound of formula (IB) and cyanuric chloride is carried out in dimethylformamide (DMF), and the amount of DMF is between 5 volumes and 40 volumes relative to the amount of compound of formula (IB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 5 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 10 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 15 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 20 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 25 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 30 volumes relative to the amount of compound of formula (IIB). In some embodiments, the compound of formula (IIB) is used as a solution or a suspension in dimethylformamide (DMF), and the reaction between the compound of formula (IIB) and cyanuric chloride is carried out in dimethylformamide (DMF), and the amount of DMF is 35 volumes relative to the amount of compound of formula (IIB).

The reaction between compound (IB) and cyanuric chloride in a polar solvent can be carried out at a suitable temperature. In some embodiments, the reaction is carried out at a temperature between −5° C. and 50° C. In some embodiments, the reaction is carried out at a temperature between 0° C. and 50° C. In some embodiments, the reaction is carried out at a temperature between 5° C. and 50° C. In some embodiments, the reaction is carried out at a temperature between 10° C. and 40° C. In some embodiments, the reaction is carried out at a temperature between −5° C. and 5° C. In more specific embodiments, cyanuric chloride and the polar solvent are mixed a temperature between −5° C. and 10° C. In more specific embodiments, cyanuric chloride and the polar solvent are mixed at a temperature between 0° C. and 10° C. In more specific embodiments, cyanuric chloride and the polar solvent are mixed at a temperature between 2° C. and 5° C. In other more specific embodiments, the reaction between the compound of formula (IB) and cyanuric chloride in a polar solvent is carried out in a temperature between 20° C. and 30° C. In another more specific embodiment, the reaction between the compound of formula (IB) and cyanuric chloride in a polar solvent is carried out at 25±3° C. In yet other embodiments, cyanuric chloride and the polar solvent are mixed a temperature between −5° C. and 10° C., and the reaction between the compound of formula (IB) and cyanuric chloride in a polar solvent is carried out at a temperature between 20° C. and 30° C. In yet other embodiments, cyanuric chloride and the polar solvent are mixed a temperature between 2° C. and 5° C., and the reaction between the compound of formula (IB) and cyanuric chloride in a polar solvent is carried out at 25±3° C. In yet other embodiments, cyanuric chloride and the polar solvent are mixed a temperature between −5° C. and 10° C., and the reaction between the compound of formula (IIB) and cyanuric chloride in a polar solvent is carried out at a temperature between 20° C. and 30° C. In yet other embodiments, cyanuric chloride and the polar solvent are mixed a temperature between 2° C. and 5° C., and the reaction between the compound of formula (IIB) and cyanuric chloride in a polar solvent is carried out at 25±3° C.

The reaction between compound (IB) and cyanuric chloride in a polar solvent can be carried out for a period of time until a substantial amount of compound (IIB) has been formed. As used herein, a "substantial amount" refers an amount of the compound of formula (IIB) that is greater than 40%, greater than 45%, greater than 50%, greater than 55%, or greater than 60% of the product has been formed. In some embodiments, the reaction time between the compound of formula (IB) and cyanuric chloride in a polar solvent is between the reaction is carried out for 10 minutes to 48 hours, In some embodiments, the reaction time between the compound of formula (IB) and cyanuric chloride in a polar solvent is between 20 minutes and 5 hours. In some embodiments, the reaction time between the compound of formula (IB) and cyanuric chloride in a polar solvent is between 30 minutes and 5 hours. In some embodiments, the reaction time between the compound of formula (IB) and cyanuric chloride in a polar solvent is between 1 hour and 5 hours. In some embodiments, the reaction time between the compound of formula (IB) and cyanuric chloride in a polar solvent is between 1 hour and 4 hours. In some embodiments, the reaction time between the compound of formula (IB) and cyanuric chloride in a polar solvent is between 2 hour and 4 hours. In some embodiments, the reaction time between the compound of formula (IB) and cyanuric chloride in a polar solvent is between 16 hours and 24 hours.

In a twenty-seventh embodiment, the reaction between the compound of formula (IIA') or (IIA) and the compound of formula (a) in the methods described herein (e.g., in the second, third, fourth or twenty-fifth embodiment or the $2^{nd}$, $3^{rd}$ or $4^{th}$ specific embodiment), the reaction between the compound formula (IIA') or (IIA) and the compound of formula (b) in the methods described herein (e.g. in the fifth, sixth or twenty-fifth embodiment or the $5^{th}$ or $6^{th}$ specific embodiment), the reaction between the compound of formula (IIB) and the compound of formula (a) in the methods described herein (e.g. in the fourteenth, fifteenth, sixteenth or twenty-sixth embodiment), or the reaction between the compound of formula (IIB) and the compound of formula (b) in the methods described herein (e.g., in the seventeenth, eighteenth or twenty-sixth embodiment) is carried out in the presence of an alcohol activating agent and an azodicarboxylate. In one embodiment, the alcohol activating agent is a trialkylphosphine, triarylphosphine, or triheteroarylphosphine. In specific embodiments, the alcohol activating agent is trimethylphosphine, tri-n-butylphosphine, tri(o-tolyl)phosphine, tri(m-tolyl)phosphine, tri(p-tolyl)phosphine, tri(2-pyridyl)phosphine, tri(3-pyridyl)phosphine, tri(4-pyridyl)phosphine, or [4-(3,3,4,4,5,5,6,6,7,7,8,8,9,9,10,10,10-heptadecafluorodecyl)phenyl]diphenylphosphine. In other specific embodiments, the alcohol activating agent can be a phosphine-like reagent, such as (tri-n-butylphosphoranylidene)acetonitrile, (cyanomethylene)tributylphosphorane (CMBP), or (cyanomethylene)trimethylphosphorane (CMMP). In more specific embodiments, the alcohol activating agent is triphenylphosphine. In yet other more specific embodiments, the alcohol activating agent is tri-n-butylphosphine. In some embodiments, the alcohol activating agent can be polymer-bound or polymer-supported, such as polymer-bound or polymer-supported trialkyl phosphine, triarylphosphine (e.g., triphenylphosphine), or triheteroarylphosphine.

In some embodiments, for the method described in the twenty-seventh embodiment, the azodicarboxylate is selected from diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis (2,2,2-trichloroethyl) azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl) azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In some specific embodiments, for the method described in the twenty-seventh embodiment, the reaction between the compound of formula (IIA') or (IIA) and the compound of formula (a), the reaction between the compound of formula (IIA') or (IIA) and the compound of formula (b), the reaction between the compound of formula (IIB) and the compound of formula (a), or the reaction between the compound of formula (IIB) and the compound of formula (b) is carried out in the presence of tri-n-butylphosphine or triphenylphosphine and an azodicarboxylate. In some embodiments, the azodicarboxylate is selected from diethyl azodicarboxylate (DEAD), diisopropyl azodicarboxylate (DIAD), 1,1'-(azodicarbonyl)dipiperidine (ADDP), and ditertbutyl azodicarboxylate (DTAD). More specifically, the azodicarboxylate is DIAD.

In some more specific embodiments, for the method described in the twenty-seventh embodiment, the reaction between the compound of formula (IIA') or (IIA) and the compound of formula (a) is carried out in the presence of triphenylphosphine and DIAD. In some more specific embodiments, for the method described in the twenty-seventh embodiment, the reaction between the compound of formula (IIA') or (IIA) and the compound of formula (b) is carried out in the presence of triphenylphosphine and DIAD. In some more specific embodiments, for the method described in the twenty-seventh embodiment, the reaction between the compound of formula (IIB) and the compound of formula (a) is carried out in the presence of triphenylphosphine and DIAD. In some more specific embodiments, for the method described in the twenty-seventh embodiment, the reaction between the compound of formula (IIB) and the compound of formula (b) is carried out in the presence of triphenylphosphine and DIAD.

In other more specific embodiments, for the method described in the twenty-seventh embodiment, the reaction between the compound of formula (IIA') or (IIA) and the compound of formula (a) is carried out in the presence of tri-n-butylphosphine and DIAD. In other more specific embodiments, for the method described in the twenty-seventh embodiment, the reaction between the compound of formula (IIA') or (IIA) and the compound of formula (b) is carried out in the presence of tri-n-butylphosphine and DIAD. In some more specific embodiments, for the method described in the twenty-seventh embodiment, the reaction between the compound of formula (IIB) and the compound of formula (a) is carried out in the presence of tri-n-butylphosphine and DIAD. In some more specific embodiments, for the method described in the twenty-seventh embodiment, the reaction between the compound of formula (IIB) and the compound of formula (b) is carried out in the presence of tri-n-butylphosphine and DIAD.

In certain embodiments, for the method described in the twenty-seventh embodiment, the alcohol activating agent and the azodicarboxylate are mixed together to form an alcohol activating agent-azodicarboxylate complex. In some embodiments, the compound of formula (IIA') or (IIA) is mixed with the activating agent-azodicarboxylate complex first before contacting with the compound of formula (a). In some embodiments, the compound of formula (IIA') or (IIA) is mixed with the activating agent-azodicarboxylate complex first before contacting with the compound of formula (b). In some other embodiments, the compound of formula (a) is mixed with the activating agent-azodicarboxylate complex first before contacting with the compound of formula (IIA') or (IIA). In some other embodiments, the compound of formula (b) is mixed with the activating agent-azodicarboxylate complex first before contacting with the compound of formula (IIA') or (IIA). In some embodiments, the compound of formula (IIB) is mixed with the activating agent-azodicarboxylate complex first before contacting with the compound of formula (a). In some embodiments, the compound of formula (IIB) is mixed with the activating agent-azodicarboxylate complex first before contacting with the compound of formula (b). In some other embodiments, the compound of formula (a) is mixed with the activating agent-azodicarboxylate complex first before contacting with the compound of formula (IIB). In some other embodiments, the compound of formula (b) is mixed with the activating agent-azodicarboxylate complex first before contacting with the compound of formula (IIB). In certain embodiments, for the method of twenty-seventh embodiment or any specific embodiments described therein, the reaction between the compound of formula (IIA') or (IIA) and the compound of formula (a) is carried out in an solvent(s). In certain embodiments, for the method of twenty-seventh embodiment or any specific embodiments described therein, the reaction between the compound of formula (IIA') or (IIA) and the compound of formula (b) is carried out in in an solvent(s). In certain embodiments, for the method of twenty-seventh embodiment or any specific embodiments described therein, the reaction between the compound of formula (IIB) and the compound of formula (a) is carried out in in an solvent(s). In certain embodiments, for the method of twenty-seventh embodiment or any specific embodiments described therein, the reaction between the compound of formula (IIB) and the compound of formula (b) is carried out in in an solvent(s). Any suitable solvent(s) described herein can be used. In some embodiments, a suitable solvent is selected from dichloromethane ($CH_2Cl_2$), acetonitrile (MeCN), tetrahydrofuran (THF), toluene, N-methylmorpholine (NMM), or any combination thereof. In some more specific embodiments, the solvent is THF.

In certain embodiments, for the method of twenty-seventh embodiment or any specific embodiments described therein, the reaction between the compound of formula (IIA') or (IIA) and the compound of formula (a) is carried out at a temperature between 0° C. and 50° C., between 0° C. and 40° C., between 5° C. and 30° C., between 10° C. and 30° C. or between 15° C. and 25° C. In some specific embodiments, the reaction between the compound of formula (IIA') or (IIA) and the compound of formula (a) is initially carried out at a temperature between 0° C. and 10° C., and then carried out at a temperature between 20° C. and 30° C. In certain embodiments, for the method of twenty-first embodiment or any specific embodiments described therein, the reaction between the compound of formula (IIA') or (IIA) and the compound of formula (b) is carried out at a temperature between 0° C. and 50° C., between 0° C. and 40° C., between 5° C. and 30° C., between 10° C. and 30° C. or between 15° C. and 25° C. In some specific embodiments, the reaction between the compound of formula (IIA') or (IIA) and the compound of formula (b) is initially carried out at a temperature between 0° C. and 10° C., and then carried out at a temperature between 20° C. and 30° C. In certain embodiments, for the method of twenty-first embodiment or any specific embodiments described therein, the reaction between the compound of formula (IIB) and the compound of formula (a) is carried out at a temperature between 0° C. and 50° C., between 0° C. and 40° C., between 5° C. and 30° C., between 10° C. and 30° C. or between 15° C. and 25° C. In some specific embodiments, the reaction between the compound of formula (IIB) and the compound of formula (a) is initially carried out at a temperature between 0° C. and 10° C., and then carried out at a temperature between 20° C. and 30° C. In certain embodiments, for the method of twenty-seventh embodiment or any specific embodiments described therein, the reaction between the compound of formula (IIB) and the compound of formula (b) is carried out at a temperature between 0° C. and 50° C., between 0° C. and 40° C., between 5° C. and 30° C., between 10° C. and 30° C. or between 15° C. and 25° C. In some specific embodiments, the reaction between the compound of formula (IIB) and the compound of formula (b) is initially carried out at a temperature between 0° C. and 10° C., and then carried out at a temperature between 20° C. and 30° C.

In a twenty-eighth embodiment, the reaction between the compound of formula (IIIA') or (IIIA) and the compound of formula (b) in the methods described herein (e.g., in the third, fourth, sixth, eighth, ninth, twenty-fifth or twenty-seventh embodiment or the $3^{rd}$, $4^{th}$, $6^{th}$, $8^{th}$ or $9^{th}$ specific embodiment) is carried out in the presence of a base. In a twenty-eighth embodiment, the reaction between the compound of formula (VA') or (VA) and the compound of formula (a) in the methods described herein (e.g., in the fifth, seventh, twenty-fifth or twenty-seventh embodiment or the $5^{th}$ or $7^{th}$ specific embodiment) is carried out in the presence of a base. In a twenty-eighth embodiment, the reaction between the compound of formula (IIA') or (IIA) and the compound of formula (b) in the methods described herein (e.g., in the tenth, twelfth or twenty-fifth embodiment or the $10^{th}$ or $12^{th}$ specific embodiment) is carried out in the presence of a base. In a twenty-eighth embodiment, the reaction between the compound of formula (IIA) and the compound of formula (a) in the methods described herein (e.g., in the eleventh or twenty-fifth embodiment or the 11$^{th}$ specific embodiment) is carried out in the presence of a base. In a twenty-eighth embodiment, the reaction between the compound of formula (IIIB) and the compound of formula (b) in the methods described herein (e.g., in the fifteenth, sixteenth, eighteenth, twentieth, twenty-first, twenty-sixth or twenty-seventh embodiment) is carried out in the presence of a base. In a twenty-eighth embodiment, the reaction between the compound of formula (VB) and the compound of formula (a) described herein (e.g., in the seventeenth, nineteenth, twenty-sixth or twenty-seventh embodiment) is carried out in the presence of a base. In a twenty-eighth embodiment, the reaction between the compound of formula (IIB) and the compound of formula (b) in the methods described herein (e.g., in the twenty-second, twenty-fourth or twenty-sixth embodiment) is carried out in the presence of a base. In a twenty-eighth embodiment, the reaction between the compound of formula (IIB) and the compound of formula (a) in the methods described herein (e.g., in the twenty-third or twenty-sixth embodiment) is carried out in the presence of a base. In certain specific embodiments, the base is sodium carbonate, potassium carbonate, cesium carbonate, sodium hydride, or potassium hydride. In some more specific embodiments, the base is potassium carbonate.

In certain embodiments, for the method described in the twenty-eighth embodiment, the reaction between the compound of formula (IIIA') or (IIIA) and the compound of formula (b) further comprises potassium iodide or cesium iodide. In certain embodiments, for the method described in the twenty-eighth embodiment, the reaction between the compound of formula (VA') or (VA) and the compound of formula (a) further comprises potassium iodide or cesium iodide. In certain embodiments, for the method described in the twenty-eighth embodiment, the reaction between the compound of formula (IIA') or (IIA) and the compound of formula (b) further comprises potassium iodide or cesium iodide. In certain embodiments, for the method described in the twenty-eighth embodiment, the reaction between the compound of formula (IIA') or (IIA) and the compound of formula (a) further comprises potassium iodide or cesium iodide. In certain embodiments, for the method described in the twenty-eighth embodiment, the reaction between the compound of formula (IIIB) and the compound of formula (b) further comprises potassium iodide or cesium iodide. In certain embodiments, for the method described in the twenty-eighth embodiment, the reaction between the compound of formula (VB) and the compound of formula (a) further comprises potassium iodide or cesium iodide. In certain embodiments, for the method described in the twenty-eighth embodiment, the reaction between the compound of formula (IIB) and the compound of formula (b) further comprises potassium iodide or cesium iodide. In certain embodiments, for the method described in the twenty-eighth embodiment, the reaction between the compound of formula (IIB) and the compound of formula (a) further comprises potassium iodide or cesium iodide. In some specific embodiments, the reaction between the compound of formula (IIIA') or (IIIA) and the compound of formula (b) comprises potassium iodide. In some specific embodiments, the reaction between the compound of formula (VA') or (VA) and the compound of formula (a) comprises potassium iodide. In certain embodiments, for the method described in the twenty-eighth embodiment, the reaction between the compound of formula (IIA') or (IIA) and the compound of formula (b) further comprises potassium iodide. In certain embodiments, for the method described in the twenty-eighth embodiment, the reaction between the compound of formula (IIA') or (IIA) and the compound of formula (a) further comprises potassium iodide. In some specific embodiments, the reaction between the compound of formula (IIIB) and the compound of formula (b) comprises potassium iodide. In some specific embodiments, the reaction between the compound of formula (VB) and the compound of formula (a) comprises potassium iodide. In certain embodiments, for the method described in the twenty-eighth embodiment, the reaction between the compound of formula (IIB) and the compound of formula (b) further comprises potassium iodide. In certain embodiments, for the method described in the twenty-eighth embodiment, the reaction between the compound of formula (IIB) and the compound of formula (a) further comprises potassium iodide.

In certain embodiments, for the method described in the twenty-eighth embodiment, the reaction between the compound of formula (IIIA') or (IIIA) and the compound of formula (b) is carried out in the presence of potassium carbonate and potassium iodide. In certain embodiments, for the method described in the twenty-eighth embodiment, the reaction between the compound of formula (VA') or (VA) and the compound of formula (a) is carried out in the presence of potassium carbonate and potassium iodide. In certain embodiments, for the method described in the twenty-eighth embodiment, the reaction between the compound of formula (IIA') or (IIA) and the compound of formula (b) is carried out in the presence of potassium carbonate and potassium iodide. In certain embodiments, for the method described in the twenty-eighth embodiment, the reaction between the compound of formula (IIA') or (IIA) and the compound of formula (a) is carried out in the presence of potassium carbonate and potassium iodide. In certain embodiments, for the method described in the twenty-eighth embodiment, the reaction between the compound of formula (IIIB) and the compound of formula (b) is carried out in the presence of potassium carbonate and potassium iodide. In certain embodiments, for the method described in the twenty-eighth embodiment, the reaction between the compound of formula (VB) and the compound of formula (a) is carried out in the presence of potassium carbonate and potassium iodide. In certain embodiments, for the method described in the twenty-eighth embodiment, the reaction between the compound of formula (IIB) and the compound of formula (b) is carried out in the presence of potassium carbonate and potassium iodide. In certain embodiments, for the method described in the twenty-eighth embodiment, the reaction between the compound of formula (IIB) and the compound of formula (a) is carried out in the presence of potassium carbonate and potassium iodide.

Any suitable solvents can be used for the methods of the twenty-eighth embodiment. In some embodiments, the solvent is a polar aprotic solvent. Exemplary solvents include, but are not limited to, dimethylformamide (DMF), dichloromethane (DCM or $CH_2Cl_2$), dichloroethane (DCE), tetrahydrofuran (THF), dimethylacetamide (DMA or DMAc), etc. In specific embodiments, the solvent is dimethylformamide or dimethylacetamide.

In a twenty-ninth embodiment, for the reaction between the compound of formula (VA') or (VA) and the imine reducing agent, or for the reaction between the compound of formula (VIIA') or (VIIA) and the imine reducing agent, or for the reaction between the compound of formula (VB) and the imine reducing agent, or for the reaction between the compound of formula (VIIB) and the imine reducing agent in the methods described herein (e.g., in the sixth, ninth, twelfth, eighteenth, twenty-first, twenty-fourth, twenty-fifth, twenty-sixth, twenty-seventh or twenty-eighth embodiment or the $6^{th}$, $9^{th}$ or $12^{th}$ specific embodiment), the imine reducing agent is selected from sodium borohydride, sodium triacetoxy borohydride, sodium cyanoborohydride, lithium aluminum hydride, hydrogen gas, ammonium formate, borane, diborane, borane-tetrahydrofuran complex (borane-THF), borane-dimethyl sulfide complex (BMS), borane-1,4-oxathaine complex, 9-borabicyclo[3.3.1]nonane (9-BBN), diisobutylaluminium hydride (DIBAL), lithium borohydride ($LiBH_4$), potassium borohydride ($KBH_4$), or sodium bis(2-methoxyethoxy)aluminumhydride (Red-Al). In specific embodiments, the imine reducing reagent is sodium triacetoxy borohydride ($NaBH(OAc)_3$).

In certain embodiments, for the methods of twenty-ninth embodiment, the reaction between the compound of formula (VA') or (VA) and the imine reducing agent, or the reaction between the compound of formula (VIIA') or (VIIA) and the imine reducing agent, or the reaction between the compound of formula (VB) and the imine reducing agent, or the reaction between the compound of formula (VIIB) and the imine reducing agent can be carried out in a suitable solvent selected from alcohols, ethers, halogenated solvent. In some specific embodiments, the solvent is selected from methanol, ethanol, THF or DCM. In some more specific embodiments, the solvent is dichloromethane.

In a thirtieth embodiment, for compound of formula (VIA'), (VIA), (VIIIA'), (VIIIA), (XA'), (XA), (VIIIB), or (XB), $X_1$ is mesylate, tosylate, brosylate, or triflate. In some specific embodiments, $X_1$ is mesylate.

In some embodiments, the sulfonating agent is a sulfonic anhydride, such as methanesulfonic anhydride, or a sulfonic chloride, such as methanesulfonyl chloride (MsCl). In some specific embodiments, the sulfonating agent is methane sulfonic anhydride. In some specific embodiments, the sulfonating agent is methane sulfonyl chloride.

In some embodiments, the reaction between the compound of formula (IIA'), (IIA), (VIIA'), (VIIA), (IXA'), (IXA), (IIB), (VIIB), or (IXB) with the sulfonating agent in the methods describe herein (e.g., in the seventh, eighth, ninth, tenth, eleventh, twelfth, nineteenth, twentieth, twenty-first, twenty-second, twenty-third, twenty-fourth, twenty-fifth, twenty-sixth, twenty-seventh, twenty-eighth or twenty-ninth embodiment) is carried out in the presence of a base. In some embodiments, the base is a non-nucleophilic base. Exemplary non-nucleophilic bases include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. In some embodiments, the base is triethylamine or diisopropylethylamine. In some more specific embodiments, the base is triethylamine. In some more specific embodiments, the base is diisopropylethylamine.

Any suitable solvents can be used for the reaction between the compound of formula (IIA'), (IIA), (VIIA'), (VIIA), (IXA'), (IXA), (IIB), (VIIB), or (IXB) with the sulfonating agent. In one embodiment, the solvent is dichloromethane.

In a thirty-first embodiment, the reaction between the compound of formula (VIA') or (VIA) and the compound of formula (b) in the methods described herein (e.g., in the seventh, ninth, twenty-sixth, twenty-seventh, twenty-eighth, twenty-ninth or thirtieth embodiment or the $7^{th}$ or $9^{th}$ specific embodiment) is carried out in the presence of a base. In a thirty-first embodiment, the reaction between the compound of formula (VIA') or (VIA) and the compound of formula (a) in the methods described herein (e.g. in the eighth, twenty-fifth, twenty-seventh, twenty-eighth, twenty-ninth or thirtieth embodiment or the $8^{th}$ specific embodiment) is carried out in the presence of a base. In a thirty-first embodiment, the reaction between the compound of formula (VIIIA') or (VIIIA) and the compound of formula (a) in the methods described herein (e.g., in the tenth, twenty-fifth, twenty-seventh, twenty-eighth, twenty-ninth or thirtieth embodiment or the $10^{th}$ specific embodiment) is carried out in the presence of a base. In a thirty-first embodiment, the reaction between the compound of formula (XA') or (XA) and the compound of formula (b) in the methods described herein (e.g., in the eleventh, twelfth, twenty-fifth, twenty-seventh, twenty-eighth, twenty-ninth or thirtieth embodiment or the $11^{th}$ or $12^{th}$ specific embodiment) is carried out in the presence of a base. In a thirty-first embodiment, the reaction between the compound of formula (VIB) and the compound of formula (b) in the methods described herein (e.g., in the nineteenth, twenty-first, twenty-sixth, twenty-seventh, twenty-eighth, twenty-ninth or thirtieth embodiment) is carried out in the presence of a base. In a thirty-first embodiment, the reaction between the compound of formula (VIB) and the compound of formula (a) in the methods described herein (e.g. in the twentieth, twenty-sixth, twenty-seventh, twenty-eighth, twenty-ninth or thirtieth embodiment) is carried out in the presence of a base. In a thirty-first embodiment, the reaction between the compound of formula (VIIIB) and the compound of formula (a) in the methods described herein (e.g., in the twenty-second, twenty-sixth, twenty-seventh, twenty-eighth, twenty-ninth or thirtieth embodiment) is carried out in the presence of a base. In a thirty-first embodiment, the reaction between the compound of formula (XB) and the compound of formula (b) in the methods described herein (e.g., in the twenty-third, twenty-fourth, twenty-sixth, twenty-seventh, twenty-eighth, twenty-ninth or thirtieth embodiment) is carried out in the presence of a base. Examples of the base include, but are not limited to sodium carbonate, potassium carbonate, cesium carbonate, sodium hydride, or potassium hydride. In certain embodiments, the base is potassium carbonate.

Any suitable solvents can be used for the methods of the thirty-first embodiment. In some embodiments, the solvent is a polar aprotic solvent. Exemplary solvents include, but are not limited to, dimethylformamide (DMF), dichloromethane (DCM or $CH_2Cl_2$), dichloroethane (DCE), tetrahydrofuran (THF), dimethylacetamide (DMA or DMAc), etc. In specific embodiments, the solvent is dimethylformamide or dimethylacetamide.

In certain embodiments, for methods described herein, the compound of formula (IVB) is reacted with a reducing agent to form a compound of formula (VIIB):

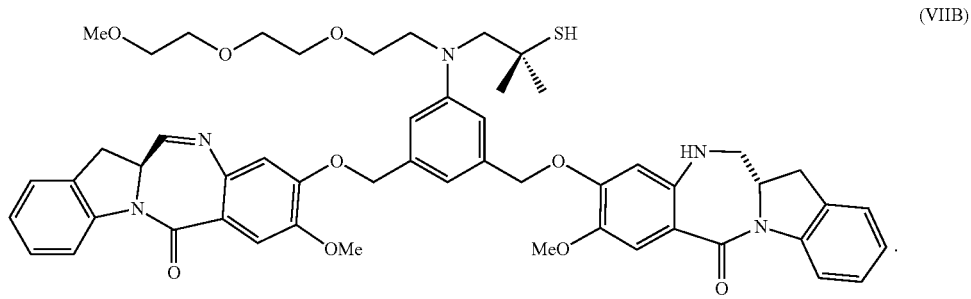

(VIIB)

Any suitable reducing agent that can reduce a disulfide group to a thiol group can be used in the reaction. Exemplary reducing agents include, but are not limited to, dithiothreitol (DTT), tris(2-carboxyethyl)phosphine (TCEP), or 2-mercaptoethanol. In some specific embodiments, the reducing agent is TCEP.

In some embodiments, for methods described herein, the compound of formula (VIIB) is reacted with sodium bisulfite, sodium hydrosulfite or sodium metabisulfite to form a compound of formula (VIIIB):

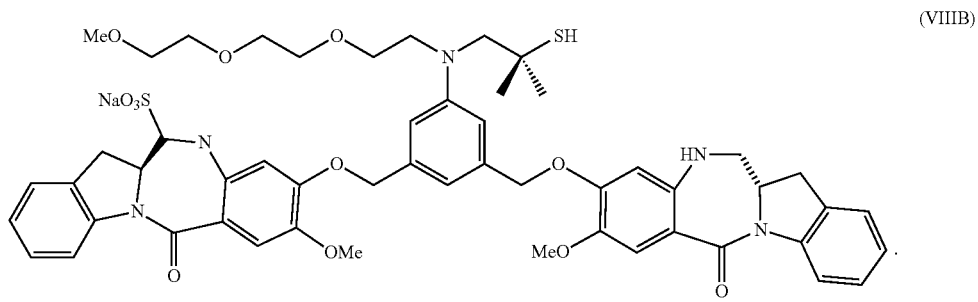

(VIIIB)

In some embodiments, the compound of formula (VIIB) is reacted with sodium bisulfite to form the compound of formula (VIIIB). Any suitable solvent can be used for the reaction. Exemplary solvents, include, but are not limited to, water, DMA, acetone, DMF etc. or a mixture of thereof. In some embodiments, the reaction is carried out in a mixture of water and DMA.

EXAMPLES

Example 1. Synthesis of Methyl 6-(((S)-1-(((S)-1-((3-(chloromethyl)-5-(hydroxymethyl)phenyl)amino)-1-oxopropan-2-yl)amino)-1-oxopropan-2-yl)amino)-6-oxohexanoate (Compound 2)

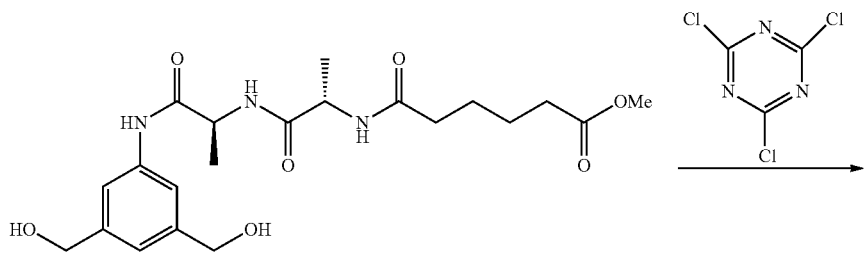

1

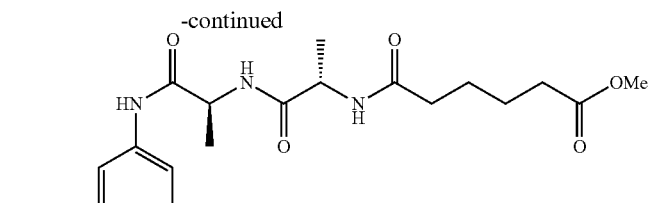

2

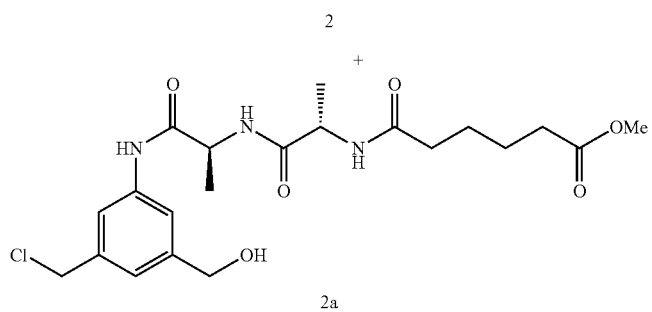

2a

To a dry 100 mL round bottom flask equipped with a stir bar and thermocouple under inert nitrogen was charged DMF (5.0 mL, 5 vol). Cyanuric chloride (0.274 g, 0.65 eq, 1.49 mmol) was added portion-wise over 10 minutes. The solution was stirred for 60±10 minutes. and a DMF solution (5.0 mL, 5 vol) of methyl 6-(((S)-1-(((S)-1-((3,5-bis(hydroxymethyl)phenyl)amino)-1-oxopropan-2-yl)amino)-1-oxopropan-2-yl)amino)-6-oxohexanoate (compound 1, 1.0 g, 2.29 mmol, 1.0 eq.) was then added dropwise while cooling of the reactions in an ice bath. The reaction mixture was stirred for 16 to 24 hours and a sample of the reaction mixture was analyzed by HPLC (see FIG. 1A, peak at ~1.0 minute corresponds to the starting material 1; peak at ~1.3 minute corresponds to the monochlorinated product 2; and peak at ~1.5 minute corresponds to the dichlorinated byproduct 2a). The reaction mixture was cooled to 2 to 5° C. and 0.1M NaOH (5.0 mL, 5 vol) was slowly added to the reaction mixture. The resulting mixture was stirred for 30±5 min and then extracted with ethyl acetate (50.0 mL, 50.0 vol). The organic layer was separated and washed with water (2×10.0 mL, 2×10 vol). The combined aqueous layer was extracted with ethyl acetate (50.0 mL, 50.0 vol). Organic phases were combined and concentrated. The crude material was purified via silica gel column chromatography eluted with a gradient of 0-30% (wherein the solvent system is made up of (i) 20% methanol in dichloromethane) and (ii) dichloromethane) over 25 minutes. The product containing fractions were combined and concentrated under vacuum to afford the desired product.

Figure 1B:
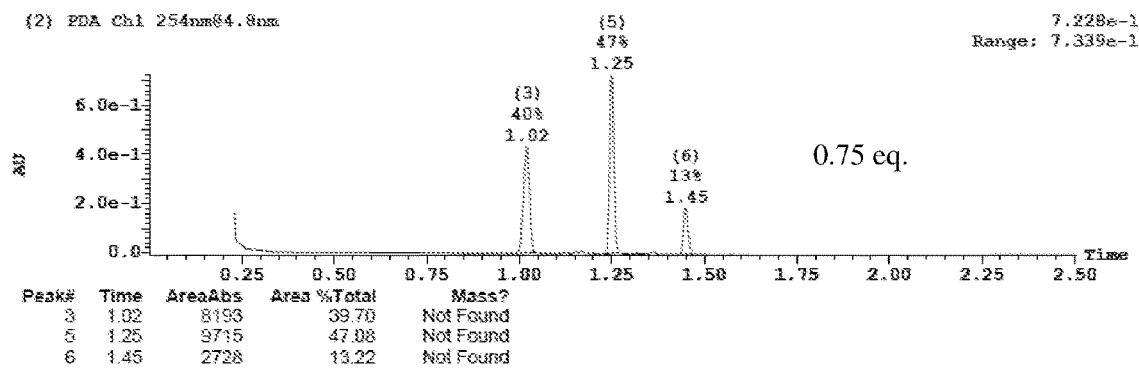
Figure 1C:
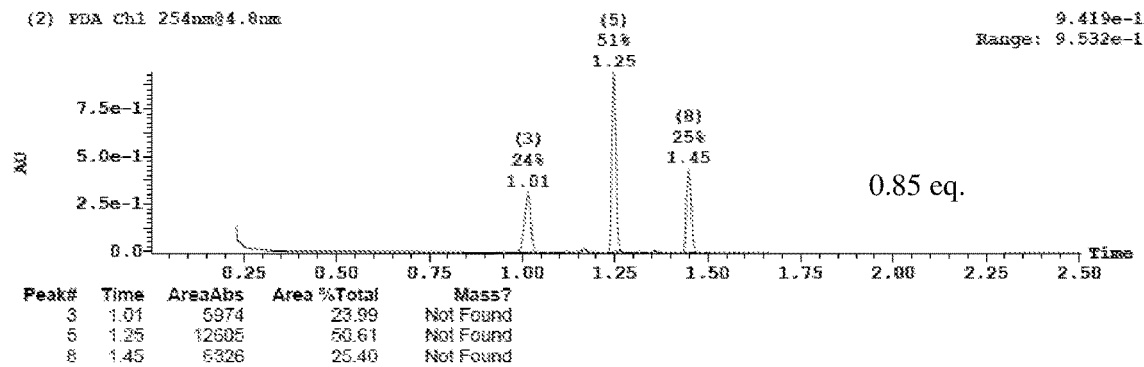
Figure 1D:
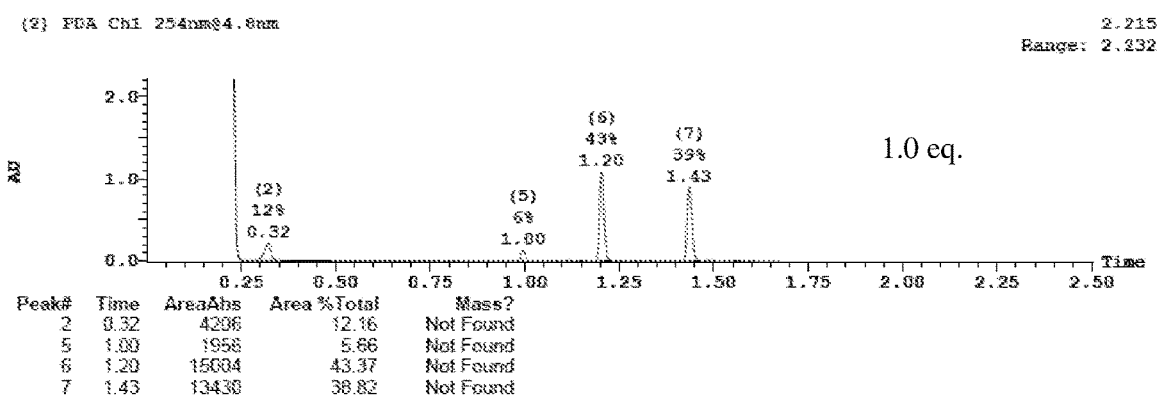
Figure 2:
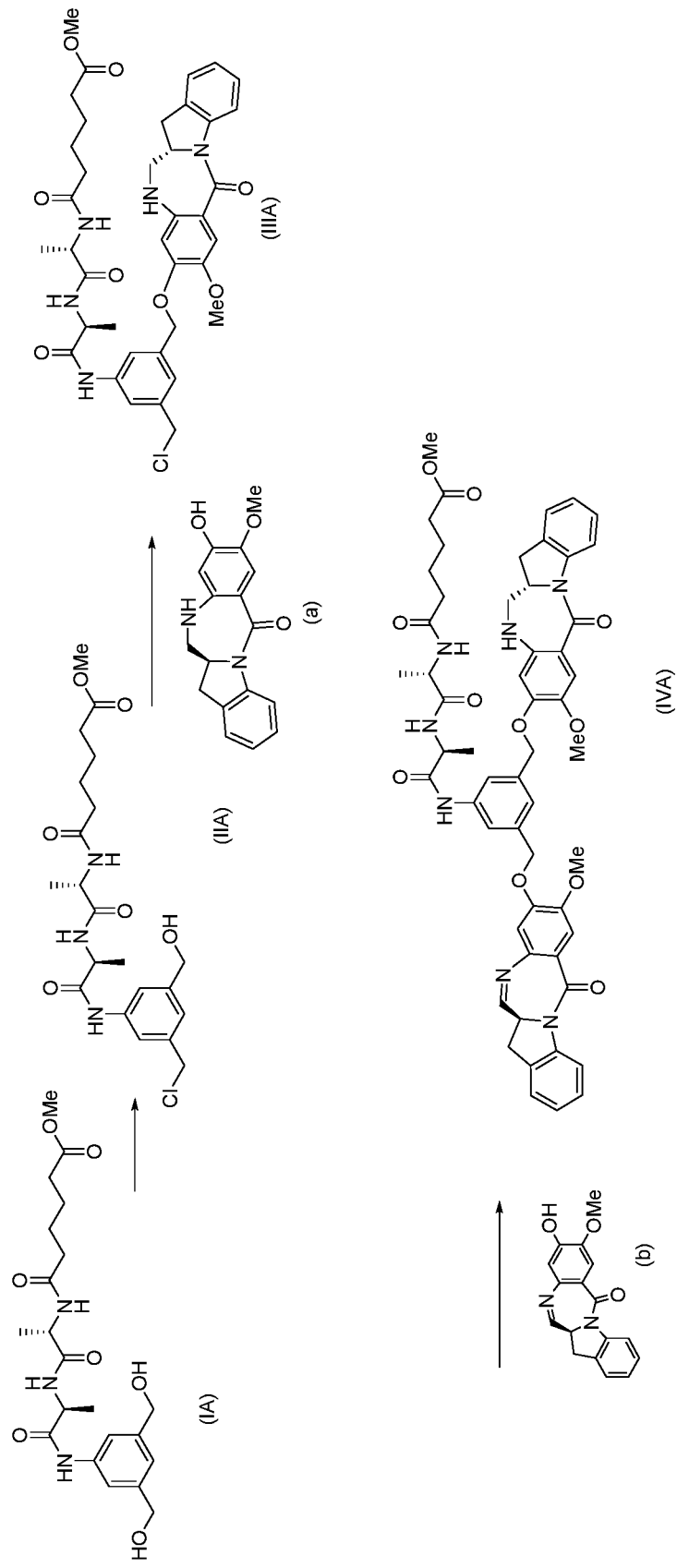
FIGS. 2-19 depict exemplary synthetic schemes of the present invention.
Figure 3:
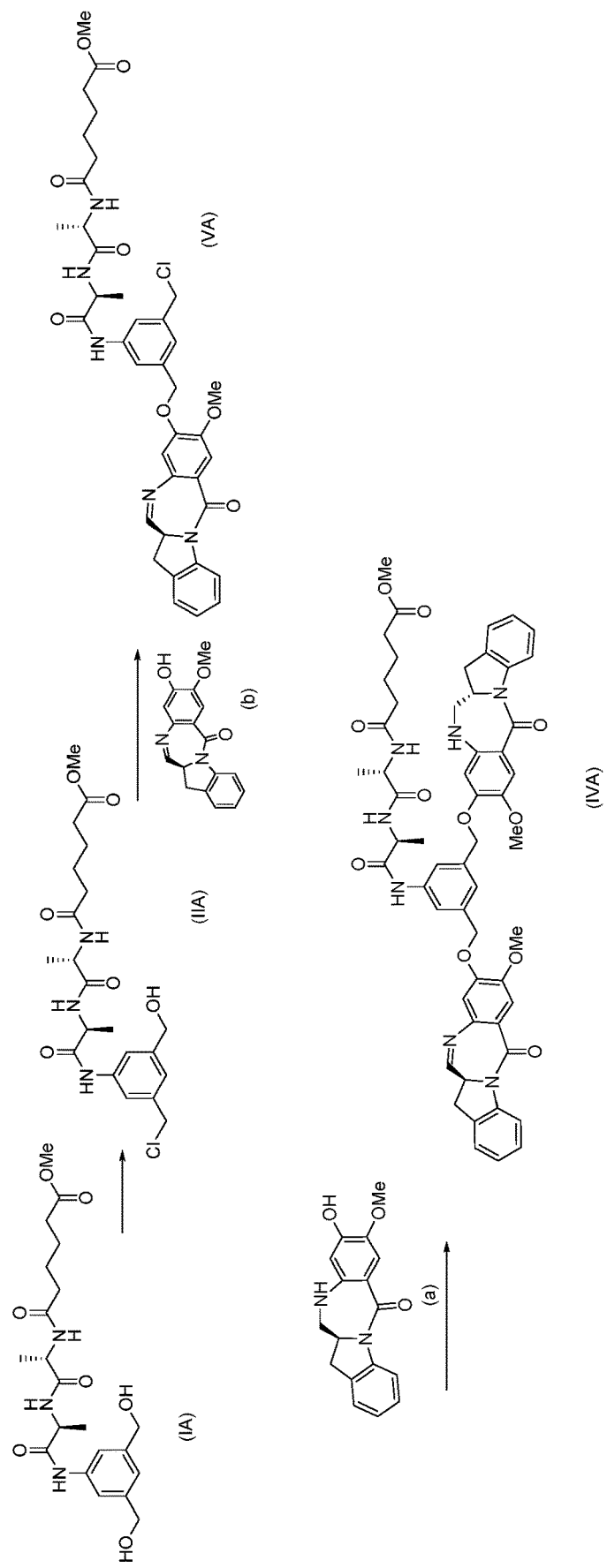
Figure 4:
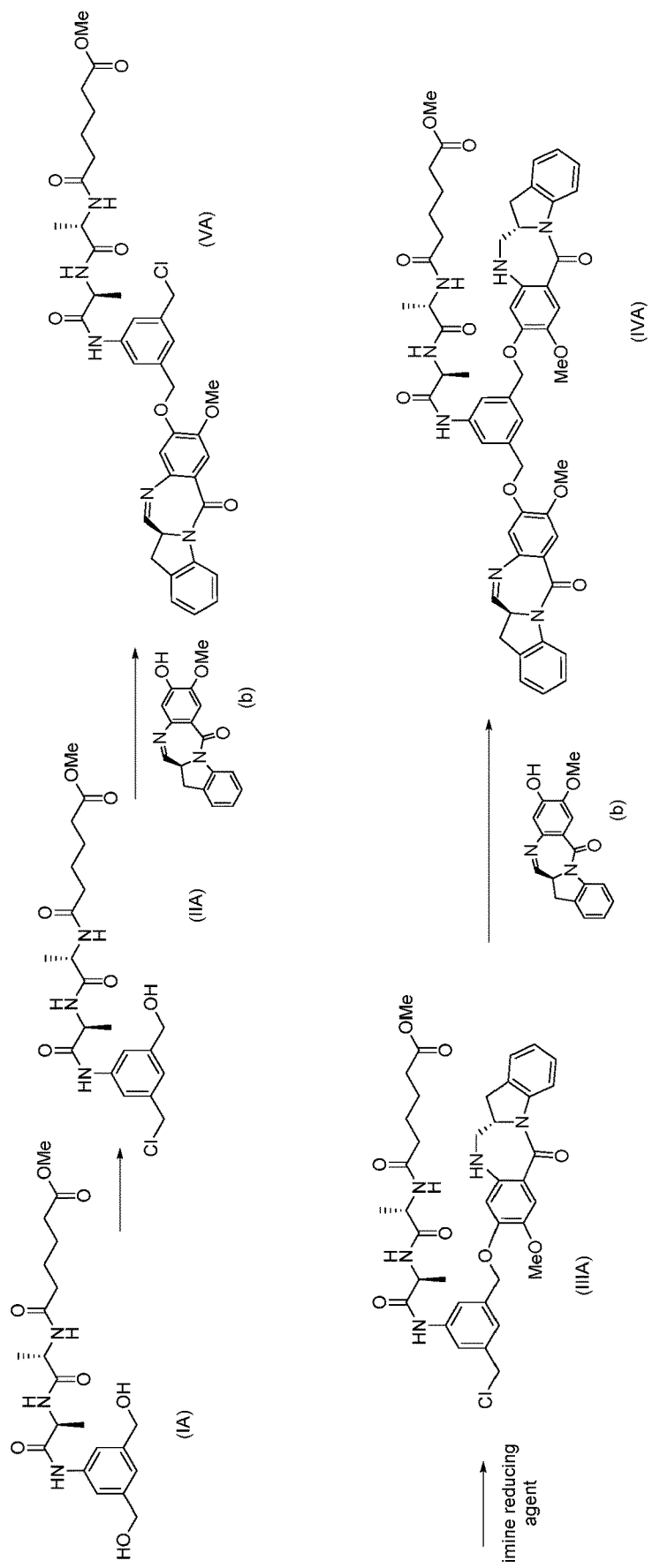
Figure 5:
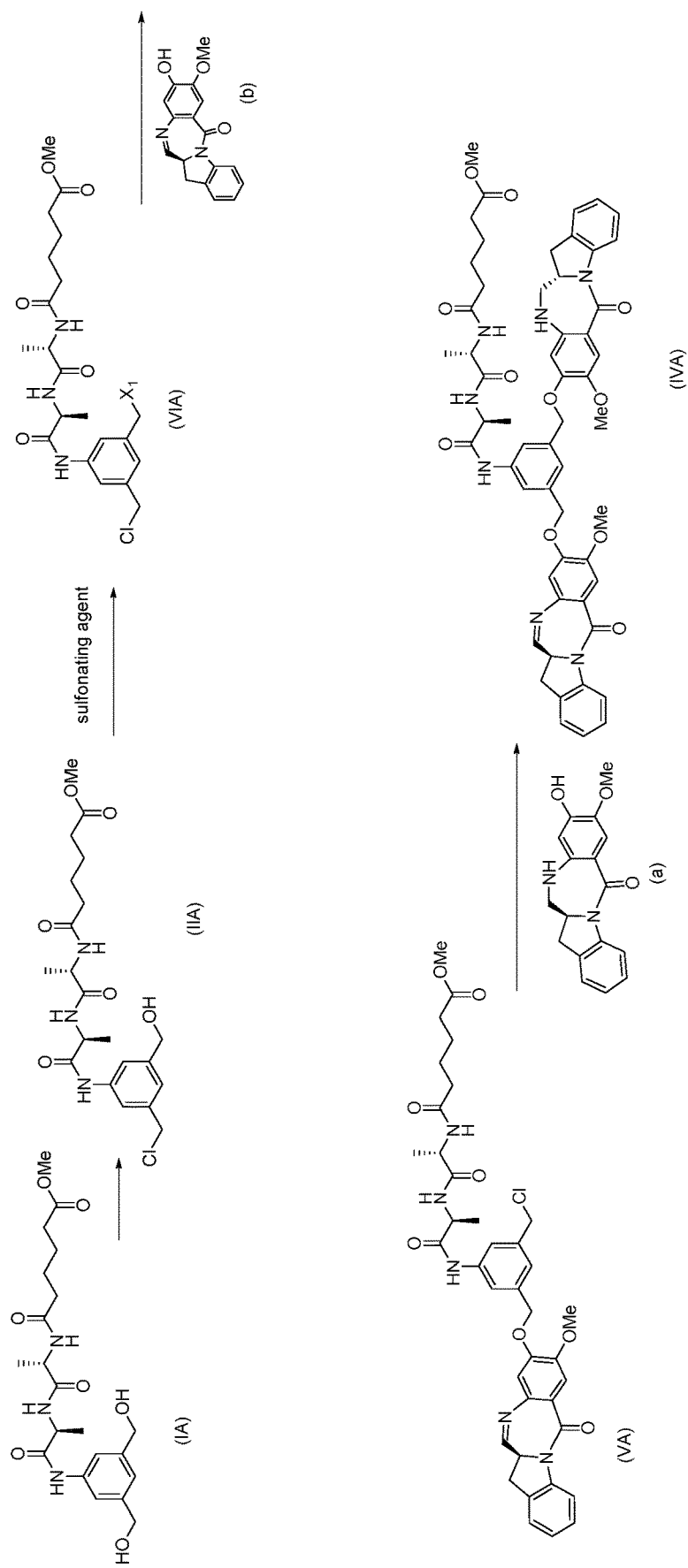
Figure 6:
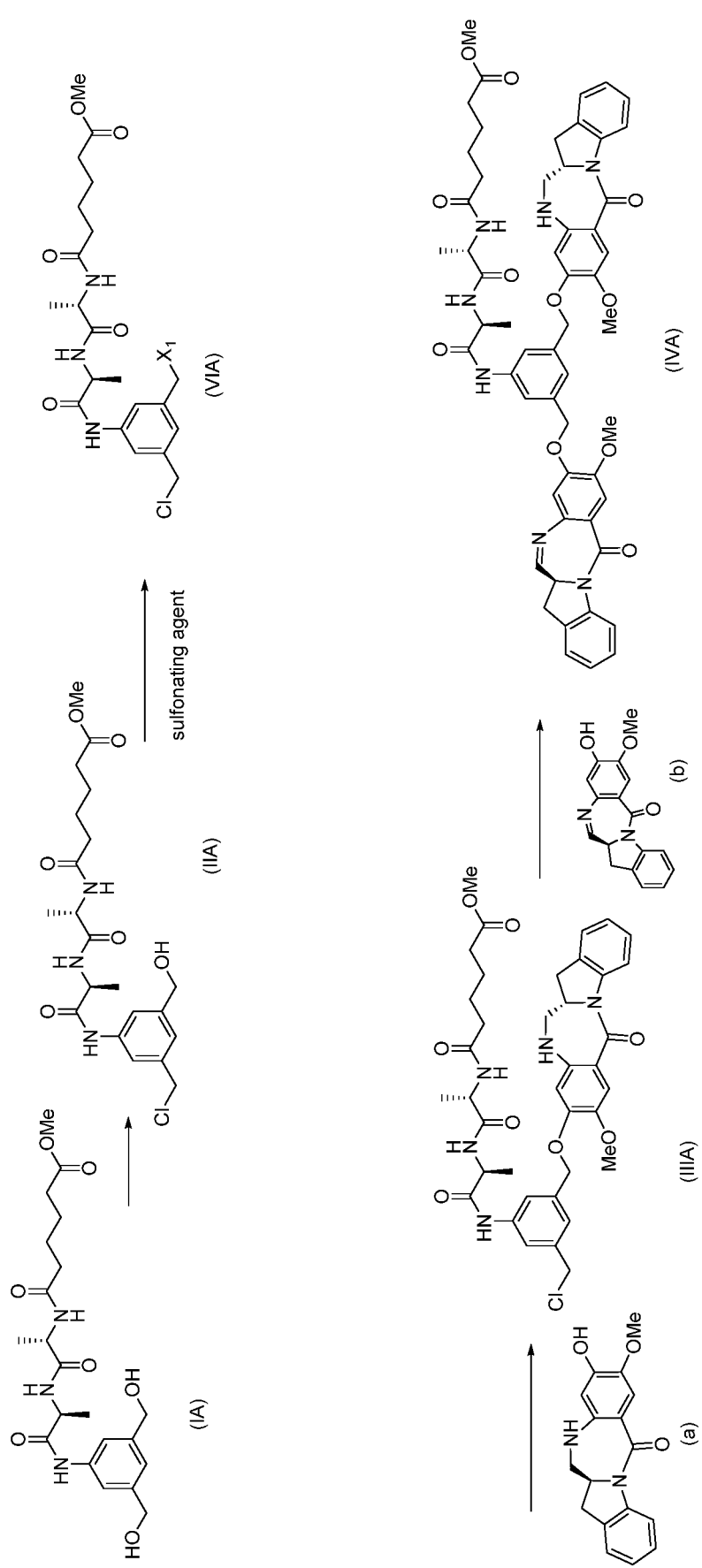
Figure 7:
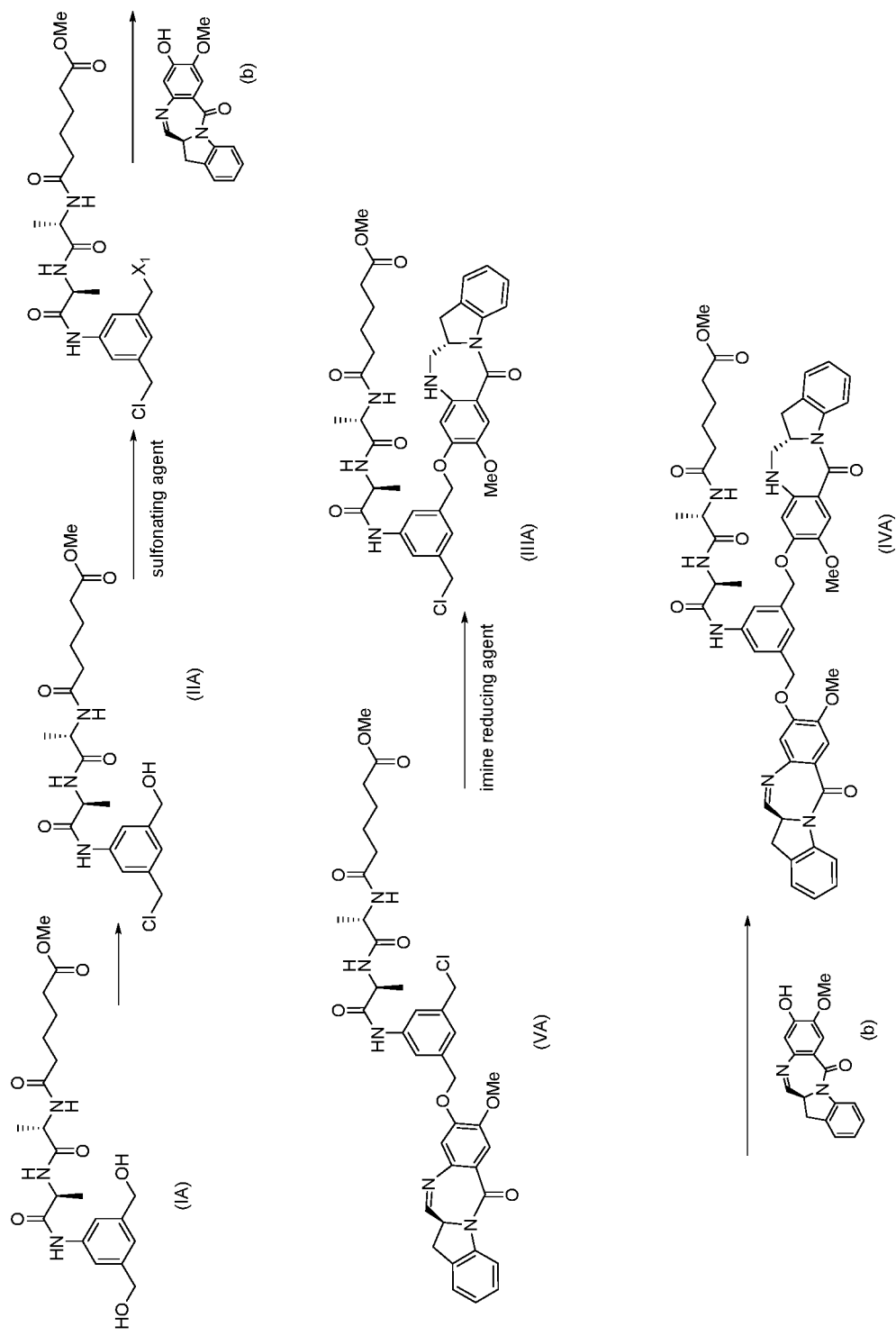
Figure 8:
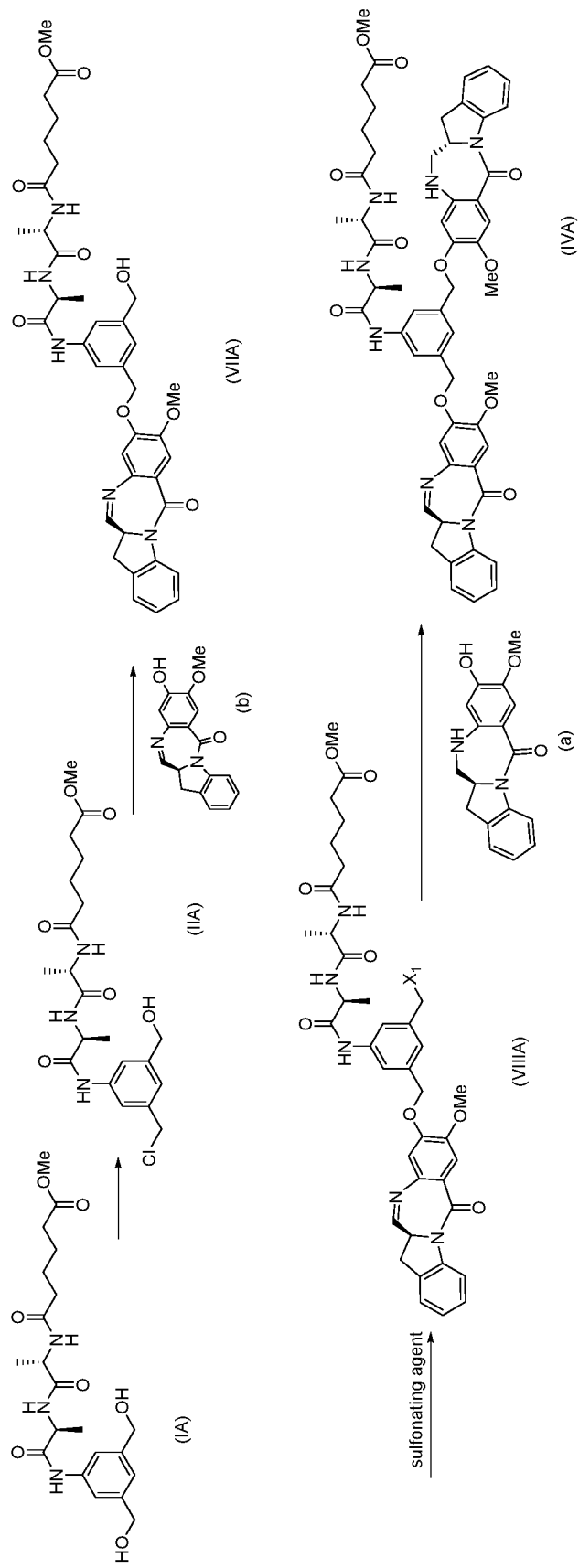
Figure 9:
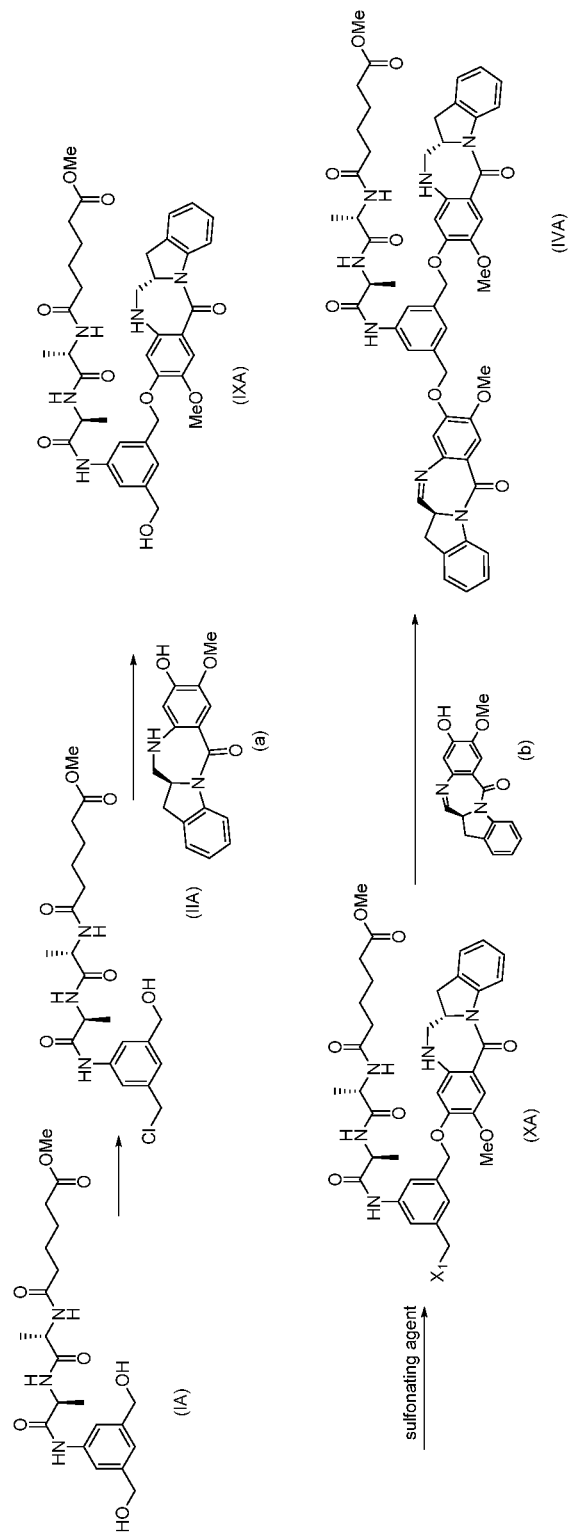
Figure 10:
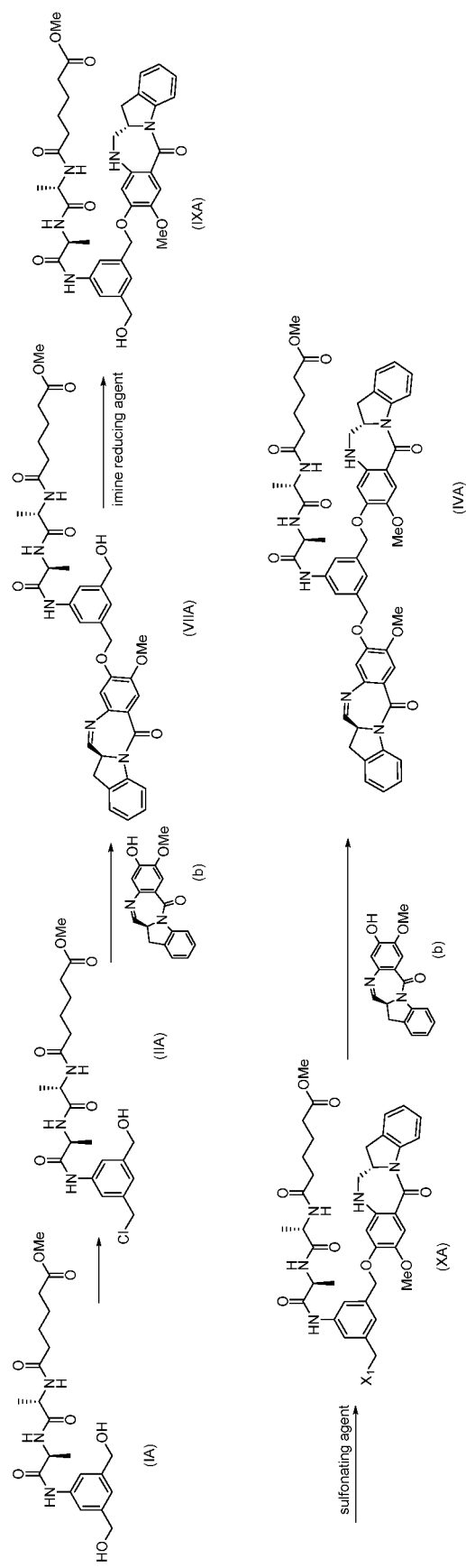
Figure 11:
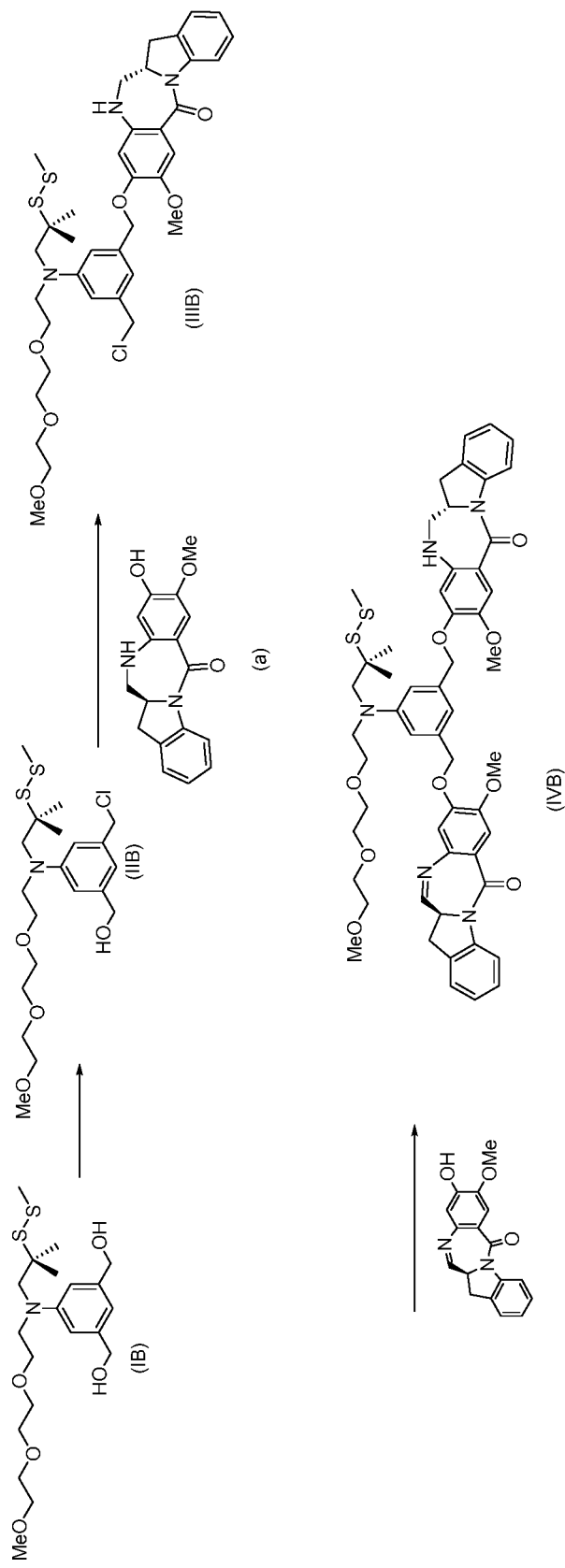
Figure 12:
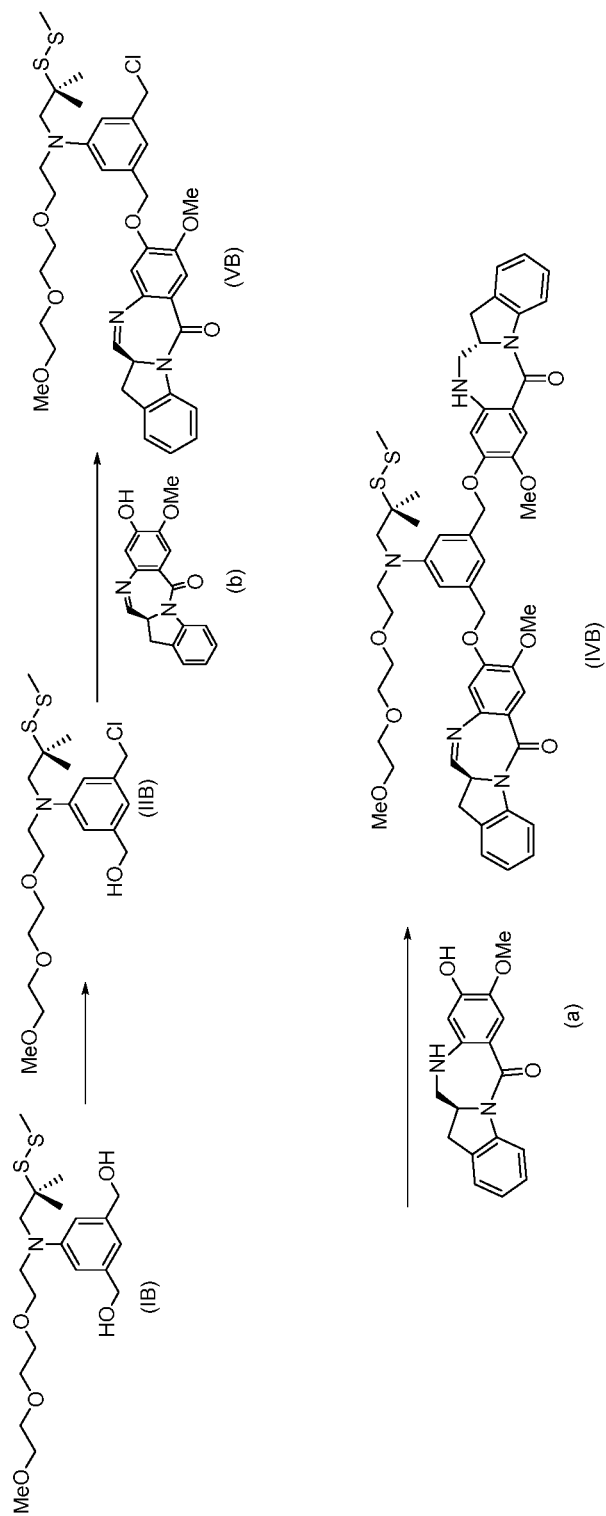
Figure 13:
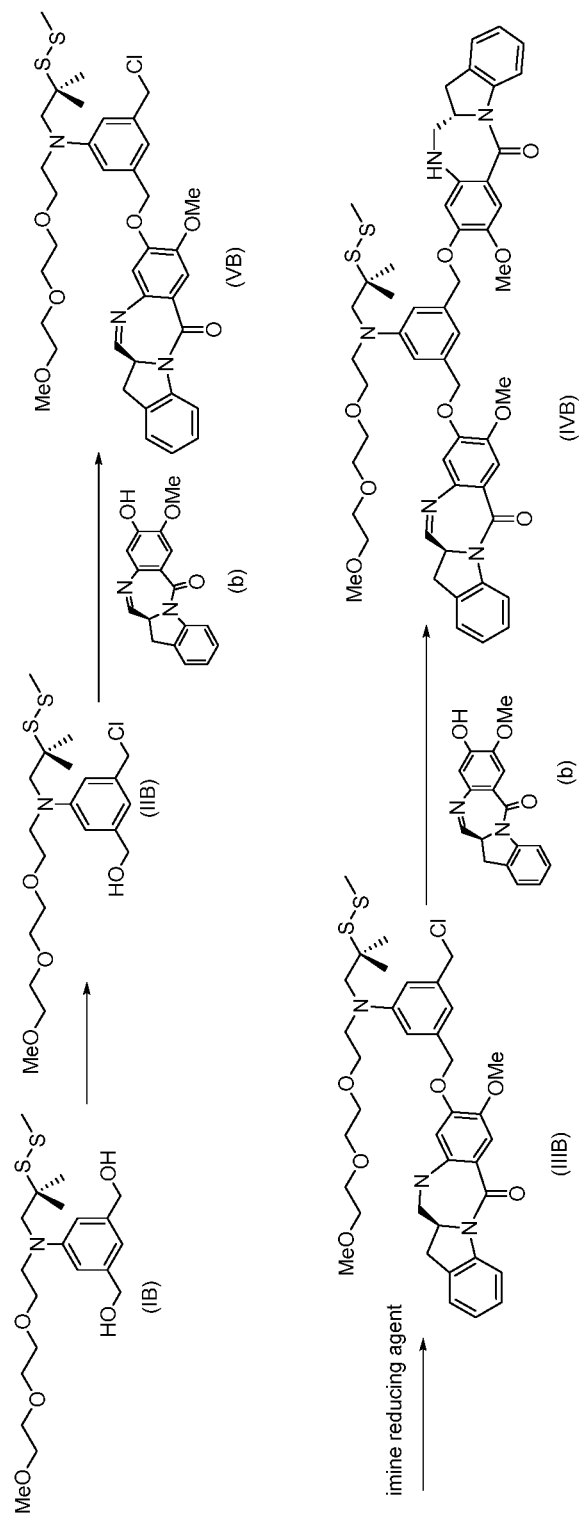
Figure 14:
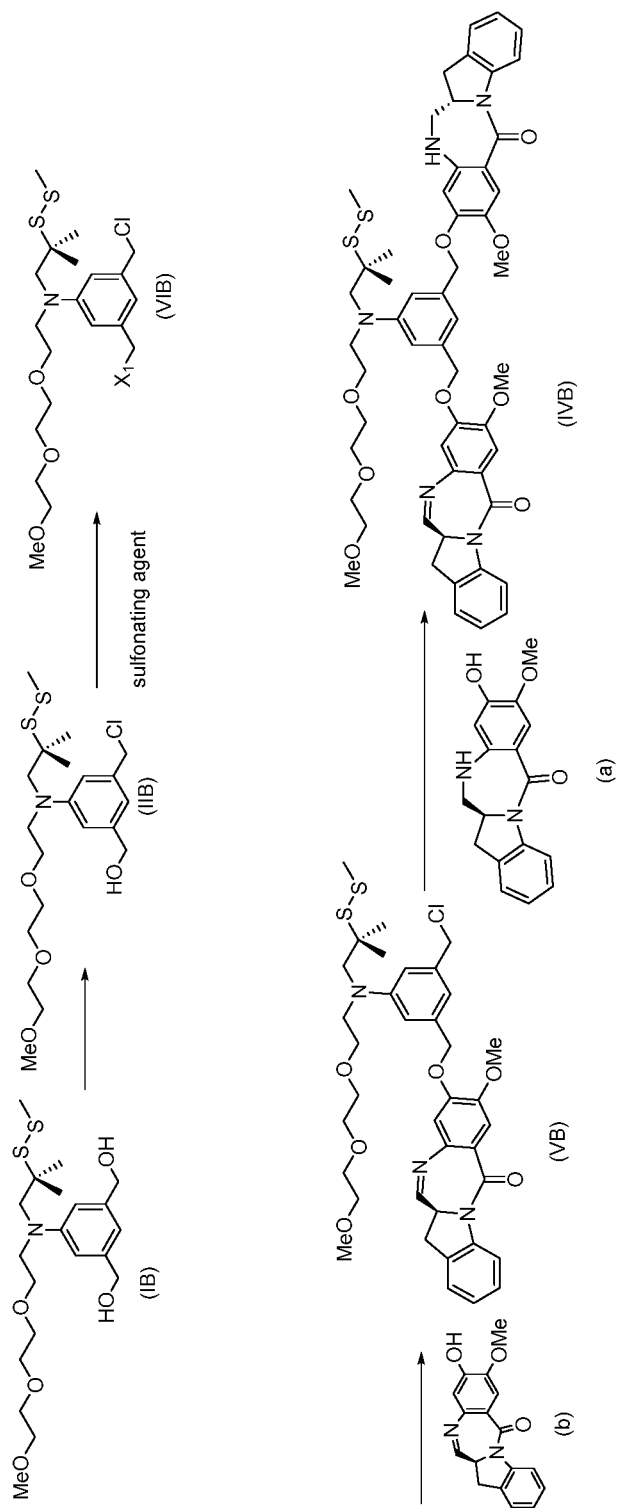
Figure 15:
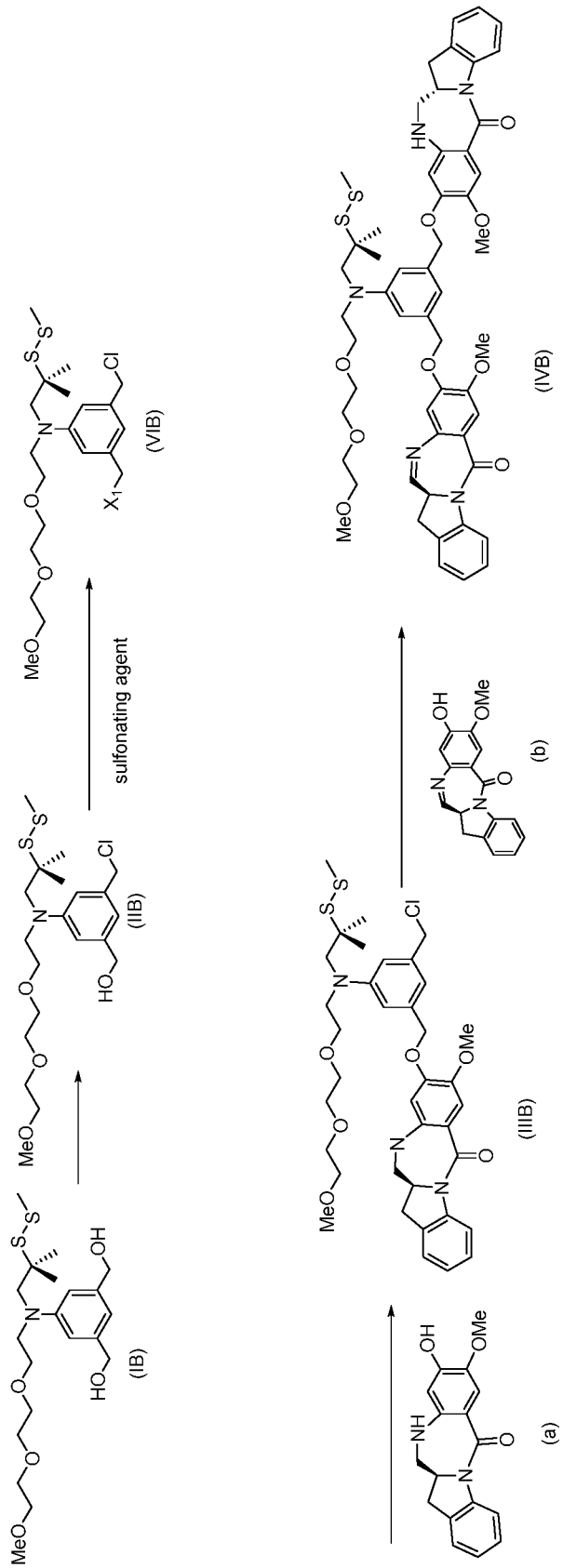
Figure 16:
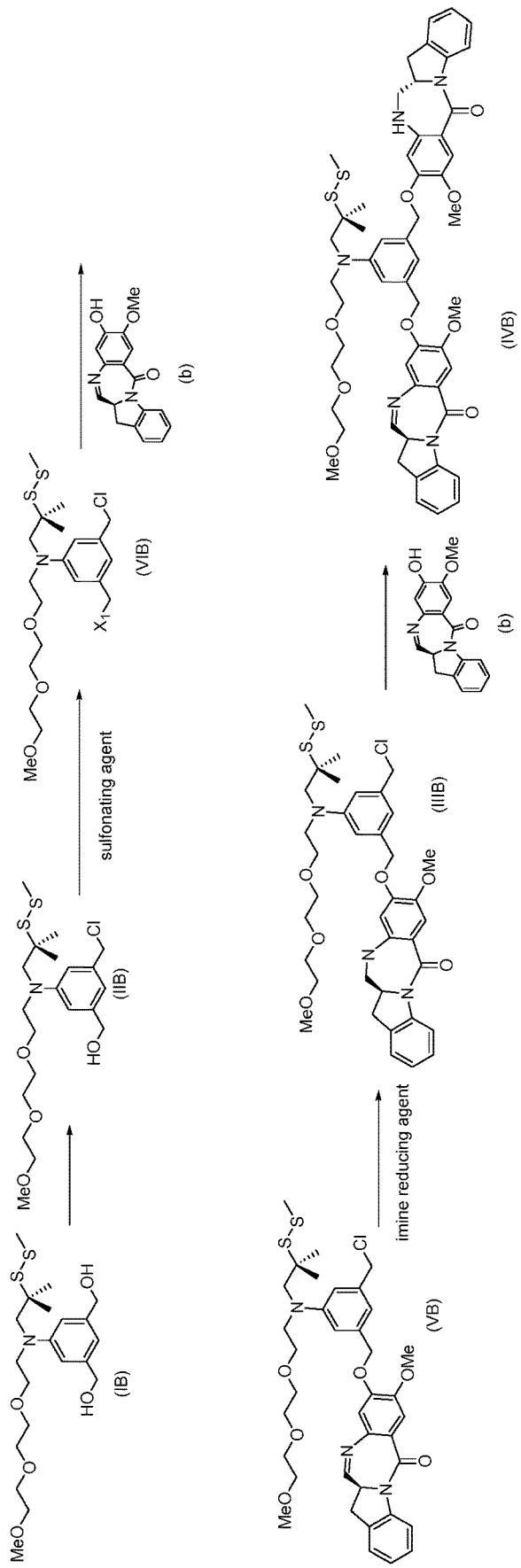
Figure 17:
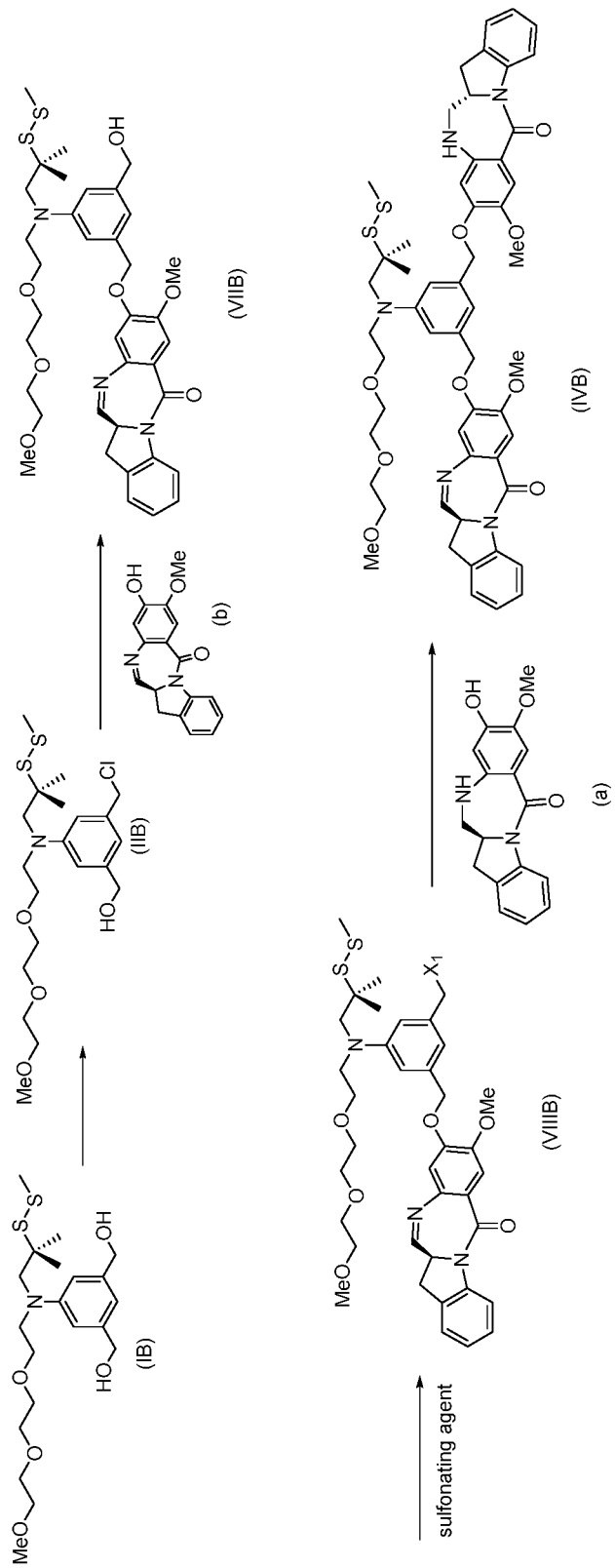
Figure 18:
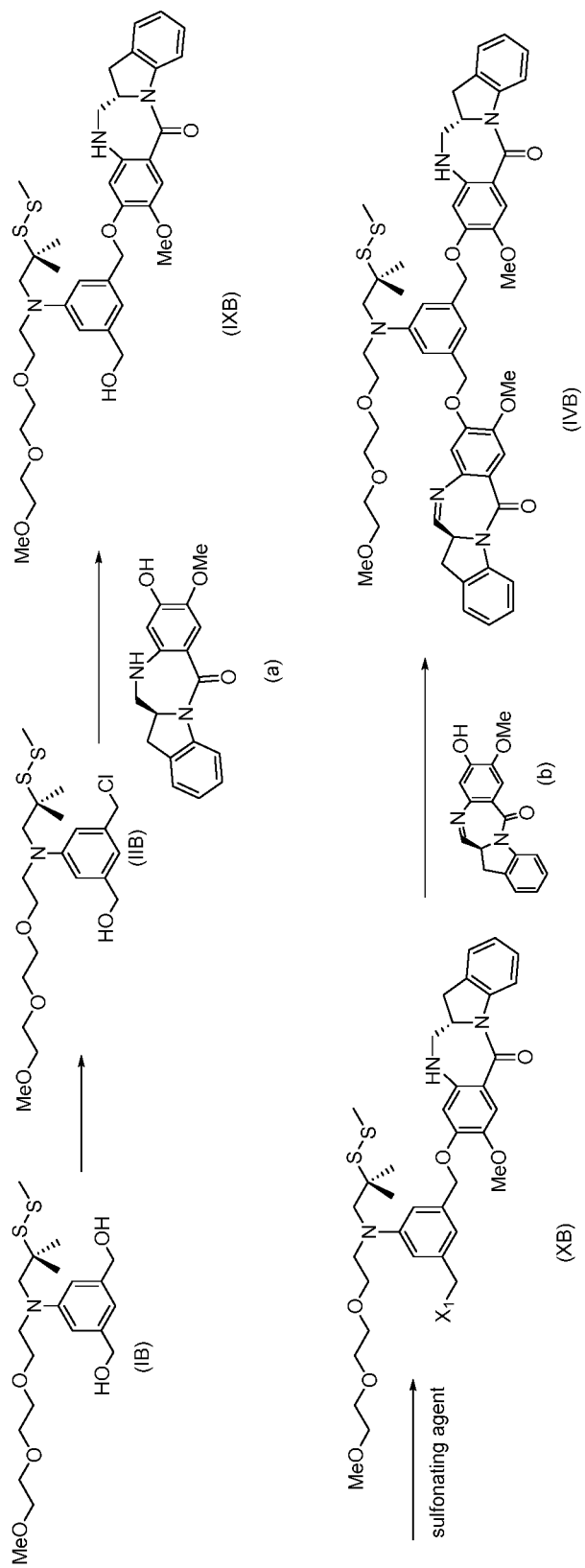
Figure 19:
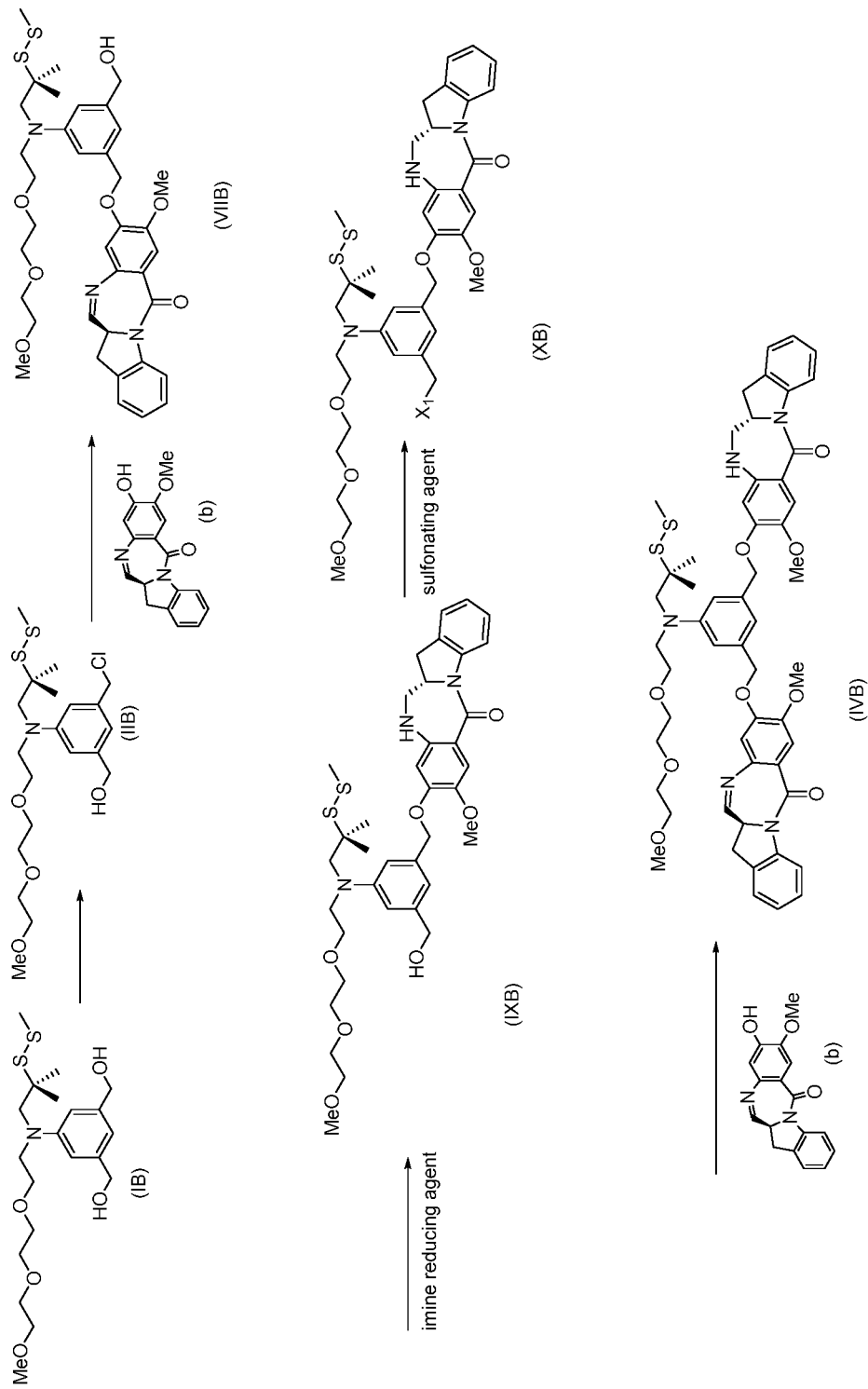

The experiment was repeated with 0.316 g (0.75 eq, 1.71 mmol) or 0.358 g (0.85 eq, 1.94 mmol) cyanuric chloride and HPLC analysis of the reaction mixture is shown in FIG. 1B or FIG. 1C respectively. Similar experiment was also carried out with 0.427 g (1.0 eq., 2.29 mmol) of cyanuric chloride and 1.0 g (1.0 eq., 2.20 mmol) methyl 6-(((S)-1-(((S)-1-((3,5-bis(hydroxymethyl)phenyl)amino)-1-oxopropan-2-yl)amino)-1-oxopropan-2-yl)amino)-6-oxohexanoate (1.0 g, 2.29 mmol, 1.0 eq.). FIG. 1D shows HPLC trace of the reaction mixture. As shown in FIGS. 1A-1D, the use of 0.85 molar equivalents (or eq.) of cyanuric chloride provided the most optimal yield for the monochlorinated product, compound 2.

Example 2. Synthesis of (3-(chloromethyl)-5-((2-(2-(2-methoxyethoxy)ethoxy)ethyl)(2-methyl-2-(methyldisulfanyl)propyl)amino)phenyl)methanol (Compound 4)

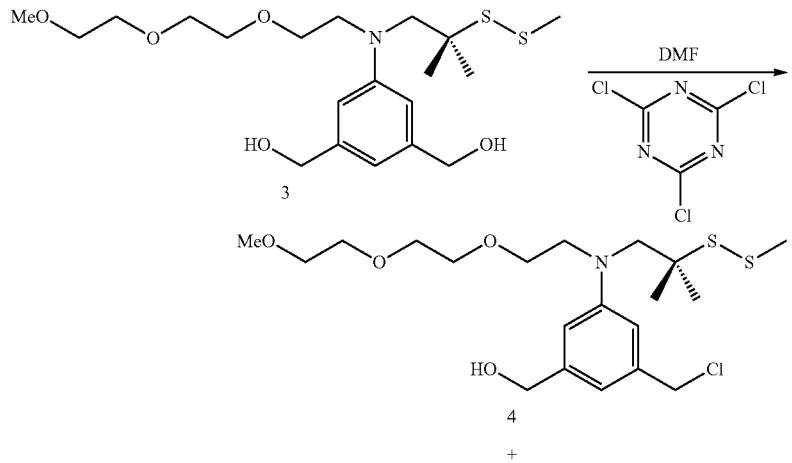

3

4

+

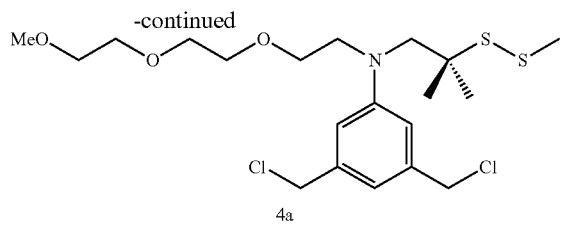

4a (5-((2-(2-(2-methoxyethoxy)ethoxy)ethyl)(2-methyl-2-(methyldisulfanyl)propyl)amino)-1,3-phenylene)dimethanol (compound 3, 5.0911 g, 11.74 mmol, 1.0 eq.) was dissolved in DMF (30 mL, 3.0 vol) in a dry 50 mL round bottom flask and the resulting solution was transferred to a dry 500 mL round bottom flask charged with nitrogen. The 50 mL round bottom flask was rinsed with DMF (2×20.0 mL, 2×2.0 vol) and the solution was added to the 500 mL round bottom flask. The combined DMF solution of compound 3 was stirred for 2 hours at 25±2° C. to obtain a homogenous solution. Cyanuric chloride (1.6557 g, 0.75 eq, 8.805 mmol) was added to a separate dry round bottom flask under nitrogen and DMF (30.0 mL, 3.0 vol) was added to the flask. The resulting mixture was stirred for 30±10 minutes at 3±2° C. to yield yellow-brown suspension, which was then transferred to an addition funnel and added to the DMF solution of compound 3 dropwise at 1 mL/minute while maintaining the temperature at 25±3° C. The resulting reaction mixture was stirred for 20 minutes and the reaction was monitored by HPLC UV analysis. The reaction was deemed to be complete after 50±5 minutes. Ethyl acetate was added to the reaction mixture followed by slow addition of 0.5 M NaOH (25.0 mL, 2.5 vol). The resulting mixture was stirred for 30±5 minutes and then transferred to a separatory funnel. Another portion of ethyl acetate (400 mL, 40 vol) was added to the separatory funnel followed by an addition of deionized water (100 mL, 10 vol). Separate the organic phase and the aqueous phase and if the aqueous phase has a pH<4, the organic phase was then washed with 0.5 M NaOH again. The organic phase was washed with water (2×100 mL, 2×10 vol) and then concentrated. The crude product was purified by silica gel column chromatography eluted with a gradient of 5-55% ethyl acetate/hexane over 40 minutes followed by an increase to 100% ethyl acetate in 5 minutes. The desired product, compound 4, eluted between 47% and 53% ethyl acetate. The product containing fractions were combined and concentrated to afford the desired product (2.96 g, 56%).

Similar experiments were carried out with 0.65 eq., 0.85 eq. or 1 eq. of cyanuric chloride. The reaction yields of the desired product are listed below:

| Equivalents | Compd 3 | Compd 4 | Compd 4a | Isolated Yield |
|---|---|---|---|---|
| 0.65 | 41 | 42 | 14 | 41.3% |
| 0.85 | 14 | 51 | 34 | 40.3% |
| 1.0 | 17 | 49 | 33 | 40.3% |

Example 3. Synthesis of Compound 5

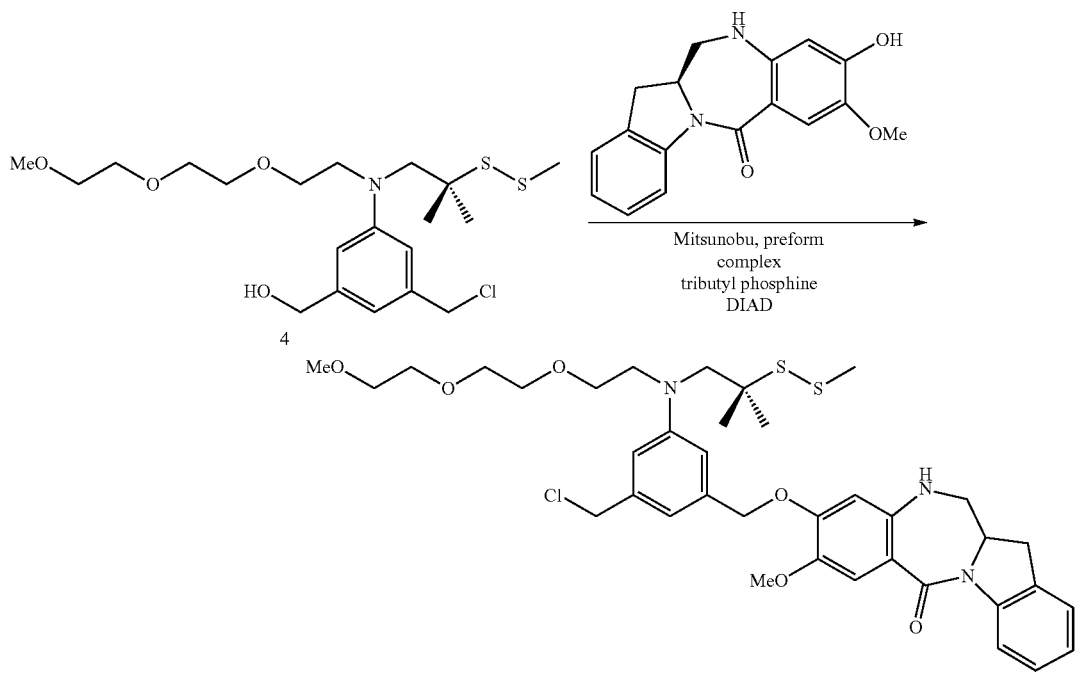

5

In a dry 100 mL round bottom flask equipped with a stir bar and thermocouple was added tetrahydrofuran (10.0 mL, 20 vol) under nitrogen followed by cooling to 5±3° C. Tri-n-butylphosphine (0.332 mL, 1.32 mmol) was added followed by the dropwise addition of diisopropyl azodicarboxylate (0.261 mL, 1.32 mmol) via an addition funnel over 10±2 minutes. The resulting mixture was stirred at 5±3° C. for 2 hours. In a separate dry 100 mL round bottom flask was added (S)-9-hydroxy-8-methoxy-11,12,12a,13-tetrahydro-6H-benzo[5,6][1,4]diazepino[1,2-a]indol-6-one (0.328 g, 1.10 mmol, 1.00 eq.) followed by the addition of tetrahydrofuran (10.0 mL, 20 vol). The resulting mixture was stirred under nitrogen at 20° C.±5° C. to obtain a slightly cloudy solution. To the solution was added (3-(chloromethyl)-5-((2-(2-(2-methoxyethoxy)ethoxy)ethyl)(2-methyl-2-(methyldisulfanyl)propyl)amino)phenyl)methano (0.5 g, 1.10 mmol) and the resulting mixture was stirred at 20° C.±5° C. to obtain a slightly cloudy solution, which was cooled to 5±3° C. and added via addition funnel dropwise over 10±2 minutes while maintaining temperature at 5±3° C. to the round bottom flask containing tri-n-butylphosphine and diisopropyl azodicarboxylate mixture. The resulting reaction mixture was stirred overnight while slowly warming to 20° C.±5° C. from 16 to 24 hours. The reaction was monitored by HPLC analysis and the reaction was deemed to be complete when ≥60% of the starting material was converted to the product. Upon completion of the reaction, potassium carbonate supported silica gel (1.0 g) was added to the reaction mixture, stirred for 30±5 min and filtered to remove the solid. The filtrate was concentrated to dryness and re-dissolved in dichloromethane (3.0 mL, 6 vol). The crude product was purified via silica gel column chromatography eluted with a gradient of 0-100% ethyl acetate/hexanes over 40 minutes. Fractions containing the pure product were combined and concentrated to dryness to afford desired product 5 (0.140 g, 17.3% yield). The reaction yield is due to the inaccurate weight of starting material 4 because it contained DMF.

Example 4. Synthesis of Compound 8

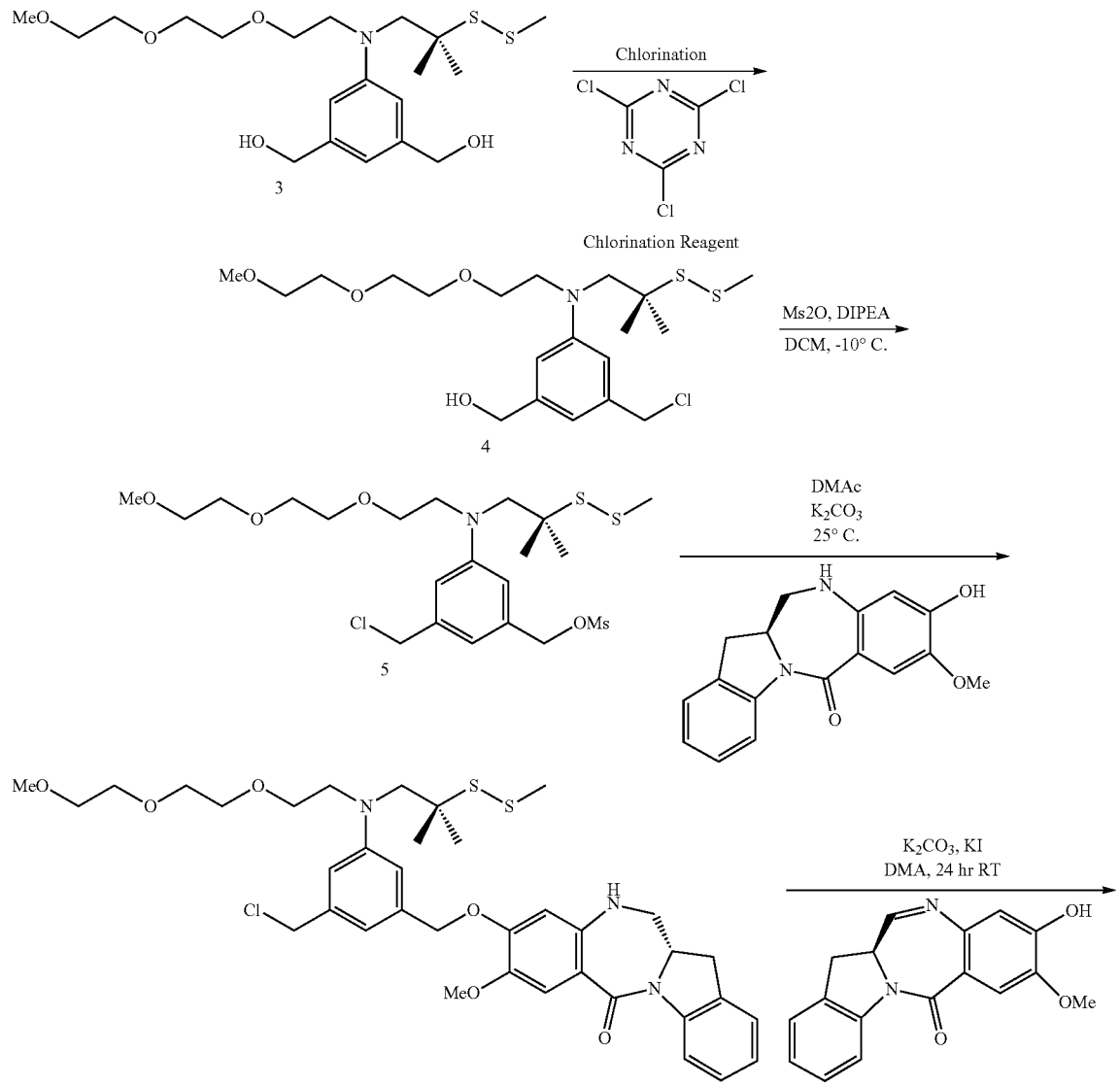

-continued

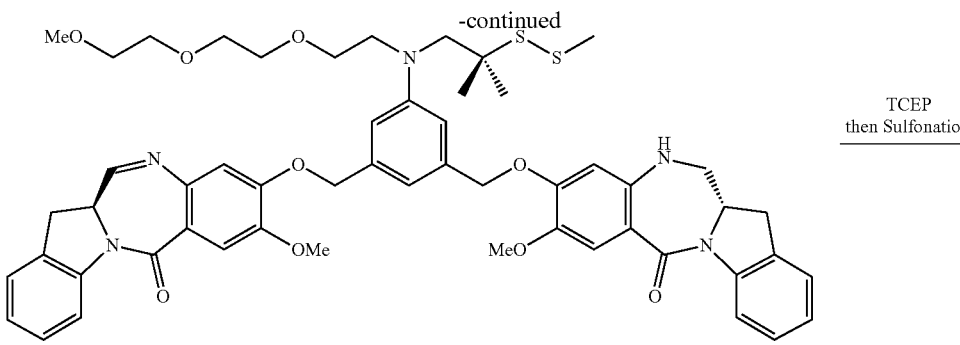

7

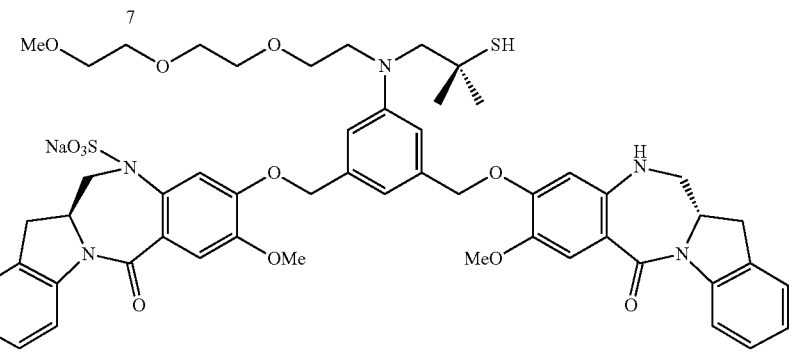

8

Step 1.

A dry 250 mL round bottom flask (RBF) equipped with a stir bar and thermocouple was charged with nitrogen slowly. In a dry 50 mL round bottom flask, 10.12 g (22.26 mmol) of (5-((2-(2-(2-methoxyethoxy)ethoxy)ethyl)(2-methyl-2-(methyldisulfanyl)propyl)amino)-1,3-phenylene)dimethanol (compound 3) was dissolved in DMF (40 mL, 4.0 vol). The resulting solution was transferred into the 500 mL RBF. The 50 mL RBF containing compound 3 was rinsed with DMF (30.0 mL, 3.0 vol) and the solution was added to the 500 mL RBF. The solution in the 500 mL RBF was agitated at 600 rpm for over 1 hour at 25±2° C. to obtain a homogenous suspension. In a separate dry 100 mL RBF was added 3.14 g (16.70 mmol) of 2,4,6-trichloro-1,3,5-triazine (TCT). The RBF was charged with nitrogen and 20.0 mL (2.0 vol) of DMF was added. The resulting mixture was agitated for 30±5 minutes at 3±2° C. to form a solution, which was transferred to an additional funnel and added to the 500 mL RBF dropwise over 20±3 minutes while maintaining temperature at 25±3° C. The resulting reaction mixture was stirred for 50±5 minutes. Upon completion of the reaction, ethyl acetate (100.0 mL, 10 vol) was added into the reaction via the additional funnel to quench the reaction followed by an addition of 0.5M NaOH (50.0 mL, 5 vol) while maintaining the reaction temperature below 30° C. The resulting mixture was stirred for 30±5 min and transferred into a separatory funnel. An additional 800 mL (80 vol) of ethyl acetate was added to the separatory funnel followed by 100 mL (10 vol) of deionized water. The organic phase was separated and washed with water (2×200.0 mL, 2×20 vol). The combined organic phase was concentrated using rotary evaporator. The crude product was purified using silica gel column chromatography eluted with a gradient of 0-55% ethyl acetate/hexanes over 40 minutes then increased to 100% ethyl acetate over 5 minutes to give the desired product (3-(chloromethyl)-5-((2-(2-(2-methoxyethoxy)ethoxy)ethyl)(2-methyl-2-(methyldisulfanyl)propyl)amino)phenyl)methanol (compound 4) (4.9429 g, 10.72 mmol, 48.1% yield).

Step 2

Compound 4 (4.0788 g, 8.81 mmol) was dissolved in dichloromethane (20.0 mL, 5 vol). The resulting clear yellow solution was cooled to −10° C. and methanesulfonic anhydride (4.90 g, 27.3 mmol) was added. N-ethyl-N-isopropylpropan-2-amine (9.23 ml, 52.9 mmol) was dissolved in the dichloromethane (20.0 mL, 5 vol) and the resulting solution was added to the mixture of compound 4 and methanesulfonic anhydride slowly while maintaining the reaction temperature at −10° C. After 15 minutes, the reaction was quenched by adding a 1:1 mixture of ice water and methanol (20.0 mL, 5 vol) and stirred at 1000 rpm for 5 minutes at −10° C. The mixture was then added to pre-cooled (5° C.) water (36.0 mL, 9.0 vol) and stirred at −10° C. followed by addition of aqueous methane sulfonic acid (5% soln., 10.0 mL, 2.5 vol). The resulting solution was stirred at 0° C. for 5 minutes, DCM (16.0 mL, 40.0 vol) was added, and the mixture was stirred for 1 minute. The organic layer was separated and returned back to the reaction reactor and pre-cooled (5° C.) water (36.0 mL, 9.0 vol) and aqueous methane sulfonic acid (5% soln., 13.2 mL, 3.3 vol) was added to the reactor. The mixture was stirred for 8 minutes and the organic layer was separated and washed with ice/water (2×42.7 mL, 2×10.5 vol). The combined organic layers were dried with anhydrous sodium sulfate, filtered and the solvent was removed in a vacuum oven to afford desired product 3-(chloromethyl)-5-((2-(2-(2-methoxyethoxy)ethoxy)ethyl)(2-methyl-2-(methyldisulfanyl)propyl)amino)benzylmethane sulfonate (compound 5) (4.8740 g, 8.81 mmol, 100% yield).

Step 3

(S)-9-hydroxy-8-methoxy-11,12,12a,13-tetrahydro-6H-benzo[5,6][1,4]diazepino[1,2-a]indol-6-one (compound 5) (0.124 g, 0.418 mmol) and N,N-dimethylacetamide (1.0 mL, 4 vol) were added in a 100 mL RBF equipped with a stir bar and a thermocouple and the solution was sonicated. Potassium carbonate (0.114 g, 0.828 mmol) was added to the solution. In a 20 mL glass vial, compound 5 (0.2263 g, 0.414 mmol) was dissolved in N,N-dimethylacetamide (1.5 mL, 6 vol) and the resulting solution was added slowly to the 100 mL RBF reaction vessel over an hour. The reaction mixture was stirred at 800 rpm for 11 hours while maintaining the reaction temperature at 20° C.±3° C. Water (3 mL, 10 vol) was added slowly and stirred for 15±5 minutes to quench the reaction. Ethyl acetate (9 mL, 30 vol) was then added to the reaction mixture and stirred for 15±5 minutes. The resulting mixture was transferred to a separatory funnel and the organic phase was isolated. The aqueous layer was washed with ethyl acetate (3×12 mL, 3×40 vol). The combined organic layers were washed with semi-saturated brine solution (1×9 mL, 1×30 vol) and concentrated to yield the crude product. The crude product was purified by silica gel column chromatography eluted with a gradient of 0-70% ethyl acetate/hexane over 35 minutes to afford the desired product (S)-9-((3-(chloromethyl)-5-((2-(2-(2-methoxyethoxy)ethoxy)ethyl)(2-methyl-2-(methyldisulfanyl)propyl)amino)benzyl)oxy)-8-methoxy-11,12,12a,13-tetrahydro-6H-benzo[5,6][1,4]diazepino[1,2-a]indol-6-one (compound 6) (0.1549 g, 0.212 mmol, 51.2% yield).

Step 4

In a dry 50 mL round bottom flask (RBF) equipped with a stir bar, thermocouple and heating mantel was charged (S)-9-((3-(chloromethyl)-5-((2-(2-(2-methoxyethoxy)ethoxy)ethyl)(2-methyl-2-(methyldisulfanyl)propyl)amino)benzyl)oxy)-8-methoxy-11,12,12a,13-tetrahydro-6H-benzo[5,6][1,4]diazepino[1,2-a]indol-6-one (0.150 g, 0.195 mmol). N,N-dimethylacetamide (3.0 mL, 6 vol) was added and the resulting mixture was stirred at 20° C.±5° C. to obtain a clear light brown solution. To the light brown solution was added potassium iodide (0.032 g, 0.195 mmol) followed by potassium carbonate (0.054 g, 0.390 mmol). In a 20 mL glass vial, (S)-9-hydroxy-8-methoxy-12a,13-dihydro-6H-benzo[5,6][1,4]diazepino[1,2-a]indol-6-one (0.071 g, 0.234 mmol) was dissolved in N,N-dimethylacetamide (2.0 mL, 4 vol). The resulting solution was added to the reaction mixture in RBF slowly and the reaction solution turned to brownish yellow. The reaction mixture was stirred for 24 hours with heating at 30° C.±3° C. and then cooled to 20° C.±5° C. Deionized water (6 mL, 20 vol) was added to the reaction mixture to quench the reaction and precipitate out the product. The product was filtered, washed with deionized water (2×3 mL, 10 vol) and re-dissolved in dichloromethane (12 mL, 40 vol). The dichloromethane solution was mixed with deionized water (6 mL, 20 vol) and the organic phase was separated, washed with semi-saturated brine (2×6 mL, 2×20 vol) and water (2×6 mL, 2×20 vol). The organic phase was dried over anhydrous sodium sulfate, filtered and concentrated under vacuum to about 0.45 mL (1.5 vol). The crude product is purified via silica gel column chromatography eluting with a gradient of 0-100% ethyl acetate/hexanes over 50 minutes then increase to 100% ethyl acetate in 5 minutes to yield the desired product (S)-8-methoxy-9-((3-((((S)-8-methoxy-6-oxo-11,12,12a,13-tetrahydro-6H-benzo[5,6][1,4]diazepino[1,2-a]indol-9-yl)oxy)methyl)-5-((2-(2-(2-methoxyethoxy)ethoxy)ethyl)(2-methyl-2-(methyldisulfanyl)propyl)amino)benzyl)oxy)-12a,13-dihydro-6H-benzo[5,6][1,4]diazepino[1,2-a]indol-6-one (0.1033 g, 0.105 mmol, 53.6% yield).

Step 5

TCEP (3.1 g) was wetted with a few drops of water. Saturated NaHCO₃ (85 mL) was added until pH 6.5 was reached. 0.1 M phosphate buffer (34 mL) was freshly prepared and adjusted to pH 6.5 and then added to the TCEP solution. Compound 7 (10.1 g) was dissolved in acetonitrile (588 mL) and MeOH (257 mL) and mixed with the TCEP solution. After 2 h, additional TCEP (310 mg) was added (dissolved in NaHCO₃-solution and pH adjusted to 6.5) and the mixture stirred for further 2 h. DCM (1.3 L) and water (600 mL) were added. After separation, the aqueous phase was extracted with DCM (250 mL). The combined organic phases were washed with water (2×250 mL) and evaporated to dryness to yield 9.6 g of reduced compound.

The reduced compound (9.5 g) was suspended under argon in 2-propanol (522 mL) and water (261 mL) at room temperature. Sodium-bisulfite (6.78 g) was added as a solid to the above suspension. The mixture was stirred at room temperature for 1 h whereupon a clear solution was obtained. The yellowish solution was filtered. The resulting solution was then diluted with water (500 mL) and portioned into two equal portions of 593 g each. These were transferred to 3 L round bottom flasks, frozen in a dry-ice bath and lyophilized until a dry powder was obtained (flasks were kept at ambient temperature during lyophilization). The fractions yielded 7.2 g and 7.4 g of compound 8, respectively, as an off-white lyophilized powder.

The invention claimed is:

1. A method of preparing a compound of formula (IIA):

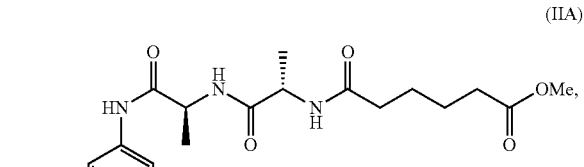

(IIA)

comprising reacting a compound of formula (IA):

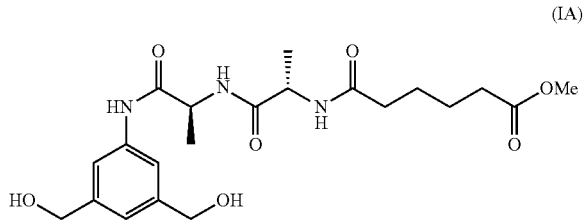 [SMILES: COC(=O)CCCCC(=O)N[C@@H](C)C(=O)N[C@@H](C)C(=O)Nc1cc(CO)cc(CO)c1]

(IA)

with cyanuric chloride to form the compound of formula (IIA).

2. The method of claim 1, wherein 0.6 to 1.0 molar equivalent of cyanuric chloride relative to the compound of formula (IA) is used.

3. The method of claim 2, wherein between 0.7 and 0.8 molar equivalent of cyanuric chloride is used.

4. The method of claim 2, wherein 0.75 molar equivalent or 0.85 molar equivalent of cyanuric chloride is used.

5. The method of claim 1, wherein the reaction is carried out in DMF.

6. The method of claim 1, wherein the method further comprises reacting the compound of formula (IIA) with a compound of formula (a):

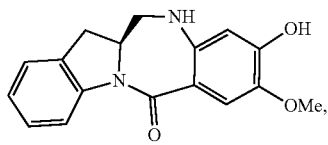

to form a compound of formula (IIIA):

(IIIA)

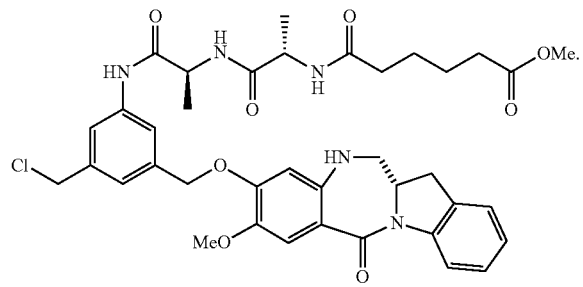

7. The method of claim 6, wherein the method further comprises reacting the compound of formula (IIIA) with a compound of formula (b):

(b)

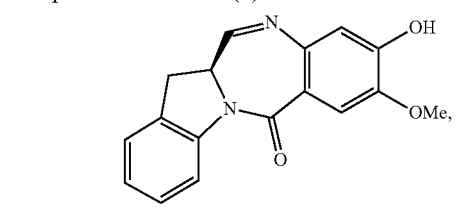

to form a compound of formula (IVA):

(IVA)

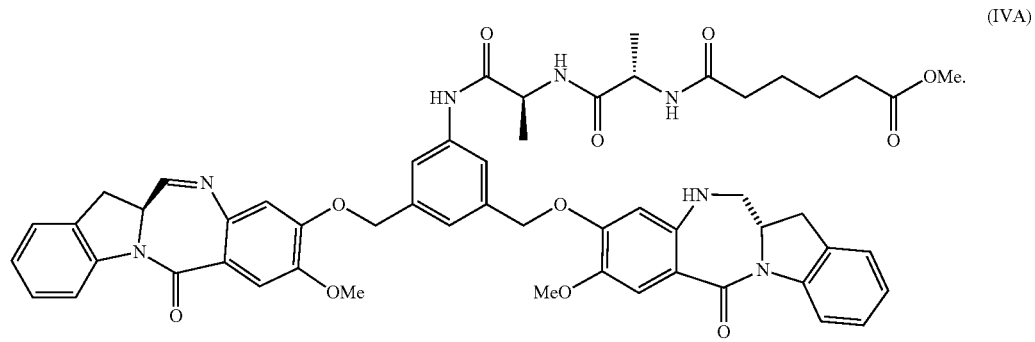 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

8. The method of claim 6, wherein the reaction between the compound of formula (IIA) and the compound of formula (a) is carried out in the presence of an alcohol activating agent and an azodicarboxylate.

9. The method of claim 8, wherein the alcohol activating agent is tributylphosphine or triphenylphosphine and the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD).

10. The method of claim 8, wherein the alcohol activating agent is triphenylphosphine and the azodicarboxylate is diisopropyl azodicarboxylate (DIAD).

11. The method of claim 10, wherein the triphenylphosphine and diisopropyl azodicarboxylate are mixed together first to form an triphenylphosiphosphine-azodicarboxylate complex before mixing the complex with the compound of formula (IIA) and the compound of formula (a).

12. The method of claim 7, wherein the compound of formula (IIIA) is reacted with the compound of formula (b) in the presence of a base.

13. The method of claim 12, wherein the base is sodium carbonate, potassium carbonate, cesium carbonate, sodium hydride, or potassium hydride.

14. The method of claim 13, wherein the base is potassium carbonate.

15. The method of claim 7, wherein the reaction between the compound of formula (IIIA) and the compound of formula (b) is carried out in the presence of potassium iodide or cesium iodide.

16. The method of claim 1, wherein the method further comprises the steps of:

i) reacting the compound of formula (IIA) with a sulfonating agent to form a compound of formula (VIA):

(VIA)

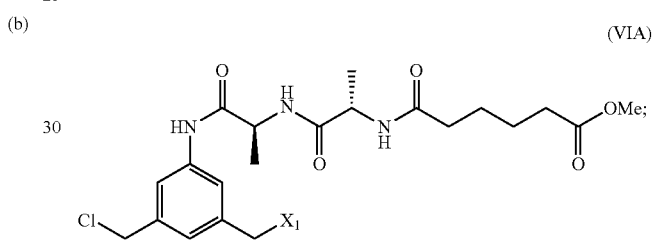

ii) reacting the compound of formula (VIA) with a compound formula (b):

(b)

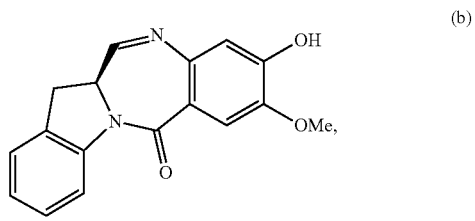 [SMILES: COc1cc2c(cc1O)N=C[C@@H]1Cc3ccccc3N1C2=O]

to form the compound of formula (VA):
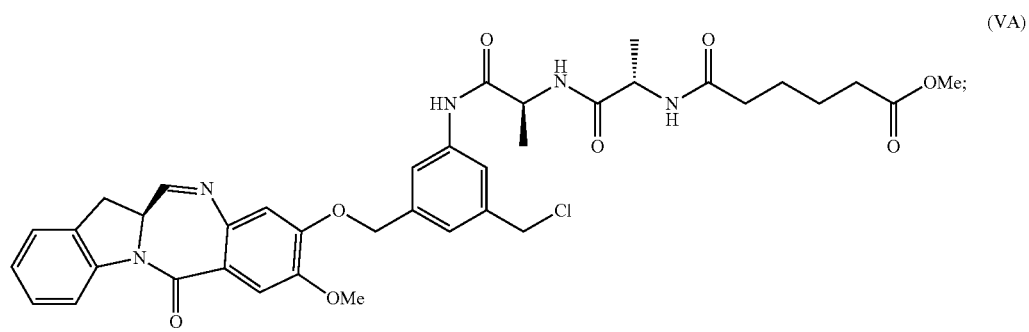 [SMILES: COC(=O)CCCCC(=O)N[C@@H](C)C(=O)N[C@@H](C)C(=O)Nc1cc(CCl)cc(COc2cc3c(cc2OC)C(=O)N2c4ccccc4C[C@H]2C=N3)c1]
(VA)
iii) reacting the compound of formula (VA) with a compound of formula (a):
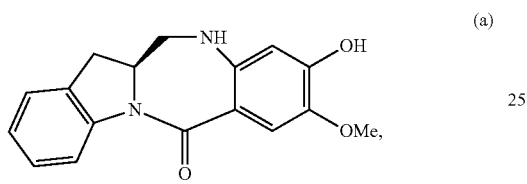
(a)
to form a compound of formula (IVA):
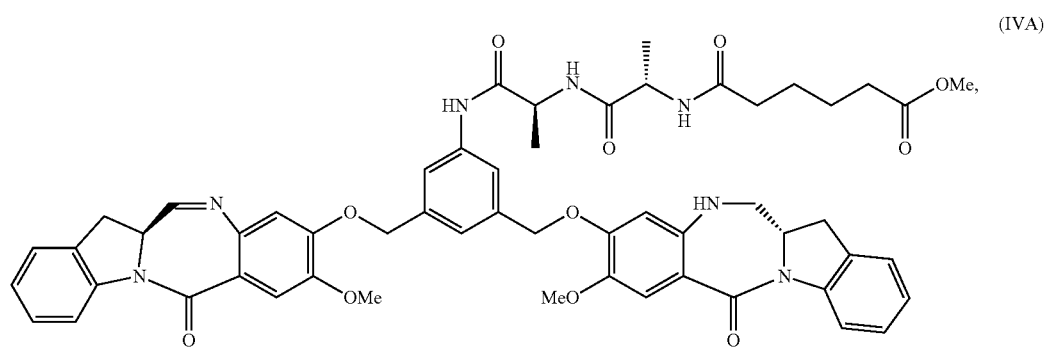 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
wherein $X_1$ is a sulfonate ester.
17. The method of claim 1, further comprising the steps of:
i) reacting the compound of formula (IIA) with a sulfonating agent to form a compound of formula (VIA):
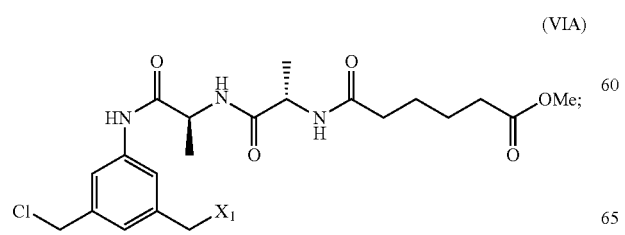
(VIA)

ii) reacting the compound of formula (VIA) with a compound of formula (a):

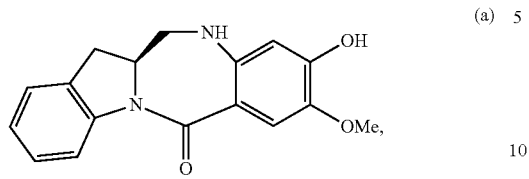

(a)

to form a compound of formula (IIIA):

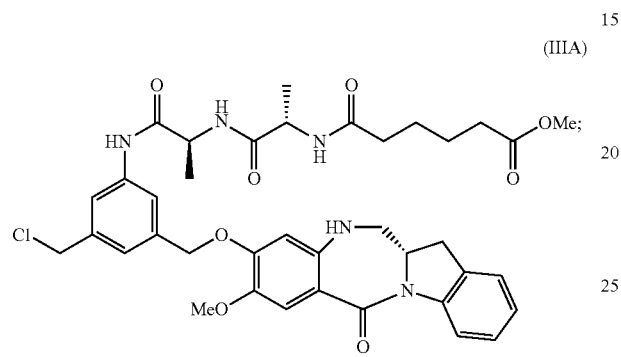

(IIIA)

and ii) reacting the compound of formula (IIIA) with a compound of formula (b):

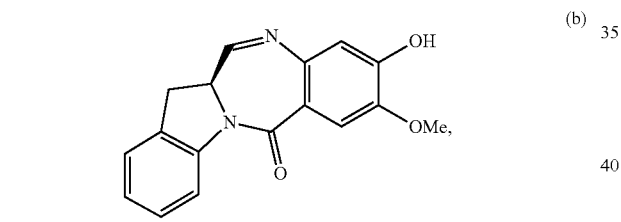

(b)

to form a compound of formula (IVA):

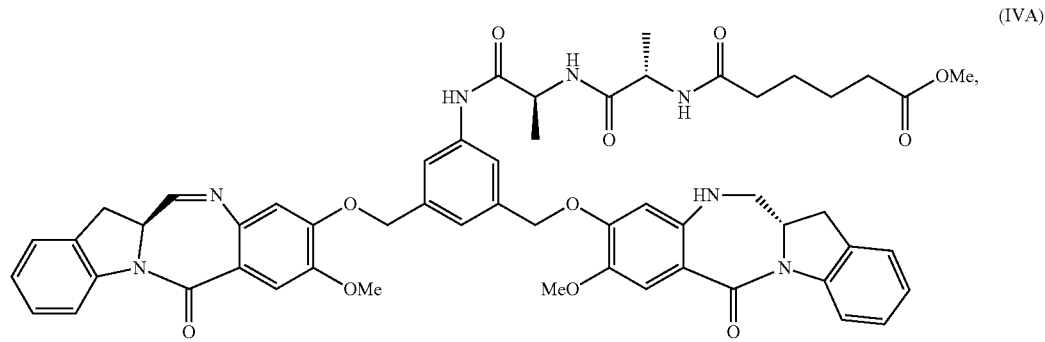 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

(IVA)

wherein $X_1$ is a sulfonate ester.

18. The method of claim 1, further comprising the steps of:

i) reacting the compound of formula (IIA) with a sulfonating agent to form a compound of formula (VIA):

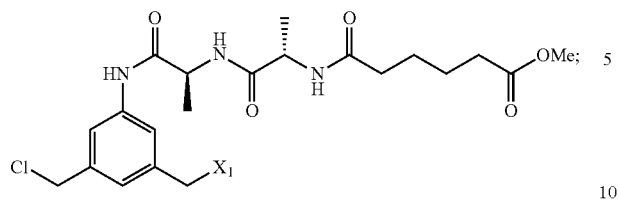
(VIA)
ii) reacting the compound of formula (VIA) with a compound of formula (b):
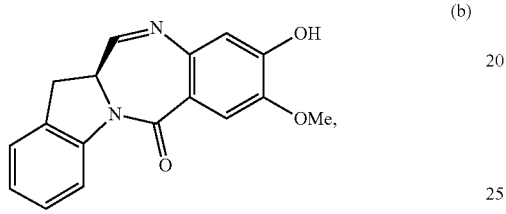
(b)
to form the compound of formula (VA):
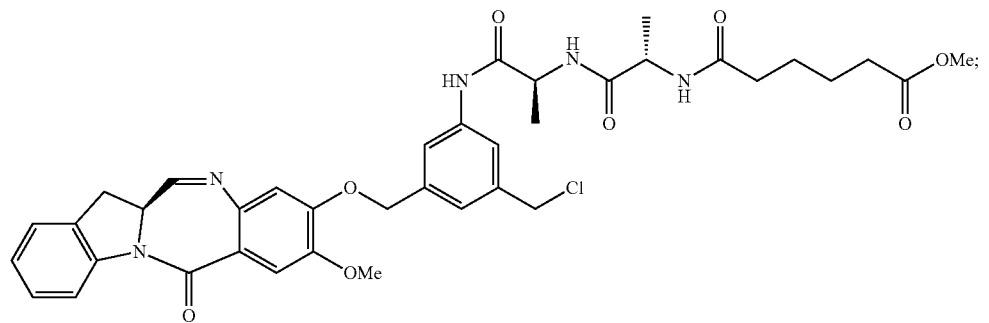
(VA)
iii) reacting the compound of formula (VA) with an imine reducing agent to form a compound of formula (IIIA):
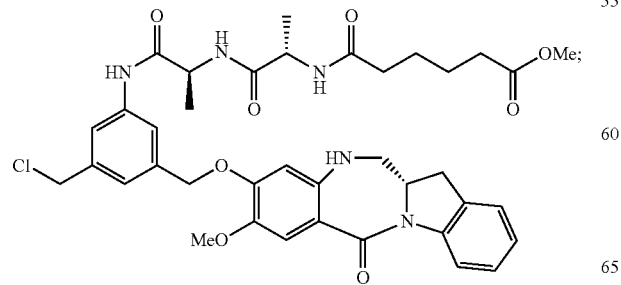
(IIIA)

and
iv) reacting the compound of formula (IIIA) with a compound of formula (b):
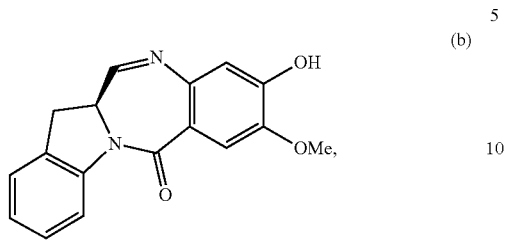
(b)
to form the compound of formula (IVA):
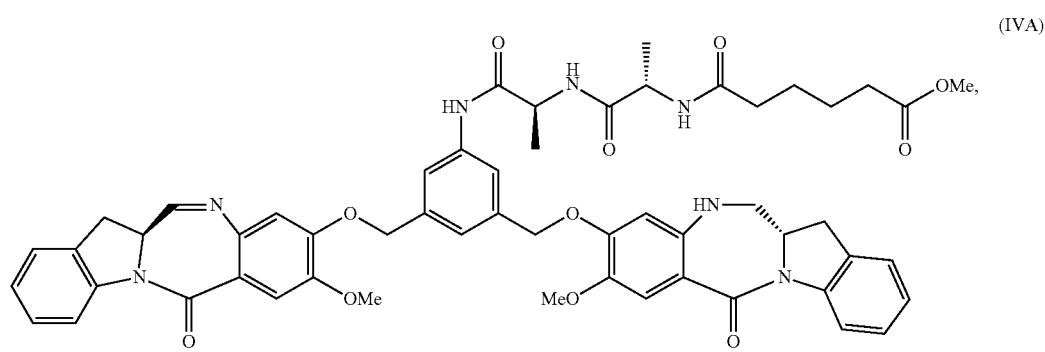 [SMILES: COC(=O)CCCCC(=O)N[C@@H](C)C(=O)N[C@@H](C)C(=O)Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]
(IVA)
wherein $X_1$ is a sulfonate ester.
19. A method of preparing a compound of formula (IIB):
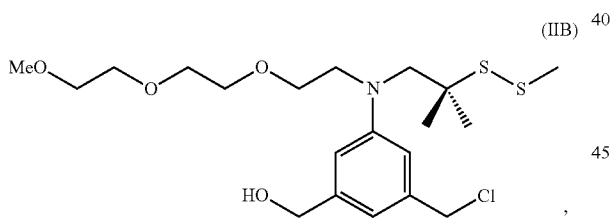
(IIB)
comprising reacting a compound of formula (IB):
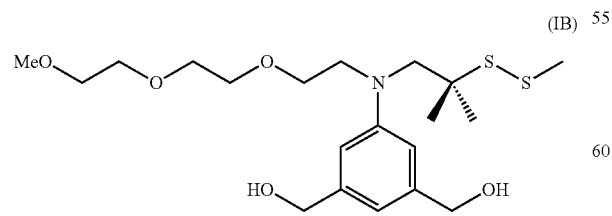
(IB)
with cyanuric chloride to form the compound of formula (IIB).

20. The method of claim 19, wherein 0.6 to 1.0 molar equivalent of cyanuric chloride relative to the compound of formula (IB) is used.

* * * * *